United States Patent [19]

Cercek et al.

[11] Patent Number: 5,270,171
[45] Date of Patent: Dec. 14, 1993

[54] CANCER-ASSOCIATED SCM-RECOGNITION FACTOR, PREPARATION AND METHOD OF USE

[76] Inventors: Boris Cercek; Lea Cercek, both of 4318 Camphor Ave., Yorba Linda, Calif. 92686

[21] Appl. No.: 539,686

[22] Filed: Jun. 18, 1990

Related U.S. Application Data

[63] Continuation-in-part of Ser. No. 167,007, Mar. 3, 1988, abandoned, which is a continuation-in-part of Ser. No. 22,759, Mar. 6, 1987, abandoned.

[51] Int. Cl.⁵ .................. C12Q 1/02; A61K 37/02; A61K 35/14; A61K 37/04; C07K 5/00; C07K 7/00; C07K 15/00; C07K 17/00; C07K 300; C07K 13/00
[52] U.S. Cl. .................. 435/29; 436/811; 436/813; 530/328; 530/327; 530/326; 530/325; 530/324; 530/350; 530/380
[58] Field of Search .................. 435/220, 183, 29; 436/813, 811; 530/328, 327, 326, 325, 324, 350, 380

[56] References Cited

U.S. PATENT DOCUMENTS

| | | |
|---|---|---|
| 4,001,080 | 1/1977 | Goust et al. |
| 4,444,744 | 4/1984 | Goldenberg |
| 4,645,738 | 2/1987 | Knowles et al. |
| 4,657,892 | 4/1987 | Brantl |

FOREIGN PATENT DOCUMENTS

| | | |
|---|---|---|
| 1147648 | 6/1983 | Canada |
| WO86/03007 | 5/1986 | PCT Int'l Appl. |
| WO87/07382 | 12/1987 | PCT Int'l Appl. |
| WO89/08662 | 9/1989 | PCT Int'l Appl. |
| WO90/04785 | 5/1990 | PCT Int'l Appl. |
| 445690 | 5/1974 | U.S.S.R. |
| 06595 | 9/1988 | World Int. Prop. O. |

OTHER PUBLICATIONS

Carrell et al. (1982) Nature 298:329-334.
Harris et al. (1987) Advances in Human Genetics Plenum Press, N.Y. pp. 1-62.
Stewart et al. (1979) Clin Immunol And Immunopathol 13:171-181.
Orjasaeter et al. (1979) B. J. Cancer 40:628-633.
L. Cercek, B. Cercek & C. I. V. Franklin, "Biophysical Differentiation Between Lymphocytes from Healthy Donors, Patients with Malignant Diseases and Other Disorders," *Brit. J. Cancer* 29, 345-52 (1974).

(List continued on next page.)

*Primary Examiner*—Christine M. Nucker
*Assistant Examiner*—D. R. Preston
*Attorney, Agent, or Firm*—Sheldon & Mak;

[57] ABSTRACT

A cancer recognition factor (SCM factor) useful in the performance of the structuredness of the cytoplasmic matrix (SCM) test has been isolated, purified to substantial homogeneity, and characterized, and methods for its use have been described. The factor is a peptide of at least 9 amino acid residues including a core sequence of 9 amino acid residues having an amphipathicity profile substantially equivalent to that of the sequence F-L-M-I-D-Q-N-T-K and produces at least a 10 percent decrease in the intracellular fluorescence polarization value of SCM-responding lymphocytes from donors afflicted with cancer. A synthetic SCM factor representing a consensus sequence of M-I-P-P-E-V-K-F-N-K-P-F-V-F-L-M-I-D-Q-N-T-K-V-P-L-F-M-G-K is fully active. Antibodies specific for SCM factor are useful in immunoassays that can detect the factor, including detection in cancer cells grown in vitro. The SCM factor is useful for screening of blood samples and other body fluids or cell aspirates for the presence of malignancy in the donor. The multiple action spectrum of the SCM factor including cancer proliferation and invasion promotion, as well as inhibition of the host's immune defense mechanisms and synthesis of SCM factor by cancer cells, represents a novel target for cancer management. Methods for reducing in vivo activity of the SCM factor, such as dialysis or antibody neutralization, can also be useful in the management of cancer.

68 Claims, 3 Drawing Sheets

OTHER PUBLICATIONS

L. Cercek & B. Cercek, "Application of the Phenomenon of Changes in the Structuredness of Cytoplasmic Matrix (SCM) in the Diagnosis of Malignant Disorders: A Review," *Europ. J. Cancer* 13, 903–15 (1977).

L. Cercek & B. Cercek, "Changes in SCM-Responses of Lymphocytes in Mice After Implantation with Ehrlich Ascites Cells," *Europ. J. Cancer* 17, 167–71 (1981).

L. Cercek & B. Cercek, "Changes in the SCM Response Ratio ($RR_{SCM}$) After Surgical Removal of Malignant Tissue," *Brit. J. Cancer* 31, 250–1 (1975).

L. Cercek & B. Cercek, "Apparent Tumour Specificity with the SCM Test," *Brit. J. Cancer* 31, 252–3 (1975).

S. Chaitchik, O. Asher, M. Deutsch & A. Weinreb, "Tumour Specificity of the SCM Test for Cancer Diagnosis," *Eur. J. Cancer Clin. Oncol.* 21, 1165–70 (1985).

J. A. V. Pritchard et al., "A Clinical Assessment of Fluorescence Polarisation Changes in Lymphocyte Stimulated by Phytohaemagglutinin (PHA) in Malignant and Benign Diseases," *Eur. J. Cancer Clin. Oncol.* 18, 651–9 (1982).

B. Cercek, "Letter to the Editor," *Cancer* 53, 17A–18A (1984).

L. Cercek & B. Cercek, "Letter to the Editor: Comments on 'the SCM Test for Cancer, An Evaluation in Terms of Lymphocytes from Healthy Donors and Cancer Patients' by Mitchell, Wood, Pentycross and Bagshawe, Br. J. Cancer (1980) 41, 772," Br. J. Cancer 42, 947–9 (1980).

H. Orjasaeter, G. Jordfald & I. Svendsen, "Response of T-lymphocytes to Phytohaemagglutinin (PHA) and to Cancer-tissue-associated Antigens, Measured by the Intracellular Fluorescence Polarization Technique (SCM Test)," *Br. J. Cancer* 40, 628–33 (1979).

L. Cercek & B. Cercek, "Effects of Ascorbate Ions on Intracellular Fluorescein Emission Polarization Spectra in Cancer and Normal Proliferating Cells," Cancer Detection and Prevention 10, 1–20 (1987).

S. Stewart, K. I. Pritchard, J. W. Meakin & G. B. Price, "A Flow System Adaption of the SCM Test for Detection of Lymphocyte Response in Patients with Recurrent Breast Cancer," *Clin. Immunol. & Immunopathol.* 13, 171–81 (1979).

N. D. Schnuda, "Evaluation of Fluorescence Polarization of Human Blood Lymphocytes (SCM Test) in the Diagnosis of Cancer," *Cancer* 46, 1164–73 (1980).

K. Suzuki & Y. Sasaki, "Studies on Encephalitogenic Fragments of Myelin Protein. IV. Synthesis of Glycine Analogs of Tryptophan-containing Fragment," *Chem. Pharm. Bull.* 22, 2181–7 (1974).

A. A. Gershkovich, V. K. Kibirev, S. B. Serebryanyi, Y. T. Terletsckaya, E. P. Kozulina & Y. V. Belik, "A Study of the Properties of Synthetic Analogs of the Tryptophane-containing Fragment 113-121 of the Basic Protein of Myelin," *Khim. Prirod. Soedinen.* 4, 557–65 (1979).

C. M. Deber & M. E. M. Young, "Association of Carbon-13 Enriched Human Encephalitogenic Nonapeptide with a Membrane Surface," *J. Biol. Chem.* 254, 6341–5 (1979).

C. Blake & B. J. Gould, "Use of Enzymes in Immunoassay Techniques: A Review," *Analyst* 109, 533–47 (1984).

M. Oellerich, "Enzyme-Immunoassay: A Review," *J. Clin. Chem. Clin. Biochem.* 22, 895–904 (1984).

J. L. Marx, "How Cancer Cells Spread in the Body," *Science* 244, 147–8 (1989).

B. W. Hancock & R. C. Rees, "Interleukin-2 and Cancer Therapy," *Cancer Cells* 2, 29–32 (1990).

J. G. Kaplan & C. Bona, "Proteases as Mitogens: The Effect of Trypsin and Pronase on Mouse and Human Lymphocytes," *Exp. Cell Res.* 88, 388–94 (1974).

Y. Shai, T. K. Brunck & I. M. Chaiken, "Antisense Peptide Recognition of Sense Peptides: Sequence Simplification and Evaluation of Forces Underlying the Interaction," *Biochemistry* 28, 8804–11 (1989).

G. Fassina, M. Zamai, M. Brigham-Burke & I. M. Chaiken, "Recognition Properties of Antisense Peptides to $Arg^8$-Vasopressin/Bovine Neurophysin II. Biosynthetic Precursor Sequences," *Biochemistry* 28, 8811–18 (1989).

M. R. Potter & M. Moore, "Natural Cytotoxic Reactivity of Human Lymphocytes," *Immunology* 37, 187–94 (1979).

E. Cameron, A. Campbell & T. Jack, "The Orthomolecular Treatment of Cancer III. Reticulum Cell Sarcoma: Double Complete Regression Induced by High-dose Ascorbic Acid Therapy," *Chem.-Biol. Interactions* 11, 387–93 (1975).

N. Bishun, T. K. Basu, S. Metcalfe & D. C. Williams, "The Effect of Ascorbic Acid (Vitamin C) on Two Tumor Cell Lines in Culture," *Oncology* 35, 160–2 (1978).

OTHER PUBLICATIONS

S. Bram, P. Froussard, M. Guichard, C. Jasmin, Y. Augery, F. Sinoussi-Barre & W. Wray, "Vitamin C Preferential Toxicity for Malignant Melanoma Cells," *Nature* 284, 629-31 (1980).

J. L. Marx, "What T Cells See and How They See It," *Science* 242, 863-5 (1988).

W. Becker, "Determination of Antisera Titres Using the Single Radial Immunodiffusion Method," *Immunochemistry* 6, 539-46 (1969).

R. W. Carrell, J.-O. Jeppsson, C.-B. Laurell, S. O. Brennan, M. C. Owen, L. Vaughan & D. R. Boswell, "Structure and Variation of Human $\alpha_1$-Antitrypsin," *Nature* 298, 329-34 (1982).

M. Fagerhol & D. W. Cox, "The Pi Polymorphism; Genetic, Biochemical, and Clinical Aspects of Human $_1$-Antitrypsin," in *Advances in Human Genetics* (H. Harris and K. Hirschhorn, eds., Plenum Press, N.Y., 1981), vol. 11, pp. 1-62.

W. Troll, M. S. Meyn & T. G. Rossman, "Mechanisms of Protease Action in Carcinogenesis," in *Carcinogenesis—A Comprehensive Survey, vol. II: Mechanisms of Tumor Promotion and Cocarcinogenesis* (T. J. Slaga, A. Sivak & R. K. Boutwell, eds., Raven Press, N.Y., 1978), pp. 301-312.

T. G. Rossman & W. Troll, "Protease Inhibitors in Carcinogenesis: Possible Sites of Action," in *Carcinogenesis, vol. V: Modifiers of Chemical Carcinogenesis* (T. J. Slaga, ed., Raven Press, N.Y. 1980) pp. 127-148.

G. J. Cianciolo, "Anti-inflammatory Effects of Neoplasia," in *Inflammation: Basic Principles and Clinical Correlates* (J. I. Gallin, I. M. Goldstein & R. Snyderman, eds., Raven Press, N.Y., 1988) Ch. 48, pp. 861-874.

E. Reich, "Tumor-associated Fibrinolysis," *Fed. Proc.* 32, 2174-5 (1973).

H. B. Bosmann, "Release of Specific Protease During Mitotic Cycle of L5178Y Murine Leukaemic Cells by Sublethal Autolysis," *Nature* 249, 144-5 (1974).

I. Hayashi & B. I. Carr, "DNA Synthesis in Rat Hepatocytes: Inhibition by a Platelet Factor and Stimulation by an Endogenous Factor," *J. Cell Physiol.* 125, 82-90 (1985).

D. Moscatelli & D. B. Rifkin, "Membrane and Matrix Localization of Proteinases: A Common Theme in Tumor Cell Invasion and Angiogenesis," *Biochim. et Biophys. Acta* 948, 67-85 (1988).

B. Hagmar, W. Ryd & L. J. Erkell, "Why Do Tumors Metastasize? An Overview of Current Research," *Tumor Biol.* 5, 141-9 (1984).

C. A. McWherter, W. F. Walkenhorst, E. J. Campbell & G. I. Glover, "Novel Inhibitors of Human Leukocyte Elastase and Cathepsin G. Sequence Variance of Squash Seed Protease Inhibitor with Altered Protease Selectivity," *Biochemistry* 28, 5708-14 (1989)

D. C. Linch, D. L. Wallace & K. O'Flynn, "Signal Transduction in Human T Lymphocytes," *Immunol. Rev.*, No. 95, pp. 137-159 (1987).

G. L. Nicolson, "Cancer Metastasis: Tumor Cell and Host Organ Properties Important in Metastasis to Specific Secondary Sites," *Biochim. et Biophys. Acta* 948, 175-224 (1988).

AMPHIPATHICITY PROFILE OF SCM-ACTIVE
FRAGMENT F4 OF SYNTHETIC SCM FACTOR

FLMIDQNTK
AMINO ACID SEQUENCE

FIG. 1

AMPHIPATHICITY PROFILE OF SCM-ACTIVE
OCTAPEPTIDE ISOLATED AS IMPURITY FROM
EXPERIMENTAL ALLERGIC ENCEPHALITOGENIC PEPTIDE

FWGAEGQR
AMINO ACID SEQUENCE

FIG. 2

SCHEMATIC DEPICTION OF AN ELISA ASSAY FOR DETECTION OF SCM FACTOR

1. SCM FACTOR ATTACHMENT TO A SOLID PHASE

2. INCUBATION WITH RABBIT ANTI SCM-FACTOR ANTIBODIES

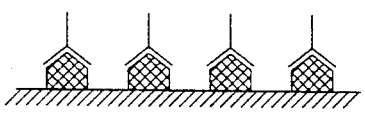

3. INCUBATION WITH GOAT ANTI-RABBIT-IgG
   (ANTIBODY LABELLED WITH ALP-ENZYME)

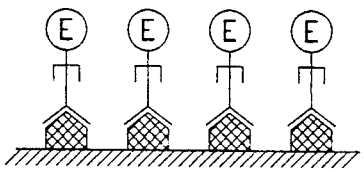

4. ADDITION OF P-NITROPHENYLPHOSPHATE (PNP) SUBSTRATE:

$$E + PNP \xrightarrow{H_2O} E + PN-OH + HP$$

5. MEASUREMENTS OF OPTICAL DENSITY (O.D.) AT 405 nm (PN-OH)

*FIG. 3*

CANCER-ASSOCIATED SCM-RECOGNITION FACTOR, PREPARATION AND METHOD OF USE

CROSS-REFERENCES

This application is a continuation-in-part of Ser. No. 07/167,007, filed Mar. 3, 1988, which itself was a continuation-in-part of Ser. No. 07/022,759, filed Mar. 6, 1987, and now abandoned. Both of these prior patent applications are by Dr. Boris Cercek and Dr. Lea Cercek and are entitled "General Cancer-Associated SCM-Recognition Factor, Preparation and Method of Use." This application is also related to prior patent applications, all by Drs. Boris & Lea Cercek: (1) Ser. No. 06/838,264, filed Mar. 10, 1986 (now abandoned), and Ser. No. 07/260,928, filed Oct. 21, 1988, a continuation-in-part of Ser. No. 06/838,264, both entitled "Provision of Density Specific Blood Cells for the Structuredness of the Cytoplasmic Matrix (SCM) Test"; and (2) Ser. No. 06/867,079, filed May 27, 1986 (now abandoned), and Ser. No. 07/222,115, filed Jul. 20, 1988, a continuation-in-part of Ser. No. 06/867,079, both entitled "Method for Measuring Polarization of Bathochromically Shifted Fluorescence." The disclosures of these related patent applications are incorporated herein by this reference.

TABLE OF CONTENTS

BACKGROUND
SUMMARY
DRAWINGS
DEFINITIONS
DESCRIPTION
I. ISOLATED AND PURIFIED GENERAL CANCER-ASSOCIATED SCM-RECOGNITION FACTORS
  A. Purification
  B. Structure of the Isolated Cancer-associated SCM-recognition Factor
II. SYNTHETIC CANCER-ASSOCIATED SCM-RECOGNITION FACTOR
  A. Sequence of the Synthetic SCM Factor Molecule
  B. Properties of the Synthetic SCM Factor
  C. Production and Activity of Fragments of Synthetic SCM Factor III. USE OF THE PURIFIED AND SYNTHETIC SCM FACTORS
  A. Performance of the SCM Test
  B. Immunochemical Uses of the SCM Factors
  C. Detection of SCM-specific Receptors
  D. DNA Sequences and Vectors
IV. RELATIONSHIP BETWEEN THE SCM FACTOR AND CANCER
  A. Protection of Cancer Cells in Vivo by SCM Factor
  B. Use of the SCM Factor in the Detection and Management of Cancer
EXAMPLES
  Example 1—Initial Purification of the General Cancer-associated SCM Factor from Blood Plasma
  Example 2—SCM Activity of Initially Purified SCM Factor from Example 1
  Example 3—Further Purification of the SCM Factor of Example 1
  Example 4—SCM Activity of Further Purified Preparations of Example 3
  Example 5—Final Purification of SCM Factor of Example 3 by RP-HPLC
  Example 6—Alternative RP-HPLC Purification of SCM Factor
  Example 7—SCM Activity of RP-HPLC Purified Preparations of Example 6
  Example 8—Identification and Isolation of SCM-active Tryptic Peptides from SCM Factor Purified from Blood Plasma of Patients with Breast Cancer and Lung Cancer
  Example 9—Use of the Isolated SCM Factor as the Challenging Agent in the SCM Test
  Example 10—Activity of the Tryptic Peptide of Example 8 in the SCM Test
  Example 11—Cross-reactivity of Isolated SCM Factors
  Example 12—Modification of the SCM Response by the Isolated SCM Factor
  Example 13—Effect of the Isolated SCM Factor on Lymphocyte Cytotoxicity
  Example 14—Amino Acid Sequences of Isolated SCM Factors
  Example 15—SCM Activity of Synthetic SCM Factor
  Example 16—Fragments of Synthetic SCM Factor
  Example 17—Activity of Fragments of Synthetic SCM Factor of Example 16 in the SCM Test
  Example 18—Amphipathicity Profiles of SCM-active Peptides and Peptide Fragments
  Example 19—Induction of SCM Response Characteristic of Malignancy from Healthy Donors by Synthetic SCM Factor
  Example 20—Preparation of Antibodies to Synthetic SCM Factor
  Example 21—ELISA Assay for SCM Factor
  Example 22—Activity of Anti-SCM Antibodies
  Example 23—Determination of SCM-factor Levels in Ultrafiltrates of Blood Plasmas by ELISA Assay
  Example 24—$NH_2$-terminal Amino Acid Sequences of SCM Factor Secreted from Human Cancer Cells in Culture
  Example 25—Reactivity of SCM Factor Secreted from Human Cancer Cells in Culture with Anti-SCM-factor Antibodies
  Example 26—Detection of SCM Factor in Human Cancer Cells in Culture by ELISA Assay
  Example 27—Effect of SCM Factor on DNA Synthesis
  Example 28—Effect of SCM Factor on Inhibition of Serine Proteases by $\alpha$-1-PI Protease Inhibitor
  Example 29—Interaction of Protease Inhibitor $\alpha$-1-PI with SCM-factor Receptors
  Example 30—Inhibition of SCM Factor Synthesis
  Example 31—Effect of Synthetic SCM Factor and Fragments Thereof on Natural Cytotoxicity of Lymphocytes

BACKGROUND

Many diseases occurring in humans and animals can be detected by the presence of foreign substances, particularly in the blood, the substances being specifically associated with a disease or condition. Tests for antigens or other such substances produced as a result of such diseases show great promise as a diagnostic tool for the early detection of the particular disease which produced the antigen or other substance. Procedures for the detection of such substances must be reliable, reproducible, and sensitive in order to constitute a practical diagnostic procedure for health care providers. In addition, any such procedure should be able to be carried out quickly and inexpensively by persons of ordinary skill and training in laboratory procedures.

For example, in the treatment of the various malignancies that afflict humans and animals, referred to generally as cancer, it is recognized that early detection is the key to effective treatment, especially as most therapeutic procedures are more effective and safer in relatively early stages of cancer than in later stages. For example, many chemotherapeutic drugs that are toxic to malignant cells are also toxic to normal cells, and the higher doses required to cure or arrest more advanced cases of cancer can cause uncomfortable and serious side effects. Also, surgery is most often effective only before the disease has spread or metastasized. Far too many cases of cancer are only discovered too late for effective treatment.

Accordingly, there has been and continues to be a great need for reliable tests that can diagnose cancer at early stages, and a great deal of research effort has gone to this end. In this connection new tests and procedures are being developed to effect early diagnosis of cancer.

One extremely desirable aspect of such a test is its ability either to detect all types of cancer generally, or to detect specific types of cancer, depending on the materials used. The former application of such a test is very important in mass screenings of large patient populations, as would be done in routine checkups. In such mass screenings a test dependent on a particular type of cancer would not be desirable, as there are literally hundreds, if not thousands, of types of cancer and a test that could spot only one or a few types of the disease is far too likely to miss many cases of cancer. In general, these patients would present either no symptoms or vague generalized symptoms that could not be readily linked to a particular type of cancer, so there would be no basis for suspecting a particular type and administering a test specific for that type.

In contrast, once the presence of malignancy is known or strongly suspected, it would be desirable to have a test that could pinpoint the particular type of malignancy present. Such a test could add greatly to the efficiency of treatment, because many of the most effective cancer therapies, such as chemotherapeutic agents, are only effective against one type of cancer or at best, a narrow range of types, and the wrong chemotherapy can do more harm than good.

In an effort to meet this need and to improve the diagnosis and early detection of cancer in human and animal bodies, a test procedure has been developed which involves the measurement of changes in the structuredness of the cytoplasmic matrix (SCM) of living lymphocytes when exposed either to phytohaemagglutinin or to cancer-associated antigens. This procedure has been described in L. Cercek, B. Cercek, and C. I. V. Franklin, "Biophysical Differentiation Between Lymphocytes from Healthy Donors, Patients with Malignant Diseases and Other Disorders," *Brit J. Cancer* 29, 345–352 (1974), and L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

In accordance with this procedure, a subpopulation of potentially SCM-responding lymphocytes is separated from a blood sample of the patient being tested and the lymphocytes are incubated with malignant tissue or extracts of malignant tissue. If the blood sample donor is afflicted with a malignancy, there is a characteristic SCM response that can be differentiated from the SCM response of lymphocytes from donors not afflicted with a malignancy. The SCM response is determined by measuring changes in intracellular fluorescein fluorescence polarization of the SCM-responding lymphocytes.

The changes seen in the SCM test are believed to reflect changes in the internal structure of the lymphocyte as the lymphocyte is activated for synthesis. These changes are seen as a decrease in the fluorescence polarization of the cells when polarized light is used to excite the fluorescein present in the cells. Fluorescence polarization is a measure of intracellular rigidity; the greater the intracellular mobility, the less the measured fluorescence polarization. An observed decrease in fluorescence polarization is thought to result mainly from changes in the conformation of the mitochondria, the energy-producing organelles of the cell. The change in the mitochondria is believed to result from the contractions of the cristae or inner folds of the mitochondrial membrane. The SCM reflects the forces of interaction between macromolecules and small molecules such as water molecules, ions, adenosine triphosphate, and cyclic adenosine phosphate. Perturbations of these interactions result in changes in the SCM.

The SCM test is capable of responding to a relatively small quantity of malignant cells. About $10^9$ cells in a person weighing 70 kg are enough to cause the lymphocytes to respond in the SCM test in the characteristic pattern of malignancy. In mice, when as few as $3.5 \times 10^5$ Ehrlich ascites (tumor) cells are implanted, the pattern of the response in the SCM test is altered; response to cancer-specific antigens is induced, while the normal response to phytohaemagglutinin is virtually eliminated (L. Cercek and B. Cercek, "Changes in SCM-Responses of Lymphocytes in Mice After Implantation with Ehrlich Ascites Cells," *Europ. J. Cancer* 17, 167–171 (1981)).

The SCM test allows early detection of cancer, often much earlier than is possible by conventional methods, with relatively little discomfort to the patient except as may be involved in taking a blood sample.

However, this procedure does have disadvantages. For example, it requires preparation of crude extracts from tumor tissues and the like or the use of the tumor tissue itself as a source of cancer-associated antigens. There are several major problems with the use of malignant tissue or extracts of such tissue in the SCM test. For example, it is sometimes difficult to obtain the required quantity of tissue. Also, the use of whole tissues or crude extracts of tissues can introduce interfering substances into the test procedure. These interfering substances can adversely affect the sensitivity of the test or adversely affect the test results themselves. The presence or absence of these interfering substances can easily vary from batch to batch of malignant tissue, introducing undesirable variability into the SCM test. Additionally, because the interfering substances are present in whole tissue or crude extracts, they are very difficult to identify or quantitate.

Accordingly it is very desirable to identify, separate, and purify the factor or factors that provoke a response by SCM-responding lymphocytes. The use of such purified factor or factors would enhance the SCM cancer screening test because interfering substances would not be present, and would aid in the study of cancer, its causes and its effects on human and animal bodies. The availability of purified factors would allow the production of specific antibodies against them. Such antibodies would be useful for both diagnosis and treatment of cancer.

It is also very desirable to determine the complete chemical composition and structure of such SCM-active factors. If they turn out to be peptides or proteins, it would be especially desirable to determine their complete amino acid sequence. The knowledge of their complete amino acid sequence would allow their production by either solid-phase peptide synthesis techniques or recombinant DNA techniques. The application of these techniques would result in the availability of larger quantities of the factors without the necessity of isolating them from blood plasma or cancer tissue.

SUMMARY

We have discovered cancer recognition factors in body fluids, in particular in blood plasma, and purified these factors to substantial homogeneity. These factors produce a response in SCM-responding lymphocytes obtained from a donor with cancer that is identical to the response produced in such lymphocytes by cancer-associated extracts and/or tumor tissue in the SCM test. As described herein, the factors are designated in the singular and are referred to herein as the "cancer recognition factor useful in the structuredness of the cytoplasmic matrix (SCM) test," as the "cancer recognition factor," or merely as the "SCM factor."

The activity of the SCM factor can be demonstrated at a number of stages of purification of the factor from plasma, beginning with a step of ultrafiltration. In this step molecules with an apparent molecular weight of less than 1,000 daltons are separated from molecules with a larger molecular weight by ultra filtration through a filter with a nominal molecular weight cutoff of 1,000 daltons. The SCM factor is found in the fraction passing through the filter, in contrast to most other peptides and all proteins. The factor consists essentially of low molecular weight peptide passing through such filters and producing at least a ten percent decrease in the intracellular fluorescence polarization value of SCM-responding lymphocytes isolated from donors afflicted with cancer when used to challenge lymphocytes in the standard SCM test.

Further purification of the SCM factor, as described below, results in a substantially homogeneous peptide of 29 to 35 amino acid residues. Because the SCM factors isolated from blood plasma samples obtained from patients with different types of cancer were largely homologous, a synthetic 29-amino-acid peptide, designated "synthetic SCM factor," was prepared. This peptide was fully active in the SCM test; certain fragments of this peptide, as described below, were also active in the SCM test.

1. Peptides Possessing SCM-Factor Activity

As determined from studies on fragments of synthetic SCM factor, a peptide of at least 9 amino acid residues including a core sequence of 9 amino acid residues having an amphipathicity profile substantially equivalent to that of the sequence F-L-M-I-D-Q-N-T-K is expected to have SCM-factor activity and to produce at least a 10 percent decrease in the intracellular fluorescence polarization value of SCM-responding lymphocytes from donors afflicted with cancer.

The core sequence of 9 amino acid residues can be F-$X_{15}$-M-$X_{17}$-$X_{18}$-$X_{19}$-$X_{20}$-$X_{21}$-K. In this sequence, $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T. These substitutions are examples of "conservative" amino acids substitutions, in which substitution of one of the amino acids of the group for another amino acid is expected to cause essentially no change in the structure of activity of the peptide because the properties of the amino acids are so similar. In particular, the core sequence can be F-L-M-I-D-Q-N-T-K.

Determination of the amino acid sequences of purified SCM factor obtained from blood plasma with patients with different types of cancer has led to the conclusion that such factors consist essentially of a peptide of from 29 to 35 amino acid residues including a core sequence at amino acid residues 14-22 of F-L-M-I-$X_{18}$-Q-N-T-K, where $X_{18}$ is D or E.

Particular examples of peptides conforming to this general sequence pattern and having SCM-factor activity include:

(1) $X_1$-I-P-P-$X_5$-V-K-F-N-K-P-F-V-F-L-M-I-D-Q-N-T-K-$X_{23}$-P-L-F-M-G-K, where: $X_1$ can be V, M, or S; $X_5$ can be E or D, and $X_{23}$ can be T or V; particular peptides of this sequence pattern are V-I-P-P-E-V-K-F-N-K-P-F-V-F-L-M-I-D-Q-N-T-K-V-P-L-F-M-G-K and M-I-P-P-E-V-K-F-N-K-P-F-V-F-L-M-I-D-Q-N-T-K-V-P-L-F-M-G-K;

(2) M-I-P-P-E-V-K-F-N-K-P-F-V-F-L-M-I-D-Q-N-T-K-C-P-C-F-M-G-C;

(3) X1-I-P-P-E-V-K-F-N-K-P-F-V-F-L-M-I-D-Q-N-T-K-C-C-L-F-M-G-K, where $X_1$ can be M or V, typically M;

(4) X-I-P-P-E-V-K-F-N-K-P-F-V-F-L-M-I-D-Q-N-T-K-R-P-L-F-M-G-K, where $X_1$ can be R or S, typically S;

(5) V-I-P-P-E-V-K-F-N-K-P-F-V-F-L-M-I-D-Q-N-T-K-C-P-L-F-M-G-K;

(6) V-I-P-P-E-V-K-F-N-C-P-F-V-F-L-M-I-D-Q-N-T-K-V-P-L-F-M-G-K;

(7) $X_1$-I-P-P-E-V-K-F-N-K-P-F-V-F-L-M-I-D-Q-N-T-K-C-P-C-F-M-G-C or X-I-P-P-E-V-K-F-N-K-P-F-V-F-L-M-I-D-Q-N-T-K-C-P-C-F-M-G-C-V-V-N-C-T-E, where $X_1$ is R or S, where the sequence typically has 29 amino acids and $X_1$ is typically R;

(8) $X_1$-I-P-P-E-V-K-F-N-K-P-F-V-F-L-M-I-E-Q-N-T-K-S-P-L-F-M-G-K or $X_1$-I-P-P-E-V-K-F-N-K-P-F-V-F-L-M-I-E-Q-N-T-K-S-P-L-F-M-G-K-V-V-N-P-T-Q, where $X_1$ is V or S, where the sequence typically has 29 amino acids and $X_1$ is typically V; and (9) X1-I-P-P-E-V-K-F-N-K-P-F-V-F-L-M-I-E-Q-N-T-K-S-P-L-F-M-G-K-V-V-N-P-T-Q, where $X_1$ is S or V, typically S.

These sequences have considerable homology. Therefore, a "consensus" sequence of 29 amino acids, M-I-P-P-E-V-K-F-N-K-P-F-V-F-L-M-I-D-Q-N-T-K-V-P-L-F-M-G-K, has been synthesized. This "consensus" sequence is identical with one of the sequences determined from sequence analysis of preparations of SCM factors purified from blood plasma of a cancer patient, specifically, from patients with colon and lung cancer. Because substitution of certain amino acids for other amino acids in this sequence, as discussed above, is not expected to substantially alter the activity of the SCM factor, the following sequence derived from the "consensus" sequence by conservative amino acid substitutions is also expected to have SCM-factor activity: M-$X_2$-P-P-$X_5$-$X_6$-K-F-$X_9$-K-P-F-$X_{13}$-F-$X_{15}$-M-$X_{17}$-

$X_{18}$-$X_{19}$-$X_{20}$-$X_{21}$-K-$X_{23}$-P-$X_{25}$-F-M-G-K, in which $X_2$, $X_6$, $X_{13}$, $X_{15}$, $X_{17}$, $X_{23}$, and $X_{25}$ are each independently selected from the group consisting of I, L, and V; $X_5$ and $X_{18}$ are each independently selected from the group consisting of D and E; $X_9$, $X_{19}$ and $X_{20}$ are each independently selected from the group consisting of Q and N; and $X_{21}$ is selected from the group consisting of S and T.

Additionally, particular fragments of the consensus sequence or of peptides derived from the consensus sequence by conservative amino acid substitution are known (in the case of fragments of the consensus sequence itself) or expected (in the case of fragments of peptides derived from the consensus sequence by conservative amino acid substitution) to have SCM-factor activity. The sequences that represent fragments of the consensus sequence are, respectively: F-L-M-I-D-Q-N-T-K (amino acid residues 14–22)-; F-N-K-P-F-V-F-L-M-I-D-Q-N-T-K (amino acid residues 8–22); F-N-K-P-F-V-F-L-M-I-D-Q-N-T-K-V-P-L-F-M-G-K (amino acid residues 8–29); and M-I-P-P-E-V-K-F-N-K-P-F-V-F-L-M-I-D-Q-N-T-K (amino acid residues 1–22). The shortest of these peptides, F-L-M-I-D-Q-N-T-K, represents the core sequence itself.

The following peptides, derived from these peptides by conservative amino acid substitution, are also expected to have SCM-factor activity:

(1) F-$X_{15}$-M-$X_{17}$-$X_{18}$-$X_{19}$-$X_{20}$-$X_{21}$-K, wherein $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T;

(2) F-$X_9$-K-P-F-$X_{13}$-F-$X_{15}$-M-$X_{17}$-$X_{18}$-$X_{19}$-$X_{20}$-$X_{21}$-K, wherein $X_{13}$, $X_{15}$ and $X_{17}$ are each independently selected from the group consisting of I, L, and V; $X_{18}$ is selected from the group consisting of D and E; $X_9$, $X_{19}$ and $X_{20}$ are each independently selected from the group consisting of Q and N; and $X_{21}$ is selected from the group consisting of S and T;

(3) F-$X_9$-K-P-F-$X_{13}$-F-$X_{15}$-M-$X_{17}$-$X_{19}$-$X_{20}$-$X_{21}$-K-$X_{23}$-P-$X_{25}$-F-M-G-K, wherein $X_{13}$, $X_{15}$, $X_{17}$, $X_{23}$, and $X_{25}$ are each independently selected from the group consisting of I, L, and V; $X_{18}$ is selected from the group consisting of D and E; $X_9$, $X_{19}$ and $X_{20}$ are each independently selected from the group consisting of Q and N; and $X_{21}$ is selected from the group consisting of S and T; and (4) M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K, wherein $X_2$, $X_6$, $X_{13}$, $X_{15}$ and $X_{17}$ are each independently selected from the group consisting of I, L, and V; $X_5$ and $X_{18}$ are each independently selected from the group consisting of D and E; $X_9$, $X_{19}$ and $X_{20}$ are each independently selected from the group consisting of Q and N; and $X_{21}$ is selected from the group consisting of S and T.

2. Purification of Peptides Possessing SCM-Factor Activity

The SCM factor can be purified by ultrafiltering a body fluid from a donor afflicted with cancer in order to separate a first fraction of the body fluid comprising molecules having an apparent molecular weight greater than 1,000 daltons from a second fraction comprising molecules having an apparent molecular weight of less than 1,000 daltons. The body fluid is selected from the group consisting of peripheral blood, urine, and plasma. Preferably, after ultrafiltration the factor undergoes a further purification process comprising several stages, each stage resulting in a more highly purified factor.

The first stage of this purification process comprises elution from a gel filtration column with a fractionation range of from 0 to about 700 daltons and capable of separating the salts from the ultrafiltrate, the factor eluting at between about 0.3 and about 0.5 times the total chromatographic bed volume.

The second stage comprises elution from a gel filtration column having a fractionation range of from about 1500 daltons to about 30,000 daltons, the factor eluting from such a column at between about 0.4 and about 0.6 times the total chromatographic bed volume.

The next stage of this purification process comprises elution from an anion-exchange column of diethylaminoethyl cellulose at between about 0.28M to about 0.31M of ammonium bicarbonate.

The final stage comprises purifying the factor to substantial homogeneity by reverse-phase high-pressure liquid chromatography.

Although it is preferred to use the more highly purified preparations of the factor in the SCM test, the factor from any stage of the purification, including the initial ultrafiltrate, can be used in the test.

3. DNA Sequences Coding for the SCM Factor

DNA sequences encoding the SCM factor as described above are useful for both diagnostic purposes and for production of large quantities of SCM factor by recombinant DNA procedures.

Generally, the desired DNA sequence encodes the SCM factor in isolation from DNA encoding proteins normally accompanying SCM factor. Particularly important are DNA sequences encoding the core sequence of F-L-M-I-D-Q-N-T-K and the consensus sequence of M-I-P-P-E-V-K-F-N-K-P-F-V-F-L-M-I-D-Q-N-T-K-V-P-L-F-M-G-K.

The DNA sequence can be operably linked to control sequences effective in expressing the DNA encoding the SCM factor in compatible host cells. This DNA sequence, incorporating the control sequence, can be included in a vector capable of transfecting at least some of the host cells within which the DNA can be expressed. Host cells transfected with this vector are also within the scope of the invention.

4. Antibodies Specific for the SCM Factor and Their Use

Antibodies specific for the substantially purified SCM factors can be prepared by standard methods of preparing antibodies to peptides and are within the scope of the invention. Particularly important are antibodies specific for the core sequence and for the consensus sequence. The antibody can be a monoclonal antibody prepared by methods known in the art.

These antibodies can be used in a method for determining the level of SCM factor in a body fluid. The method comprises:

(1) mixing the body fluid and the antibody; and (2) determining the extent of reaction between the SCM factor in the body fluid and the antibody by performing an immunoassay. The immunoassay can be a radioimmunoassay, a fluorescence immunoassay, a chemiluminescence immunoassay, an enzyme-linked immunoassay, or an immunoassay dependent on aggregation of antigen-antibody complexes.

5. Use of Labeled SCM to Detect Specific Receptors

As an alternative to the SCM test for the detection of cancer, labeled SCM factor can be used to determine the presence of receptors specific for SCM factor on SCM-responding lymphocytes and the sensitization of the lymphocytes to the SCM factor. The method for determining the presence of receptors comprises:

(1) isolating SCM-responding lymphocytes;

(2) washing the isolated SCM-responding lymphocytes;

(3) incubating the isolated SCM-responding lymphocytes with a saturating quantity of a natural or synthetic SCM factor labeled with a detectable label; and (4) determining the extent of the binding of the labeled SCM factor to the SCM-responding lymphocytes in order to determine the presence of receptors specific for SCM factor on the lymphocytes and the sensitization of the lymphocytes to SCM factor.

6. Use of the SCM Factor in the SCM Test

The SCM factor according to the present invention can be used to detect cancer in the SCM test. When using an SCM factor purified from a body fluid of a patient with cancer, it is preferred to use a more highly purified preparation of the factor, particularly a preparation of the factor purified to substantial homogeneity by high-pressure liquid chromatography. However, the factor from any stage of the purification, including the initial ultrafiltrate, can be used in the test.

The SCM factor produces a positive response in the SCM test in a limited fraction of lymphocytes, known as "SCM-responding lymphocytes," derived from donors having a variety of different types of malignancies, regardless of the type of cancer present in the donor from which the SCM factor is isolated; the factor produces essentially no response in the SCM test in lymphocytes derived from donors free of malignancy. This feature makes the SCM factor useful for the general screening of blood samples or other body fluid samples for the presence of malignancy.

Most generally, the method for testing lymphocytes from a mammalian donor for the presence or absence of malignancy in the donor comprises:

(1) contacting a suspension of the lymphocytes with a substantially purified cancer recognition factor (SCM factor) as described above; and (2) determining the decrease in the structuredness of the cytoplasmic matrix of the lymphocytes resulting from the step of contacting the suspension of the lymphocytes.

A preferred method for quantifying the decrease in structuredness comprises the steps of: (1) measuring the fluorescence polarization, $P_S$, for an aliquot of the lymphocytes that has been contacted with the cancer recognition factor; (2) measuring the fluorescence polarization, $P_C$, for a control aliquot of the lymphocytes that has not been contacted; and (3) determining the ratio of $P_S$ to $P_C$. A ratio of $P_S$ to $P_C$ lower than about 0.9 indicates a positive response to the SCM factor and the presence of a malignancy in the donor of the lymphocytes.

A more preferred method comprises comparing $P_S$ to the fluorescence polarization of another aliquot of the lymphocytes contacted with a mitogen, $P_M$, typically phytohaemagglutinin, to determine an SCM response ratio, $RR_{SCM}$, where:

$$RR_{SCM} = P_S/P_M.$$

An $RR_{SCM}$ of less than about 0.9 indicates the presence of a malignancy in the donor of the lymphocytes.

Alternatively, the method of employing the SCM factor in the SCM test can comprise the steps of: (1) separating potentially SCM-responding lymphocytes from the blood sample; (2) contacting the separated lymphocytes with a cancer recognition factor to stimulate the lymphocytes; (3) contacting the stimulated lymphocytes with a fluorogenic agent precursor, defined as a nonfluorogenic compound hydrolyzable intracellularly to a fluorogenic agent, to penetrate the lymphocytes for intracellular enzymatic hydrolysis to the fluorogenic agent, thereby generating stimulated fluorogenic agent-containing lymphocytes; (4) exciting the stimulated fluorogenic agent-containing lymphocytes with polarized light thereby causing them to fluoresce; (5) measuring the vertically and horizontally polarized fluorescence emissions from the fluorescing lymphocytes for determining a polarization value for the fluorescing lymphocytes; and (6) comparing the determined polarization value for the stimulated fluor-containing lymphocytes with the polarization value for a control aliquot of lymphocytes from the same donor, thereby to indicate the presence or absence of cancer in the body of the donor of the lymphocytes. Steps (3) and (4) can occur simultaneously.

The lymphocytes can be excited with vertically polarized light. The polarization values when vertically polarized light is used are determined in a fluorescence spectrophotometer in accordance with the relationship:

$$P = \frac{I_V - GI_H}{I_V + GI_H},$$

where, $I_V$ and $I_H$ are the polarized fluorescence intensities in the vertical and horizontal planes, respectively; and G is a correction factor for the unequal transmission of the horizontal and vertical components of the polarized light through the optical system of the spectrophotometer.

7. Use of the SCM Factor in the Treatment of Cancer

Not only does the present invention provide a diagnostic technique for identifying subjects afflicted with cancer, it also comprehends methods for the treatment of such subjects. These methods are based on several observations described in detail below. These observations reveal that the SCM factor is produced by cancer cells, and that it has several effects: enhancement of DNA synthesis, protection of cancer-associated proteases against inhibition by their natural inhibitor α-1-PI and suppression of the natural cytotoxicity of killer lymphocytes against malignant cells. Such suppression of the natural cytotoxicity of killer lymphocytes can be the result of SCM factor action at various steps of the immune defense mechanism. Such SCM factor action can include decreasing the ability of the effector killer lymphocytes to form a complex with the target cancer cells or blocking of the signal transducing mitogen receptors in lymphocytes, thus decreasing production of cytolysins such as tumor necrosis factor (TNF) and other cytotoxic and/or cytolytic molecules. SCM factor action can also include direct interaction with and inactivation of such cytolytic molecules, and the scavenging of peroxides and other oxygen-containing reactive species produced by various leukocytes against cancer cells.

Because the SCM factor appears to protect cancer cells in several ways, reduction of the in vivo activity of the SCM factor should increase the efficiency of immunological surveillance by lymphocytes against malignant cells.

Most generally, this treatment method is a method of treating a cancer patient where at least one of the body fluids of the patient contains a cancer recognition factor. The factor is a peptide of at least 9 amino acid residues including a core sequence of 9 amino acid residues having an amphipathicity profile substantially equivalent to that of the sequence F-L-M-I-D-Q-N-T-K. The method comprises:

(1) treating a body fluid containing the cancer recognition factor to reduce the in vivo effect of the factor by selectively inactivating it; and (2) returning the body fluid to the patient, thereby to enhance the resistance of the patient to the cancer.

The body fluid can be peripheral blood. In this case, the step of treating the body fluid can comprise dialysis of the peripheral blood to remove peptides with an apparent molecular weight of less than 1,000 daltons. This selectively inactivates the cancer recognition factor by its removal from the blood.

Alternatively, the step of treating the body fluid can comprise neutralizing the cancer recognition factor in the body fluid with an antibody specific for it, or with univalent antigen-binding fragments of the antibody, such as Fab fragments or Fab fragments.

As another alternative, the step of treating the body fluid can comprise inactivating the cancer recognition factor with an antisense peptide whose amino acid sequence is that encoded by the antisense strand of a DNA sequence whose sense strand encodes an SCM factor.

These methods can further comprise the step of treating the body fluid with a natural or synthetic protease inhibitor non-homologous with α-1-PI protease inhibitor and non-homologous with any other protease inhibitor that is substantially inhibited by SCM factor, the protease inhibitor used for treatment being capable of inhibiting cancer-associated proteases protected against α-1-PI inhibition by SCM factor. They can also further comprise the step of treating the patient with a clinically acceptable metabolic inhibitor, such as ascorbic acid, that causes a decrease in production of the SCM factor by tumor cells.

Because the SCM factor is produced by cancer cells and is found in them, an alternative method of treatment involves directing an anti-cancer substance to cancer cells. This can comprise:

(1) tagging an antibody specific for SCM factor with the anti-cancer substance; and (2) administering the tagged antibody to a cancer patient so that the tagged antibody can bind to cancer cells of the patient, thereby directing the anti-cancer substance to the cancer cells. The antibody can be a monoclonal antibody.

Another alternative method of treatment focuses on the reversal of the NK-suppressive effect caused by SCM factor. As detailed below, this NK-suppressive effect can be localized to a particular region of the SCM factor--the carboxyl-terminal 22 residues. Accordingly, a method of reversing the NK-suppressive action of SCM factor in vivo can comprise administering to a patient at least one of whose body fluids contains SCM factor a SCM-factor-inhibiting substance in a quantity sufficient to substantially reverse the NK-suppressive action of the SCM factor and substantially restore normal NK activity of lymphocytes of the patient as measured by in vitro lysis of K562 cells by the lymphocytes. The SCM-factor-inhibiting substance can be antibodies to SCM factor, univalent antigen-binding fragments of antibodies to SCM factor, or antisense peptides whose amino acid sequences are those encoded by the antisense strand of DNA sequences whose sense strand encodes a NK-suppressive sequence as described below under "Use of the SCM Factor in Suppressing Natural Killer Activity."

8. Use of the SCM Factor in Imaging Cancer Cells

Because SCM factor is found in cancer cells, antibodies to SCM factor can also be used to image cancer cells, particularly for diagnostic purposes. The method comprises:

(1) labeling the antibody with an imaging substance; and (2) utilizing the labeled antibody to image cancer cells by exposing the cancer cells to the labeled antibody.

9. Use of the SCM Factor in Suppressing Natural Killer Activity

Both the substantially purified SCM factor and the synthetic SCM factor suppress the natural killer (NK) activity of lymphocytes. This NK-suppressive activity was found to be localized in amino acid residues 8–29 of the synthetic SCM factor, with an amino acid sequence of F-N-K-P-F-V-F-L-M-I-D-Q-N-T-K-V-P-L-F-M-G-K. Therefore, in accordance with the conservative amino acid substitutions described above, a substantially purified peptide of at least 22 amino acid residues including a natural killer-suppressive (NK-suppressive) sequence of F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K, wherein $X_{13}$, $X_{15}$, $X_{17}$, $X_{23}$, and $X_{25}$ are each independently selected from the group consisting of I, L, and V; $X_{18}$ is selected from the group consisting of D and E; $X_9$, $X_{19}$ and $X_{20}$ are each independently selected from the group consisting of Q and N; and $X_{21}$ is selected from the group consisting of S and T is expected to have NK-suppressive activity. Other fragments of the synthetic SCM factor, including fragment F1 (residues 1–22), F3 (residues 8–22), F4 (residues 14–22), F5 (residues 1–13), F7 (residues 14–29), and F8 (residues 23–29) had no NK-suppressive activity.

The ability of SCM factor or portions of SCM factor to exert NK-suppressive activity makes possible a method for assessing the effectiveness of an anti-cancer agent capable of inhibiting the growth of malignant cells on a cell culture. In this method, the cell culture includes both lymphocytes exhibiting NK activity and malignant cells. The method comprises:

(1) incubating the cell culture with the substantially purified NK-suppressive peptide in a quantity sufficient to substantially suppress the NK activity of the lymphocytes of the cell culture;

(2) adding the anti-cancer agent to the cell culture in a quantity sufficient to inhibit the growth of the malignant cells; and (3) determining the effect of the anti-cancer agent on the malignant cells by observing the inhibition of growth of the malignant cells caused by the anti-cancer agent in the essential absence of NK activity caused by the lymphocytes.

The NK-suppressive peptide or the entire SCM factor molecule can be used to modulate the activity of the immune system. Such modulation can be desirable in preventing rejection of transplants. The substantially purified NK-suppressive peptide can be used to suppress the NK activity of lymphocytes by administering it to the lymphocytes in a quantity sufficient to substantially suppress the NK activity of the lymphocytes as measured by the in vitro lysis of K562 cells. Similarly, a method for inducing immunosuppression in vivo can comprise administering an immunosuppressive fraction alone or in combination with a pharmaceutically acceptable carrier in a quantity sufficient to create a degree of immunosuppression capable of enhancing allograft survival. The immunosuppressive fraction can be a substantially purified natural or synthetic SCM factor or a NK-suppressive peptide.

DRAWINGS

These and other features, aspects, and advantages of the present invention will become better understood with reference to the following description, appended claims, and the accompanying drawings where:

FIG. 1 shows the amphipathicity profile of the SCM-active F4 fragment of the synthetic SCM factor, representing amino acid residues 14–22 of the synthetic SCM factor;

FIG. 2 shows the amphipathicity profile of the SCM-active octapeptide whose sequence is F-W-G-A-E-G-O-R and which has been previously found to occur as an impurity in some preparations of experimental allergic encephalitogenic peptide (EAE peptide);

FIG. 3 is a schematic depiction of one form of ELISA assay for the SCM factor;

Figure 4:
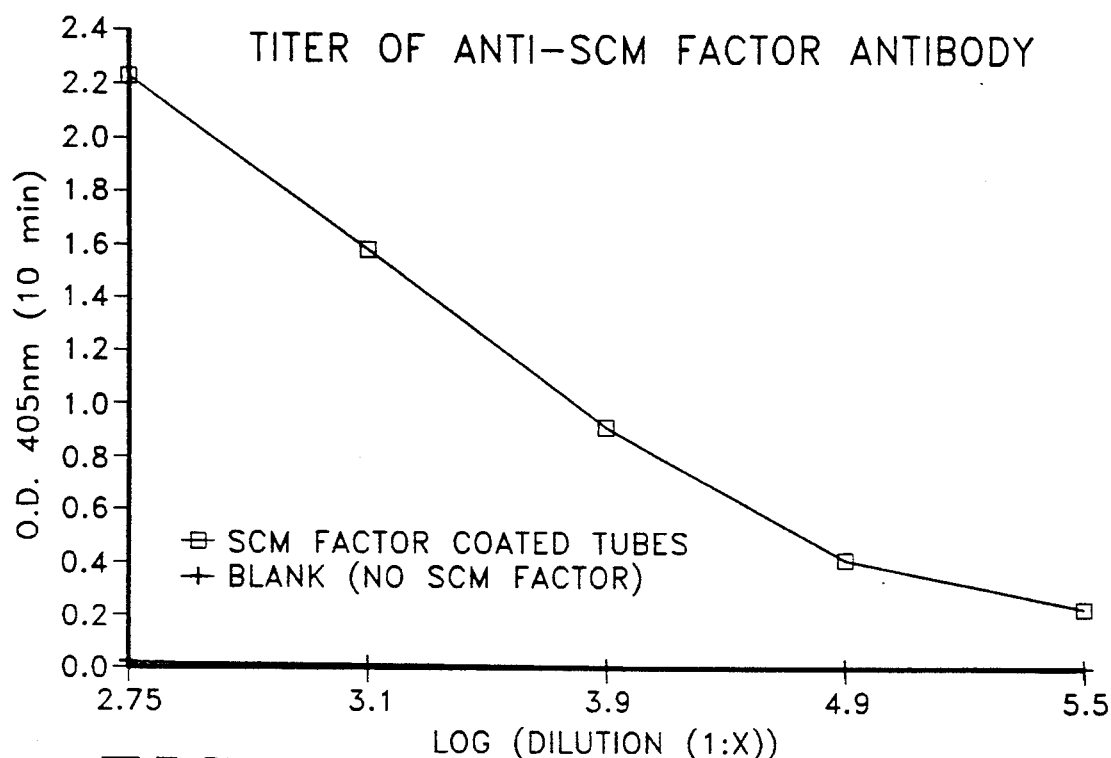
Figure 5:
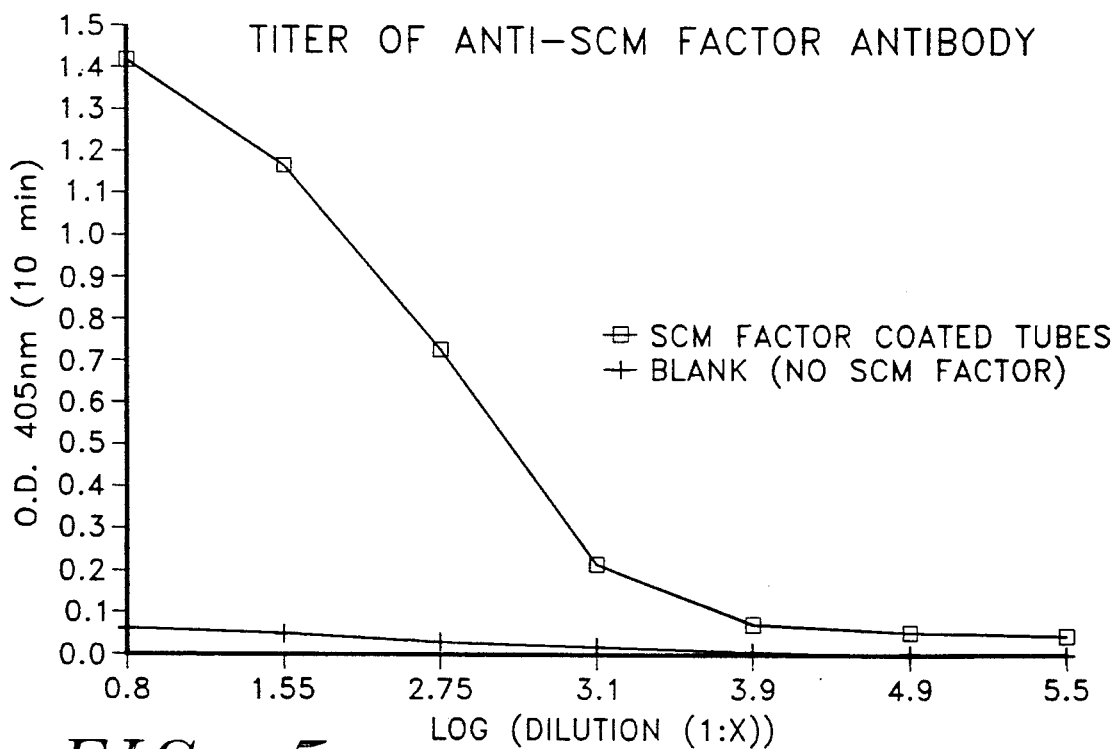

FIG. 4 shows the results obtained from an experiment in which the reactivity of antiserum raised against unconjugated SCM factor, as determined by absorbance at 405 nm in a version of the ELISA assay, was measured as a function of the dilution of the antiserum; and FIG. 5 shows the results obtained from an experiment in which the reactivity of antiserum raised against SCM factor conjugated with keyhole limpet hemocyanin (KLH), as determined by absorbance at 405 nm in a version of the ELISA assay, was measured as a function of the dilution of the antiserum.

DEFINITIONS

Definitions for a number of terms which are used in the following Description, Examples, and appended claims are collected here for convenience.

To the extent that these definitions may vary from meanings within the art, the definitions below are to control.

"General": Nonspecific with respect to the particular type of cancer afflicting either the donor of the body fluid from which the SCM factor of the present invention is purified, or the donor of the lymphocytes used with that factor in the SCM test.

"Fluorogenic Agent Precursor": A nonfluorogenic compound capable of being taken up by lymphocytes and converted intracellularly by hydrolysis into a fluorogenic compound, of which the example used herein is fluorescein diacetate (FDA).

"Standard SCM Test": An SCM test using 1.0 ml of a lymphocyte suspension at $6 \times 10^6$ cells/ml and 0.1 ml of the cancer recognition factor or mitogen, with FDA as the fluorogenic agent precursor and using an excitation wavelength of 470 nm and an emission wavelength of 510 nm for fluorescence polarization measurements.

"Apparent Molecular Weight" and "Nominal Molecular Weight Cutoff": Both of these terms refer to the fact that the separation of molecules by ultrafiltration according to size is approximate for molecules in the size range of SCM factor, and depends on conformation as well as size. Thus an ultrafilter with a nominal molecular weight cutoff of x daltons will separate molecules with an apparent molecular weight of less than x daltons from molecules with an apparent molecular weight greater than x daltons. However, some molecules with an actual molecular weight greater than x daltons will pass through such a filter.

"Substantially Pure Cancer Recognition Factor": Material exhibiting cancer recognition activity as determined in the SCM test and of such a state of purity that at least about 95% of other molecules with specific biological activity, including all proteins and larger peptides, is not present in the material. The term "substantially purified" refers to the same state of purity.

"Tryptic Peptide": A peptide cleaved from a larger peptide by the action of the proteolytic enzyme trypsin, which breaks peptide chains after lysine or arginine residues.

DESCRIPTION

This invention relates to our discovery and purification to substantial homogeneity of twelve peptides that are general cancer-associated SCM-recognition factors having sera isolated from a number of patients from different types of cancer. These peptides are all between 29 and 35 amino acids in length, crossreact in the SCM test, and show a striking homology in amino acid sequence. This homology is so striking that a 29-amino acid peptide representing a consensus sequence of the twelve purified peptides has been synthesized. This peptide, designated as "synthetic SCM factor", has the amino acid sequence M-I-P-P-E-V-K-F-N-K-P-F-V-F-L-M-I-D-Q-N-T-K-V-P-L-F-M-G-K. This synthetic peptide shares all of the properties of the general cancer-associated SCM-recognition factor isolated from lymphocytes, including activity in the SCM test and immunochemical reactivity. Even more unexpectedly, a region of nine amino acids within that sequence, amino acids 14–22, with the sequence F-L-M-I-D-Q-N T-K, is equally active in the SCM test. Other partial sequences, including amino acids 8–22, 8–29, and 1–22, that incorporate the 14–22 sequence are also fully active.

Biological properties of both the natural purified and the synthetic SCM factors are described. These properties are substantially identical, as far as has been determined, for the natural and synthetic SCM factors, and include: (1) the ability of the SCM factor to modify the SCM responses of lymphocytes from donors free of malignancy; (2) cross-reactivity of the factor isolated from donors with various types of cancer in the SCM test; (3) its ability to suppress the in vitro natural cytotoxicity of killer lymphocytes toward malignant cells; and (4) the newly discovered property of the SCM factor of protecting proteases that are believed to aid in the proliferation and invasion of cancer cells from inhibition by the natural inhibitor of those proteases, α-1-PI. Furthermore, the homology of the SCM factor with α-1-PI has been discovered, along with the fact that α-1-PI can reverse the responses in vitro of SCM-responding lymphocytes of cancer patients to the SCM factor. A method for purification of the SCM factor from blood plasma to substantial homogeneity is described, as are methods of using both the synthetic SCM factor and the SCM factor purified from plasma as challenging agents in the SCM test. Lymphocyte receptor assays and various immunochemical assays, including ELISA assays, are also described, as are DNA sequences coding for the SCM factors and vectors incorporating these sequences. Finally, methods of using the SCM factors in the management of cancer are described.

I. ISOLATED AND PURIFIED GENERAL CANCER-ASSOCIATED SCM-RECOGNITION FACTORS

The general cancer-associated SCM-recognition factor was isolated and purified to homogeneity from blood plasma obtained from patients with twelve different types of cancer. As detailed below, these peptides all are either 29 or 35 amino acids in length and are substantially homologous in amino acid sequence.

A. Purification

The purification of the SCM-recognition factor to substantial homogeneity from blood plasma was performed as described in U.S. patent application Ser. No. 07/167,007 by Drs. Boris and Lea Cercek, entitled "General Cancer-associated SCM-recognition Factor, Preparation and Method of Use" and incorporated herein by this reference. The purification process preferably occurs in five steps: (1) ultrafiltration; (2) desalting; (3) gel filtration; (4) anion-exchange chromatography; and (5) reverse-phase high-pressure liquid chromatography (RP-HPLC).

1. Ultrafiltration

The first step in purification of the SCM factor is obtaining an ultrafiltrate from a body fluid of a donor afflicted with cancer. The body fluid can be peripheral blood, blood plasma, or urine; if the fluid is peripheral blood, the blood is centrifuged to separate the red blood cells from the plasma. The donor of the body fluid used for isolation of the SCM factor can be either autologous or allogeneic with respect to the lymphocytes used for the SCM test. Alternatively, the SCM factor can be purified from cell aspirates or other cellular materials derived from patients with malignancies.

The ultrafiltration process separates the first fraction of the body fluid comprising molecules having an apparent molecular weight greater than 1,000 daltons from a second fraction comprising molecules having an apparent molecular weight less than 1,000 daltons. The general cancer-associated SCM factor of the present invention is found in the second fraction of the ultrafiltrate. The terms "apparent molecular weight" and "nominal molecular weight cutoff" are used herein because ultrafiltration is a somewhat imprecise method of separating molecules according to molecular weight in this molecular weight range, and the exact molecular weight excluded by a filter with a nominal molecular weight cutoff of 1,000 daltons depends somewhat on the conformation of the molecule. Molecules larger than 1,000 daltons in actual molecular weight can, in fact, pass through an ultrafilter with a nominal molecular weight cutoff of 1,000 daltons if, for example, the molecules are relatively long and narrow. In fact, the purified general cancer-associated SCM factors of the present invention are either 29 or 35 amino acids long and have molecular weights of approximately 3,200 or 3,900 daltons, respectively. Nevertheless, all of these peptides pass through an ultrafilter with a nominal molecular weight cutoff of 1,000 daltons.

Preferably, the separation of the second fraction from the first fraction is performed by filtration of the body fluid through an ultrafilter with a nominal 1,000-dalton molecular weight cutoff, such as, but not limited to, an Amicon ™ UM2 or YM2 filter (available from Amicon Corporation, Scientific System Division, Danvers, Mass. 01923).

The purity of a preparation of such a factor, at the ultrafiltrate stage or later, can be described by its specific activity. In this context, the term "specific activity" is defined as the reciprocal of the quantity of protein required to cause a particular degree of decrease, such as 20%, in the intracellular fluorescence polarization value when a particular fraction is used to challenge SCM-responding lymphocytes in the SCM test. The goal of purification of the SCM factor is to increase the specific activity of the SCM factor over the specific activity found in the crude ultrafiltrate. The process of purification can therefore be followed by determining the specific activity of the purified fractions at each stage. Since the protein concentration in the examples reported herein is only determined approximately in terms of ultraviolet absorbance, preferably at 220 nm, and the complete dose-response curve for the factor has not yet been determined, the characterization of various steps of the purification of the SCM factor described herein in terms of specific activity is only approximate. However, it is clear that the protein concentration decreases markedly as the factor moves through the various purification steps while the activity of the factor is relatively unaffected, thereby resulting in an increase in specific activity of the SCM factor. Nevertheless, even the ultrafiltrate can properly be described as consisting essentially of substantially purified general cancer-associated SCM-recognition factor, inasmuch as ultrafiltration through a membrane with a nominal molecular weight cutoff of 1,000 daltons removes from a biological fluid the overwhelming majority of molecules with any biological activity, including all proteins and larger peptides.

2. Desalting

The next step in the purification of the general cancer-associated SCM factor is a desalting step in which the fraction obtained from ultrafiltration is loaded on a chromatographic column capable of separating the salts therefrom. The material loaded onto the column is then eluted from the column with distilled water, and the portion eluting at an elution volume of between about 0.3 and about 0.5 times the total chromatographic bed volume, containing the SCM factor, is collected. Preferably, the column used in this step is a gel-filtration column with a fractionation range of from 0 to about 700 daltons, such as Sephadex ™ G-10 (Pharmacia, Uppsala, Sweden), a dextran gel. A polyacrylamide gel with corresponding separation characteristics can also be used.

3. Gel Filtration

The next step in the purification is another gel filtration step, again separating according to size. The SCM-containing material obtained from the desalting step is loaded onto another gel filtration column with a fractionation range of from about 1,500 to about 30,000 daltons. Preferably, the gel filtration column material is a dextran such as Sephadex TM G-50, but a corresponding polyacrylamide gel can also be used. The material loaded onto the column is then eluted therefrom with a weak aqueous solution of an ammonium salt. Preferably, the ammonium salt is ammonium bicarbonate, more preferably 50 mM ammonium bicarbonate. That portion eluting at an elution volume between about 0.4 times and about 0.6 times the total chromatographic bed volume contains the SCM factor and is collected.

4. Anion-exchange Chromatography

The next step in the purification is an anion-exchange chromatography step, separating by charge. The SCM factor-containing material from the previous gel filtration step is loaded onto an anion exchange column, preferably diethylaminoethyl-cellulose (DEAE-cellulose). The material loaded onto the column is then eluted therefrom with an increasing concentration of an ammonium salt. Preferably, the ammonium salt is ammonium bicarbonate and the increasing concentration of the ammonium salt is from 10 mM to 1.0M ammonium bicarbonate. The fraction eluting from the column at about 0.28M to 0.31M ammonium bicarbonate contains the SCM factor and is collected.

5. Reverse-phase High-pressure Liquid Chromatography

The final step of purification is reverse-phase high-pressure liquid chromatography (RP-HPLC), which separates by charge and/or hydrophobicity. Typically, the SCM factor-containing material from the DEAE-cellulose column eluate is loaded onto an Aquapore TM RP-300 RP-HPLC column with dimensions of 220 mm × 2.1 mm. Elution is then performed with a combination of two solvents: initially, 90 volume percent of 0.1 volume percent aqueous trifluoroacetic acid (TFA) (solvent A) and 10 volume percent of 0.09 volume percent of TFA in aqueous 70% acetonitrile (solvent B), followed by a gradient with an increasing concentration of solvent B. The SCM factor from all starting materials elutes as an homogeneous peak at a solvent composition of 26 volume percent solvent A and 74 volume percent solvent B.

Alternatively, RP-HPLC can be performed on a Beckman Instruments ULTRASPHERE ® ODS TM column. With this column, elution is then performed with a somewhat different solvent pattern, initially 70 volume percent of solvent A and 30 volume percent of 0.1 volume percent aqueous TFA in aqueous 70% acetonitrile (solvent C), followed by a gradient with an increasing concentration of solvent C. The SCM factor always elutes as an homogeneous peak at a solvent composition of 43.7 volume percent of solvent A and 56.3 volume percent of solvent C when the ULTRASPHERE ® column and this solvent system is used.

B. Structure of the Isolated Cancer-associated SCM-recognition Factor

The amino acid sequences of the SCM factors isolated from blood plasmas from patients with 12 different types of cancer have been determined by sequential Edman degradation and the results reported in Example 14. Certain residues are unidentified; these residues are likely cysteine and are reported herein as such. In nine out of the twelve cancers, the SCM factor was 29 amino acids long; in the remaining three, an additional six amino acids were present, yielding a total of 35 amino acids. In seven of twelve of the factor preparations, polymorphisms exist, in that there are conservative substitutions at one or two positions of the peptide. In these cases, the preparation contains two amino acids as identified by Edman degradation at one or two positions of the peptide. There were never more than two such substitutions. Also, in two cases, gastric sarcoma and prostate cancer, the SCM factor appears in two forms, one of 29 amino acid residues and the other of 35 amino acid residues. No forms of intermediate length are found. For seminoma of the testes, only the 35 amino acid form is found. These slight differences in amino acid sequence do not affect the cross-reactivity of the factors in the SCM test.

One region of the sequence is nearly invariant—residues 14–22. This sequence is F-L-M-I-D-Q-N-T-K, except in the factors for prostate cancer and seminoma of the testes, in which E (glutamate) replaces D (aspartate) at position 18. This change is extremely conservative, inasmuch as glutamate and aspartate have the same charge and differ by only one methyl group. This region is believed to be extremely significant for the functioning of the SCM factor, as discussed below.

C. Properties of the Isolated, Purified General Cancer-associated SCM-recognition Factor

1. Activity in the SCM Test

The purified SCM factors are fully active in the SCM test when used as a challenging agent for lymphocytes isolated from patients with several different types of malignancies. This activity can be demonstrated by assay at any point during the purification of the factor, starting at the ultrafiltrate. Details of the results of such assays are given below under "Examples." The greatest activity is obtained with material taken from the final RP-HPLC step. One-tenth milliliter of this fraction, having an approximate protein content of 40 picomoles of peptide, causes a decrease in intracellular fluorescence polarization of as much as 44.6% when used to challenge SCM-responding lymphocytes isolated from cancer patients, but causes no decrease in intracellular fluorescence polarization when used to challenge the same population of lymphocytes isolated from healthy donors.

2. Tryptic Peptides of the Factors

Purified preparations of the SCM factor from plasma of patients with lung cancer and breast cancer were subjected to tryptic digestion, followed by purification of the tryptic peptides by RP-HPLC. In each case, a particular fragment eluted at 30.4 volume percent of solvent A and 69.6 volume percent of solvent B, in RP-HPLC using the Aquapore RP-300 column. These fractions were found, by sequence analysis, to be the fragment of the SCM factor consisting of residues 8-22. (In both cases, residue 7 is lysine, and trypsin is known to cleave after lysine residues.)

These tryptic peptides are fully active in the SCM test (Example 10). Approximately $5 \times 10^{-2}$ femtograms of the tryptic peptide from the SCM factor isolated from plasma from patients with lung cancer (the lung cancer SCM factor), which is approximately 16,000 molecules, gave full activity in the SCM test when used as challenging agent for lymphocytes from donors with cancer. The fragment from the lung cancer SCM factor reacted equally well with lymphocytes from donors with lung cancer and breast cancer, but caused no response in the SCM test when used to challenge lymphocytes from normal donors. Further details are given below under "Examples." Significantly, both tryptic fragments include the nearly invariant region of the peptide from amino acids 14–22.

3. Cross-reactivity of the SCM Factor

The isolated factor of the present invention is designated as a general cancer-associated SCM-recognition factor because lymphocytes isolated from donors with all types of cancer respond to all preparations of the factor in the SCM test. The type of cancer afflicting the donor of the lymphocytes need not be the same as the type of cancer afflicting the donor of the body fluid from which the SCM factor was purified (Example 11).

4. Modification of the SCM Response by the General Cancer-associated SCM factor The isolated general cancer-associated SCM factor has a property of being able to modify the response of potentially SCM-responding lymphocytes obtained from donors free of malignancy when those lymphocytes are contacted with the factor. Before contact, lymphocytes from donors free of malignancy respond only to mitogens, such as phytohaemagglutinin, concanavalin A, and pokeweed mitogen, in the SCM test and do not respond to cancer-associated factors. However, after prolonged contact with the SCM factor, the SCM response of the cells is modified to respond only to cancer-associated factors and not to mitogens. In other words, contact by such lymphocytes with the SCM factor alters their response in the SCM test from the normal response of lymphocytes from donors free of malignancy to the response seen with lymphocytes from donors afflicted with cancer. Details on the demonstration of the modification of the SCM response are given under "Examples."

5. Effect of SCM Factor on Natural Cytotoxicity of Lymphocytes

The SCM factor has a property of irreversibly suppressing the in vitro spontaneous, natural cytotoxicity not only of the density-specific SCM-responding subpopulation of lymphocytes, but also of the general population of peripheral blood lymphocytes isolated by conventional techniques. The suppression of cytotoxicity by synthetic SCM factor is dose-dependent; only 11.5 femtomoles of the SCM factor is required for a 50% decrease of the cytotoxic effect. The suppression of cytotoxicity by SCM factor only requires a portion of the synthetic SCM molecule, and the region of the SCM factor responsible for the suppressive activity has been determined. It is believed that the SCM factor is involved in the defense of cancer cells against the attack of killer lymphocytes. This defense is believed to help the survival and unrestrained growth of cancer cells. The importance of the normal functioning of the immune system in controlling the growth of cancer cells is seen by the frequent occurrence of unusual forms of cancer in patients undergoing immune suppression. Such immune suppression can occur as a result of a disease such as Acquired Immunodeficiency Syndrome (AIDS) or as a result of the administration of immunosuppressive drugs to prevent rejection of transplants. An important example of such an unusual form of cancer is the occurrence of aggressive forms of Kaposi's Sarcoma, ordinarily a slowly-spreading and rarely fatal cancer, in AIDS patients. Details on the decrease of natural toxicity of lymphocytes are given below under "Examples."

However, this immunosuppressive effect of the SCM factor could in some instances be beneficial to a patient without cancer. For example, in patients receiving tissue transplants and at risk of rejection of the transplants, suppression of the cytotoxic action of lymphocytes by SCM factor and/or its active portion could help to prevent rejection of the transplants.

6. Homology with α-1-Protease Inhibitor

Computer search of the National Biomedical Research Foundation protein sequence data bank unexpectedly revealed that the amino acid sequences of the 12 isolated and purified general cancer-associated SCM-recognition factors are from 82.8% to 89.7% identical to an internal 28-33 amino acid sequence from the glycoprotein α-1-protease inhibitor (α-1-PI). The α-1-PI is a glycoprotein with a molecular weight of 55,000 daltons; it is a single polypeptide chain of 394 residues, and inhibits serine proteases. The sequence of the α-1-PI homologous to the SCM factor is, for factors from 9 out of 12 cancers, between amino acids 358 and 388 with serine at position 359 missing. For the remaining three cancers, gastric cancer, adenocarcinoma of the prostate, and seminoma of the testes, the homologous sequence is between residues 359 and 393. For the factor from seminoma testes, the homology is 100%; for the factor from prostate adenocarcinoma, the homology is 97%; and for the factor from gastric carcinoma, the homology is 94%. (These calculations exclude the unidentified residues.)

In the SCM factors identified from 9 out of 12 types of cancer, the amino-terminal residue is either methionine (5 cancers), or valine (4 cancers); in two additional factors, it is arginine. In 11 out of the 12 SCM factors, the amino acid serine, originally at position 359, next to the methionine and the active site of α-1-PI at position 358, is missing. In the seminoma testes SCM factor, the serine is present at the amino-terminal position, but methionine is absent.

The α-1-PI is a glycoprotein normally synthesized in the liver and rapidly released in the blood plasma. Normal levels of this glycoprotein in plasma are reported to be 1.3 g/l. It is an acute-reactive protein and its synthesis increases up to 4-fold in response to inflammatory signals and other homeostatic needs. It inhibits serine proteases and plays an important role in inflammatory processes by defending tissues against attack of proteolytic enzymes released by leukocytes at the site and source of inflammation. It is also thought to be part of the regulatory mechanisms of DNA synthesis, the cell division cycle, and differentiation and maturation processes. Inadequate protease inhibition unbalances these processes, often with deleterious consequences to the host. On the other hand, the absence of protease inhibition increases the fertilization efficiency, possibly promoting propagation of individuals with α-1-PI deficiencies. It has been suggested that the level or type of α-1-PI may influence pathophysiological processes and determine the occurrence, course, and severity of disease.

However, no genetic variants of α-1-PI are known that could account for the presence of SCM factors in blood plasma, either as a product of an aberrant cleavage at the active center during an inhibition reaction with a protease of a cancer cell, or as a defect in synthesis.

There is also no evidence that peptides similar to the SCM factors are generated as a result of breakage caused by ultrafiltration. Plasma from donors free of cancer, including plasma from patients with inflammatory diseases, was subjected to the same ultrafiltration process used as the first stage in the purification process of SCM factor. No fragments of α-1-PI or peptides similar to the SCM factor were detected in the ultrafiltrates. Furthermore, SCM-responding lymphocytes from cancer patients did not respond in the SCM test to such ultrafiltrates.

To eliminate the possibility that some specific, aggressive proteases secreted by tumor cells could cleave α-1-PI to produce molecules similar to SCM factors, we incubated overnight at 37° C. a variety of human tumor biopsies and human cultured cancer cell lines in the presence of: (a) pure human α-1-PI; (b) a complex of trypsin and α-1-PI; and (c) the molecular weight fraction of cancer patients' plasmas above 5,000 daltons containing α-1-PI, to ascertain that no labile genetic variant of α-1-PI is present in the plasma of cancer patients. After incubation, tissues or cells were separated by centrifugation and the supernatants were subjected first to ultrafiltration through 1,000-dalton molecular weight cutoff filters (Amicon ™ YM2) and then through further chromatographic procedures as used in the purification of SCM factors. None of these preparations yielded any SCM factor in quantities above those measured in supernatants of untreated control cancer cells.

7. Synthesis of SCM Factors by Cancer Cells in Culture

Metabolically active human cancer cells grown in culture, including T10806 fibrosarcoma cells, MCF7 breast cancer cells, A2780 ovarian cancer cells, and HCT80 colon cancer cells, excreted into serum-free tissue culture media molecules that, when taken through the SCM factor purification process, exhibited optical density peaks with retention times identical to those for SCM factor itself.

Sequencing of the picomolar amounts of SCM factor present in the purified preparations of SCM factor from supernatant medium in which the human MCF7 breast cancer cells and HCT80 colon cancer cells were grown confirmed that cells grown in vitro excrete molecules homologous with SCM factor. As shown in Example 24, 15 of the first 16 amino acid residues in the preparation from MCF7 breast cancer cells and 5 of the first 6 amino acid residues in the preparation from HCT80 colon cancer cells were identical to the sequence obtained from the SCM factor purified from plasma of breast and colon cancer patients, respectively.

These results were supported by ELISA tests using anti-SCM factor antibody (Example 25). When ELISA tests were performed on the cultured human cancer cells, the presence of SCM factor was detected in all of the cell lines tested. Different cell lines produced different quantities of SCM factor per cell under identical conditions. This variation might be an expression of differences in carcinogenic potential or metabolic activity of these different cell lines. This is supported by results showing the treatment of MCF7 breast cancer cells and T1080 fibrosarcoma cells with cycloheximide, a translational inhibitor of protein synthesis, caused a decrease in the synthesis of SCM factor. These results are in agreement with our hypothesis that cancer cells actively synthesize SCM factor molecules.

To eliminate the possibility that supernatant growth media and/or cultured cells would be contaminated by some variants of an α-1-PI produced by fetal cells, fetal calf serum was omitted from the growth media used for the last two medium changes. Additionally, we have subjected fetal calf serum to ultrafiltrations through filters with a cutoff of 1,000 daltons followed by the same chromatographic procedure used for the purification of SCM factor. The RP-HPLC eluate resulting did not show an optical density peak at the retention time characteristic of SCM factor molecules. However, another peak adjacent to that for SCM factor was collected in sequence. There was a non-linear sequence homology of 44.7% of the amino acids present between this peak and SCM factor that could indicate a similar genetic origin, but the difference in sequence is too large to justify any conclusion that SCM factor, like α-fetoproteins, is a product of cancer cell dedifferentiation. This suggests that SCM factor is not an ectopic, dedifferentiation tumor marker. More importantly, the SCM factor itself was not present in the fetal calf serum.

Active protein synthesis is required for production of SCM factor by cancer cells. Example 26 shows that treatment of cultured human cancer cells with the protein synthesis inhibitor cycloheximide considerably decreased the synthesis of the SCM factor as determined by the ELISA assay. Similarly, Example 30 shows that addition of ascorbate ions to cultures of MCF7 breast cancer cells considerably decreased the synthesis of SCM factor by the ELISA assay. Since ascorbate ions can inhibit protein synthesis by reverting mitochondria of cancer cells into the idle, orthodox conformation, as described in L. Cercek & B. Cercek, "Effect of Ascorbate Ions on Intracellular Fluorescein Emission Polarization Spectra in Cancer and Normal Proliferating Cells," *Cancer Detection & Prevention* 10, 1–20 (1987), these results confirm that active protein synthesis is required for production of SCM factor.

8. Stimulation of DNA Synthesis by SCM Factor

As shown in Example 27, SCM factor enhances DNA synthesis of rat hepatocytes grown in culture, as determined by tritiated thymidine uptake. The enhancement of DNA synthesis is dependent on the dose of SCM factor administered. The relationship between the activity of SCM factor in stimulating DNA synthesis and its possible role in promoting the growth of cancer cells is discussed below.

9. Blockage of α-1-PI Activity

SCM factor has no inhibitory or inactivating activity against serine proteases, unlike α-1-PI. However, SCM factor can block the inhibitory or inactivating activity of α-1-PI on proteases when SCM factor molecules are added to the protease before or simultaneously with the α-1-PI. This might result in a possible increase of protease activity in cancer cells producing SCM factor. The possible consequences of this are discussed below.

II. SYNTHETIC CANCER-ASSOCIATED SCM-RECOGNITION FACTOR

In view of the high degree of sequence homology between the SCM factors isolated from 12 different types of cancer, a synthetic SCM factor has now been prepared using standard solid-phase peptide synthesis methods. This synthetic SCM factor has a "consensus" sequence of 29 amino acids and shares the properties and activity of the isolated purified SCM factors.

The preparation of a synthetic SCM factor is desirable for a number of reasons: (1) availability and quantity without the necessity of isolation from cancer tissues; (2) uniformity of structure and activity; and (3) the possibility of varying the sequence in order to determine structure-activity relationships.

A. Sequence of the Synthetic SCM Factor Molecule

The synthetic SCM factor has the amino acid sequence M-I-P-P-E-V-K-F-N-K-P-F-V-F-L-M-I-D-Q-N-T-K-V-P-L-F-M-G-K.

This sequence is not the only sequence with 29 amino acids believed to possess SCM activity. It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

In view of these likely equivalencies, peptides of the sequence $M-X_2-P-P-X_5-X_6-K-F-X_{13}-F-X_{15}-M-X_{17}-X_{18}-X_{19}-X_{20}-X_{21}-K-X_{23}-P-X_{25}-F-M-G-L$, in which: $X_2$, $X_6$, $X_{13}$, $X_{15}$, $X_{17}$, $X_{23}$, and $X_{25}$ can each be I, L, or V; $X_5$ and $X_{18}$ can each be D or E; $X_9$, $X_{19}$ and $X_{20}$ can each be Q or N; and $X_{21}$ can be S or T, by definition are expected to have SCM factor activity. In this designation of the sequence, and corresponding designations elsewhere employing subscripts, the number appearing in the subscript indicates the position of the amino acid specified in a factor of 29 amino acids. For example, "$X_2$" refers to the second amino acid from the amino-terminus.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

B. Properties of the Synthetic SCM Factor Activity in the SCM Test

The synthetic SCM factor molecule is highly active in the SCM test. As shown below in Example 15, as little as 2 femtomoles ($2 \times 10^{-15}$ moles) of the synthetic SCM factor molecule produced a significant, 20%, decrease in intracellular fluorescence polarization in the SCM test when used to challenge SCM-responding lymphocytes. The synthetic peptide is active in the SCM test when used to challenge SCM-responding lymphocytes from donors with tumors of different histological type and in different organs. The corresponding fraction of SCM-responding lymphocytes from normal, healthy donors does not respond to the SCM factor in quantities as large as 960 picomoles ($960 \times 10^{-12}$ moles).

2. Induction of SCM-recognition Receptors in Lymphocytes from Healthy Donors The synthetic SCM factor can modify the SCM response of lymphocytes from healthy donors from the response characteristic of such lymphocytes (i.e., a response to PHA and no response to a cancer-associated factor) to the response characteristic of lymphocytes from donors with cancer (i.e., no response to PHA and a response to a cancer-associated factor). As detailed in Example 19, SCM-responding lymphocytes from healthy donors did not respond to synthetic SCM factor in the SCM test. However, after incubation for 2.5 hours at 37° C. in the presence of 400 picomoles of synthetic SCM factor per $5 \times 10^6$ cells, followed by three washes with phosphate-buffered saline (PBS), these cells showed a 37% decrease in intracellular fluorescence polarization, indicating the induction of receptors that can respond to the synthetic SCM factor.

The induction of these receptors requires protein synthesis. When the incubation is carried out in the presence of the protein synthesis inhibitors cycloheximide or actinomycin D at 10 $\mu g/5 \times 10^6$ cells, no response to synthetic SCM factor was induced, and the normal response to the mitogen PHA was not abolished.

3. Immunogenic Properties of Synthetic SCM Factor

The synthetic SCM factor has a predominantly α-helical secondary structure and is large enough to suggest that it could be presented by the major histocompatibility complex (MHC complex) for induction of the immune response. To test this assumption, the synthetic SCM factor was used to immunize experimental animals, as detailed below in Example 20. Both pure synthetic SCM factor and synthetic SCM factor conjugated to keyhole limpet hemocyanin (KLH) were used for immunization. In the latter case, the synthetic SCM factor was conjugated to the KLH via an added carboxy terminal cysteine residue on the SCM factor using N-succinyl bromoacetate as the cross-linking agent.

Other carriers, such as polylysine, can also be used for immunization. The use of such carriers is well-known in the art.

4. Effect of Synthetic SCM Factor and Fragments Thereof on Natural Cytotoxicity of Lymphocytes The synthetic SCM factor was shown to suppress the natural cytotoxic activity of lymphocytes against cancer cells (Example 31). The synthetic SCM factor decreased the natural killing (NK) efficiency of lymphocytes from normal healthy donors against K562 human myeloma target cells by 97% to 99.9% when a dose of 35 femtomoles of synthetic SCM factor was used per lymphocyte. A dose of 11.5 femtomoles per lymphocyte resulted in a 50% decrease in cytotoxicity (Table 23). Such quantities of SCM factor are expected to be present in the immediate surrounding of metabolically active cancer cells, which produce these molecules. This NK-suppressive effect is irreversible and cannot be removed by a thorough 3-times washing of the treated lymphocytes.

To find out to which part of the amino acid sequence of the synthetic SCM-factor molecule this NK-suppressive activity can be ascribed, we have tested various synthetic peptide fragments of the synthetic SCM-factor molecule. As can be seen from Example 31 (Table 26), the NK-suppressive effect was found only in the entire synthetic SCM factor (29 amino acids) and fragment F2 (amino acids 8–29). None of the fragments that did not contain the carboxyl-terminal region of the synthetic SCM factor, i.e., fragments F1, F3, F4, and F5 (Table 26) was active, which might indicate that the seven carboyxl-terminal amino acid residues are responsible for the suppression of NK activity of lymphocytes. However, the peptide fragment consisting of these seven carboxyl-terminal residues, residues 23–29 (fragment F8) did not suppress NK activity, and neither did peptide fragment F7, consisting of residues 14–29. This shows that the shortest sequence possessing NK-suppressive activity resides within the portion of the SCM factor molecule encompassing residues 8–29, and only the first seven amino-terminal residues are not important for NK-suppressive activity. This is in contrast to the portion of the synthetic SCM-factor molecule that is responsible for protection against inhibition by α-1-PI, which is the first seven amino-terminal residues of the molecule, or the portion of the molecule responsible for SCM activity itself, which occurs within the portion of the molecule between amino acid residue 14 and amino acid residue 22. Thus, the SCM factor exerts multiple functions in promoting the growth and invasion of cancer cells and in suppressing host defenses.

These results indicate that for NK suppressive activity to be expressed, the peptide need not contain the first seven amino-terminal residues of the synthetic SCM factor. Fragment F2 has the amino acid sequence F-N-K-P-F-V-F-L-M-I-D-Q-N-T-K-V-P-L-F-M-G-K. As explained above, variants of fragment F2 containing conservative amino acid substitutions are also expected to have NK-suppressive activity.

Furthermore, as can be seen from the results in Example 31, the NK-suppressive action of synthetic SCM factor not only affects the density-specific, SCM-responding subpopulation of lymphocytes, but a wider population spectrum of lymphocytes as isolated from peripheral blood by using conventional density-gradient centrifugation techniques employing the Histopaque density medium. This indicates that the effect of synthetic SCM factor on suppression of lymphocyte cytotoxicity has a broad spectrum of action. This broad spectrum of action includes various mechanisms by which the SCM factor can inhibit the cytotoxicity of lymphocytes against malignant cells. For example, we have observed that complex formation between the lymphocytes and K562 myeloma cells, one of the first steps in the killing process, is decreased when lymphocytes are treated with the SCM factor. Other effects of the SCM factor could be prevention of synthesis of leukolysins and/or direct inactivation of various cytolytic molecules, such as tumor necrosis factor (TNF).

The NK-suppressive activity of SCM factor or portions of SCM factor can be used to assess the effectiveness of an anti-cancer agent capable of inhibiting the growth of malignant cells in a cell culture that includes both lymphocytes exhibiting NK activity and malignant cells. The effectiveness can be assessed by:

(1) incubating the cell culture with a substantially purified NK-suppressive peptide, such as intact SCM factor or one of the peptides expected to have NK-suppressive activity described above, in a quantity sufficient to substantially suppress the NK activity of the lymphocytes of the cell culture;

(2) adding the anti-cancer agent to the cell culture in a quantity sufficient to measurably inhibit the growth of the malignant cells; and (3) determining the effect of the anti-cancer agent on the malignant cells by observing the inhibition of growth of the malignant cells caused by the anti-cancer agent in the essential absence of NK activity caused by the lymphocytes.

C. Production and Activity of Fragments of Synthetic SCM Factor

1. Sequences and Activity of Fragments

In order to determine which portion or portions of the synthetic SCM factor is responsible for its activity in the SCM test, five peptide fragments of the synthetic SCM factor were synthesized, designated F1 through F5. These represented the following portions of the intact molecules: F1, amino acids 1–22; F2, amino acids 8–29; F3, amino acids 8–22; F4, amino acids 14–22: and F5, amino acids 1–13. These fragments have the following amino acid sequences:

F1:  M-I-P-P-E-V-K-F-N-K-P-F-V-F-L-M-D-Q-N-T-K;
F2:  F-N-K-P-F-V-F-L-M-I-D-Q-N-T-K-V-P-L-F-M-G-K;
F3:  F-N-K-P-F-V-F-L-M-I-D-Q-N-T-K;
F4:  F-L-M-I-D-Q-N-T-K; and
F5:  M-I-P-P-E-V-K-F-N-K-P-F-V-F.

As detailed below in Example 17, fragments F1, F2, F3, and F4 are all active in the SCM test, while fragment F5 is inactive. All of the active fragments contain the 9-amino-acid segment of F4, and it is reasonable that this segment might represent the active site responsible for SCM activity.

Not only are peptides F1 through F4 active in the SCM test, variants of these peptides with conservative amino acid substitutions are also expected to have SCM activity and fall within the scope of the present invention. These conservative substitutions, as outlined above, include any of isoleucine, valine, and leucine for any other of these amino acids; aspartic acid for glutamic acid and vice versa; asparagine for glutamine and vice versa; and serine for threonine and vice versa. The existence of these conservative substitutions means that the following peptides are expected to have SCM activity:

M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K;

F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K;

F-$X_9$-K-P-F-$X_{13}$-F-$X_{15}$-M-$X_{17}$-$X_{18}$-$X_{19}$-$X_{20}$-$X_{21}$-K; and

F-$X_{15}$-M-$X_{17}$-$X_{18}$-$X_{19}$-$X_{20}$-$X_{21}$-K.

In these sequences, the subscripts designating particular amino acid residues have the same meaning as stated above in the discussion of conservative amino acid substitutions in the entire 29-amino-acid synthetic SCM factor.

2. Use of the Amphipathicity Profile to Determine SCM Activity

An amphipathicity profile is a plot of the relative hydrophilicity or hydrophobicity of segments of a peptide or protein. Amino acid residues range from quite hydrophilic (e.g., charged residues or serine) to quite hydrophobic (e.g., phenylalanine). Typically, the plot is presented as a moving average over a short stretch of amino acids within the protein or peptide. For specificity and recognition purposes, amphipathicity properties of short peptides can be as significant as the amino acid sequence itself. As shown below in Example 18, the amphipathicity profile of the SCM-active F4 peptide fragment is strikingly similar to the amphipathicity profile of the synthetic 8-amino-acid peptide with SCM-factor activity having the sequence of F-W-G-A-E-G-Q-R, even though there is only a limited sequence homology between this peptide and the F4 peptide. By contrast, the experimental allergic encephalitogenic peptide (EAE peptide) has a sequence of F-S-W-G-A-E-G-Q-R. The presence of the relatively hydrophilic serine between the hydrophobic residues phenylalanine and tryptophan alters the amphipathicity profile considerably. As detailed in our prior U.S. patent application Ser. No. 07/167,007, the EAE peptide has no SCM factor activity.

Given the importance of the amphipathicity profile of a peptide in determining whether the peptide has SCM factor activity, a peptide of at least 9 amino acid residues including a core sequence of 9 amino acid residues having an amphipathicity profile substantially equivalent to that of the sequence F-L-M-I-D-Q-N-T-K is expected to have SCM factor activity.

III. USE OF THE PURIFIED AND SYNTHETIC SCM FACTORS

Both the purified and synthetic SCM factors can be used as challenging agents in the SCM test, can be used to prepare antisera for the detection of the SCM factor, and can be used for the generation of DNA sequences that carry equivalent genetic information for use in a variety of genetic engineering procedures. As discussed below, this SCM factor can also be used in the management of cancer.

A. Performance of the SCM Test

The activity of both the purified SCM factor and the synthetic SCM factor, as well as the fragments of the SCM factor, is confirmed by its effect on viable SCM-responding lymphocytes in accordance with the prior publication by L. Cercek and B. Cercek, "Application of the Phenomenon of Changes in the Structuredness of Cytoplasmic Matrix (SCM) in the Diagnosis of Malignant Disorders: A Review," *Europ. J. Cancer* 13, 903–915 (1977). The general cancer-associated SCM-recognition factor of the present invention produces a significant decrease in the intracellular fluorescence polarization value of potentially SCM-responding lymphocytes from donors afflicted with cancer when used to challenge such lymphocytes in the SCM test as performed as described in that article. The degree of decrease of the intracellular fluorescein fluorescence polarization value of such challenged lymphocytes is substantial—at least 20% even if ultrafiltrate from plasma from donors afflicted with cancer is used to challenge such lymphocytes, and as great as 40–55% if purified RP-HPLC fractions or synthetic peptides are used.

Two previously established procedures are important for the proper performance of the SCM test as reported herein. These procedures are the isolation of potentially SCM-responding lymphocytes and the technique of measuring the fluorescence polarization values themselves, and their conversion into numbers meaningful for the SCM test.

1. Isolation of SCM-responding Lymphocytes

Several procedures for the isolation of potentially SCM-responding lymphocytes are described in the *European Journal of Cancer* review article, supra, and also in a prior patent application by B. Cercek and L. Cercek, U.S. application Ser. No. 07/260,928, filed Oct. 21, 1988, and entitled "Provision of Density Specific Blood Cells for the Structuredness of the Cytoplasmic Matrix (SCM) Test," incorporated herein by this reference. The separation of these lymphocytes from the general lymphocyte population is important for the proper performance of the SCM test, because only a relatively small portion of lymphocytes, approximately 20–25% of the total lymphocyte population, is capable of responding in the SCM test to cancer-associated factors. Therefore, to perform the test on unfractionated lymphocytes results in a much smaller observed decrease in the intracellular polarization value even when the lymphocytes actually capable of responding in the SCM test fully respond to the challenging agent used. Additionally, there exists another fraction of lymphocytes that responds in the SCM test in a different way. These cells do not respond at all to cancer-associated factors, but respond to PHA when isolated from donors with cancer. As detailed below, some variations of the SCM test compare the response to PHA to a cancer-associated factor, such as a peptide of the present invention, to determine whether or not the donor of the lymphocytes is afflicted with a malignancy. This second fraction of lymphocytes therefore must be rigorously excluded to avoid distorting the results.

Immunologically, the SCM-responding lymphocytes are T-cell mononuclear leukocytes. Although not fully understood, it is believed that SCM-responding lymphocytes are involved in the recognition of antigens that are circulating in the blood stream, expressed on cancer cells, or excreted by cancer cells into interstitial spaces of tumors. This recognition of antigens triggers the body's immune system. Accordingly, these cells become primed to recognize foreign substances, such as antigens, produced by the disease or condition affecting the body.

SCM-responding lymphocytes can be isolated by using either a single-density solution, a step gradient, or a continuous preformed gradient.

a. Isolation Using Single-density Solution

For the isolation of SCM-responding lymphocytes by the single-density solution method, a sample of peripheral blood is drawn from a donor and collected in a heparinized tube. After collection, the peripheral blood is treated with iron powder or carbonyl-iron powder and the tubes containing the blood-iron powder mixture are placed on a magnet to effect separation of the phagocytic cells along with the iron powder from a blood sample. A portion of the blood sample depleted of phagocytic cells is then transferred to a Ficoll™-Triosil™ density-gradient solution and centrifuged to effect separation of the SCM-responding lymphocytes based on density differences. This method of separation typically uses a density-gradient solution having a density of 1.081 g/cm$^3$ at 25° C. and an osmolality of 0.320 Osm/kg. Centrifugation is carried out at 550×g for 20 minutes at a temperature of 25° C. The SCM-responding lymphocytes are recovered using a Pasteur pipette to remove the cell layer separated above the density-gradient material. Removal of the density-gradient material must be avoided as far as is possible as this material includes various heavier plasma and cell components which interfere with the test results. Removal of the lighter plasma material should also be avoided as much as possible to eliminate the introduction of any contaminating components or SCM-nonresponding cells into the test samples.

Following separation, the SCM-responding lymphocytes are subjected to several washing steps, first in 0.9% preservative-free sodium chloride solution, then in complete Dulbecco's phosphate-buffered saline (PBS) and held at 37° C. for subsequent use in the SCM test procedure.

b. Isolation Using Step Gradient

For the isolation of SCM-responding lymphocytes using a step gradient, use a total blood sample depleted of phagocytic cells as described above, or the total population of peripheral blood lymphocytes can be used. The use of the total population of blood lymphocytes is preferred, as this avoids the use of possibly toxic iron or carbonyl-iron powder.

The isolation of the total population of peripheral blood lymphocytes for an heparinized blood sample is also performed using density-gradient centrifugation. This centrifugation step is performed by layering the heparinized blood on top of a solution of density 1.077 g/cm$^3$ containing a non-ionic synthetic polymer of sucrose with a molecular weight of about 400,000 and sodium diatrizoate. Both solutions are equilibrated to room temperature, and the volume of the heparinized blood. The layered solutions are then density solution is at least as great as the volume of centrifuged, typically at 30 minutes at room temperature at 550×g, so that the lymphocytes are banded at the interface between the solutions. The lymphocytes are then collected from the interface.

For the step of separation of the SCM-responding lymphocytes, a step gradient is made by layering a solution of density 1.0590 g/cm$^3$ and osmolality of 0.320 Osm/kg on top of a solution of density 1.0670 g/cm$^3$ and the same osmolality. These solutions are typically prepared from polyvinylpyrrolidone-covered silica media such as Percoll ™ (Pharmacia, Uppsala, Sweden). A volume of a blood sample or peripheral blood lymphocytes equal to about one-half the total volume of the step gradient is layered on top of the step gradient, and the mixture is centrifuged typically at 550×g for 30 minutes. The SCM-responding lymphocytes collect in a visible band between the first and second density solution and are harvested.

c. Isolation Using Continuous Preformed Gradient

As an alternative to the step gradient, a continuous preformed gradient can be used for the final separation of SCM-responding lymphocytes. This gradient spans a density range of between 1.050 g/cm$^3$ and 1.070 g/cm$^3$. It can be generated by centrifuging a solution of polyvinylpyrrolidone-covered silica at 26,000×g in a 29° fixed-angle rotor or at 11,400×g in a 34° fixed-angle rotor.

2. Performance of the SCM Test on Isolated SCM-responding Lymphocytes a. Measurement of SCM Values

The method for measuring the fluorescence polarization values of SCM-responding lymphocytes in the SCM test has been described in the *European Journal of Cancer* review article, supra, as well as in a prior patent application by B. Cercek & L. Cercek, Ser. No. 867,079, filed May 27, 1986, entitled "Method for Measuring Polarized Fluorescence Emissions," incorporated herein by this reference. As described in these references, SCM-responding lymphocytes previously separated from the test subject's peripheral blood are incubated in sterile glass tubes at 37° C. with a known concentration of either a mitogen such as phytohaemagglutinin or a cancer-associated antigen such as the general cancer-associated SCM-recognition factor which is the subject of the present invention. Other mitogens than phytohaemagglutinin (PHA), such as concanavalin A and pokeweed mitogen, have been used, but PHA is preferred for the SCM test. This incubation is initiated by adding 0.1 ml of the appropriately diluted mitogen or antigen to 1 ml of the cell suspension at 6×10$^6$ cells/ml. The incubation is then allowed to proceed for 30–60 min.

The incubated lymphocytes are then admixed in suspension with a suitable nonfluorogenic compound hydrolyzable intracellularly to a fluorogenic compound, referred to hereinafter as a fluorogenic agent precursor, such as fluorescein diacetate (FDA). The fluorescein diacetate is used at a final concentration of 2.5 mM or 0.7 mM in complete PBS at pH 7.4 and osmolality of 0.330 Osm/kg and is diluted from a concentrated stock solution prepared in acetone or glacial acetic acid, respectively. Aliquots of 0.2 ml of control or stimulated lymphocyte suspensions are slowly injected with a syringe into a beaker containing 3 ml of the FDA substrate solution.

The cells are exposed to the FDA for sufficient time (about 5 minutes) to allow for the penetration of the FDA substrate solution into the lymphocytes. Inside the cells, the nonfluorogenic fluorescein diacetate molecules are converted to fluorescein molecules by enzymatic hydrolysis.

The fluor-containing lymphocytes are isotropic in their response to polarized light since the polarization of the emitted fluorescence relative to that of the exciting light does not depend on the orientation of the plane-polarized light used to excite the lymphocytes. However, the conventional fluorescence polarization measuring apparatus used herein for these measurements uses vertically polarized exciting light to excite the lymphocytes, so the measurement process is described in terms of vertically polarized exciting light.

When exposed to excitation energy in the form of vertically polarized light, the fluorescein molecules emit fluorescence. The relationship between the vertically polarized and horizontally polarized emissions is measured. This can be done by measuring the polarized fluorescence intensities in both the vertical and horizontal planes and determining a polarization value (P value) in accordance with the following relationship:

$$P = \frac{I_V - GI_H}{I_V + GI_H},$$

where $I_V$ and $I_H$ are polarized fluorescence intensities in the vertical and horizontal planes, respectively, and G is a correction factor for the unequal transmission of the horizontal and vertical components of the polarized light through the optical system of the particular equipment used. The value of G is determined by dividing the intensity of the horizontally polarized light by the intensity of the vertically polarized light emitted from a 10$^{-7}$M solution of fluorescein in PBS excited with horizontally polarized light of the same wavelength as used for the SCM measurements. For the measurements reported herein, G=0.42.

The P value of stimulated lymphocytes, that is those lymphocytes that have been exposed to the general SCM-associated cancer recognition factor of the present invention, is compared with the P value of a control suspension of unstimulated lymphocytes from the same donor and the percent decrease in P value of the stimulated lymphocytes as compared to the P value of the control lymphocytes is an indication of the SCM-response to the cancer antigen.

Although the SCM response can be observed through some range of excitation and emission wavelengths, when using FDA as the fluorogenic agent precursor, it is strongly preferred to use an excitation wavelength of 470 nm and an emission wavelength of 510 nm. All results hereinafter described were obtained using those wavelengths. However, good results have also been achieved using an excitation wavelength of 442 nm and an emission wavelength of 527 nm.

The spectrophotometer utilized for SCM fluorescence measurements should be one of high sensitivity and stability and should be able to compensate for fluctuations in the intensity of the exciting light since the intensity of the polarized fluorescence emissions is recorded as a function of time and since the bulk concentration of fluorescein in the SCM measurements is only of the order of $10^{-8}$M to $10^{-9}$M. Also, broad band filter instruments are not suited for use for SCM measurements since SCM responses can be detected only within a narrow wavelength region. The maximum spectral slit width of the excitation monochromator should be 20 nm and the maximum spectral slit width of the emission monochromator should be 10 nm when the excitation monochromator is set at 470 nm and the emission monochromator at 510 nm. The spectrophotometer should also be fitted with a thermostatically controlled cuvette holder since the polarized fluorescent emissions are highly temperature dependent. The spectrophotometer should also be provided with means for measuring both the horizontal and vertical polarized components of the fluorescent emissions.

In the examples hereinafter set forth we used a Perkin-Elmer MPF-4 spectrophotometer which was equipped with a thermostatically controlled cuvette holder. All measurements were carried out at 27° C. The light source was a xenon lamp.

In measuring the fluorescence polarization, the intensities of the emissions parallel to and perpendicular to the vertical exciting light beam are recorded alternately with an automatic polarizer changer for about 6 minutes or until the intensity of the emission perpendicular to the vertically exciting light beam reaches 80–90% of the full scale deflection of the recorder.

It is necessary to correct these readings for any leakage of fluorescein from the cells and for any background of fluorescence in the substrate solution. To perform this correction, the cells are filtered away from the solution on a nitrocellulose filter of 0.22 μm pore size mounted in an appropriate filter head. Using the same fluorescence polarization measurement apparatus, the fluorescence intensities parallel to and perpendicular to the exciting light are obtained. The corrected fluorescein intensities for the cells are then obtained by subtracting the values obtained from the filtrate from the total fluorescence intensities extrapolated to the half time of filtration. This extrapolation is necessary because the background increases during the incubation because of the leakage of fluorescein from cells and spontaneous hydrolysis of FDA.

Alternatively, the method of compensating for background fluorescence described in the prior patent application by the Cerceks, Ser. No. 07/222,115, filed Jul. 20, 1988, entitled "Method for Measuring Polarization of Bathochromically Shifted Fluorescence," and incorporated herein by this reference, can be used. Briefly, this method eliminates the need to filter each sample by measuring the horizontally and vertically polarized fluorescence emissions at more than one wavelength and calculating the intracellular fluorescence emissions therefrom.

An SCM test performed according to the protocol described hereinabove, using 1.0 ml of a lymphocyte suspension at $6 \times 10^6$ cells/ml and 0.1 ml of the mitogen or antigen, with FDA as the fluorogenic agent precursor and using an excitation wavelength of 470 nm and an emission wavelength of 510 nm, is referred to herein as a "standard SCM test."

b. Interpretation of the SCM Test

The result of the SCM test is a value for the intracellular fluorescein fluorescence polarization of the challenged lymphocytes. This value is designated as a P value. The higher the measured P value, the greater the degree of polarization. The term "$P_S$" is used to refer to the P value of an aliquot of lymphocytes that has been challenged with a challenging agent such as an SCM factor of the present invention. Similarly, the term "$P_C$" is used to refer to the P value of an aliquot of lymphocytes not challenged with a challenging agent. When $P_S$ is compared with $P_C$, a ratio of $P_S$ to $P_C$ of less than about 0.9 is an indication of the presence of malignancy in the body of the donor of the challenged lymphocytes.

A preferred method of using the SCM factor as a challenging agent in the SCM test comprises comparing $P_S$ to the fluorescence polarization value, $P_M$ of another aliquot of the lymphocytes contacted with a mitogen such as phytohaemagglutinin (PHA), to determine an SCM response ratio, $RR_{SCM}$ where $RR_{SCM} = P_S \div P_M$. An $RR_{SCM}$ of less than about 0.9 indicates the presence of a malignancy. The use of the $RR_{SCM}$ is preferable because lymphocytes from donors free of malignancy respond to PHA but not to cancer-associated SCM factors, while lymphocytes from donors with malignancy do not respond to PHA but do respond to cancer-associated SCM factors. This double change in response pattern gives a sharper indication of the presence of a malignancy.

B. Immunochemical Uses of the SCM Factors

As discussed above, antibodies can be produced against SCM factors by immunizing antibody-producing animals either with the SCM factors themselves or SCM factors conjugated to carrier proteins such as keyhole limpet hemocyanin (KLH). These antibodies can be used for a number of immunochemical reactions, including assays of SCM factor in body fluids, detection of cancer cells in biopsies or aspirates by fluorescence microscopy or flow cytometric methods, and for other purposes discussed below under "Use of the SCM Factor in the Management of Cancer."

1. Immunoassays for SCM Factor

Once antibodies to SCM factor are produced, either monoclonal or polyclonal, they can be used in any type of immunoassays including: competitive or non-competitive sandwich immunoassays; colorimetric assays (e.g., ELISA, PGLIA (prosthetic-group-label immunoassay), SLIFIA (substrate-labeled fluorescence immunoassay), etc.); radiometric procedures such as radioimmunoassay (RIA); and assays employing luminescence, including both direct and catalyzed chemiluminescence. The direct chemiluminescence procedures can use luminophores such as acridinium derivatives; the catalyzed chemiluminescence procedures can use either enzymic, such as horseradish peroxidase (HRP) or other enzymatic or non-enzymatic catalysts, including metals. A large number of immunoassays are known in the art and have been summarized in M. Oellerich, "Enzyme-Immunoassay: A Review," *J. Clin. Chem. Clin. Biochem.* 22. 895–904 (1984) and C. Blake & B. J. Gould, "Use of Enzymes in Immunoassay Techniques," *Analyst* 109, 533–547 (1984), both of which are incorporated herein by this reference. For all of these types of immunoassays except immunoassays dependent on aggregation of antigen-antibody complexes, monovalent fragments of antibodies, such as Fab or Fab, fragments can substitute in some applications for entire bivalent antibody molecules.

One particularly useful type of enzyme-linked immunoassay is the enzyme-linked immunosorbent assay (ELISA assay). An ELISA assay for detection of SCM factor is described below in Example 21. Briefly, this assay entails: (1) attachment of SCM factor to a solid phase, typically plastic; (2) addition of sample to be assayed; (3) incubation of the solid phase with rabbit anti-SCM factor antibody; (4) incubation with goat anti-rabbit IgG antibody labeled with the enzyme alkaline phosphatase; (5) addition of p-nitrophenyl phosphate, a substrate for alkaline phosphatase; and (6) measurement of absorbance at 405 nm. In this procedure, only the alkaline phosphatase bound to antibody attached to the solid phase will yield color; the greater the quantity of SCM factor in the sample, the lower the absorbance measured at 405 nm. The ELISA test can be used to detect the level of SCM factor in ultrafiltrates of blood plasmas (Example 23), the presence of SCM factor in purified preparations from serum-free supernatant cancer cell media (Example 25), and the presence of SCM factor in cultured human cancer cells (Example 26).

Because of potential cross-reactivity of anti-SCM antibodies with α-1-PI because of the sequence homology between them, these immunodiagnostic tests are preferably carried out on body fluids from which α-1-PI molecules have been removed. The α-1-PI molecules can be removed by a number of techniques including, but not limited to, ultrafiltration through filters with nominal molecular weight cutoffs of 1,000 to 3,000 daltons, by passage through chromatographic columns, or by binding of α-1-PI to immobilized proteases such as trypsin, with which α-1-PI forms a stable complex.

2. Detection of Cancer Cells in Biopsies and Aspirates by Fluorescence Microscopy or Flow Cytometric Methods Anti-SCM antibodies labeled with fluorescent markers can be used for detection of cancer cells producing SCM in biopsies or aspirates by standard fluorescence microscopic and flow cytometric methods.

C. Detection of SCM-specific Receptors

It is believed that the effects of SCM factor on SCM-responding lymphocytes are mediated by the specific binding of SCM factor to SCM-factor-specific receptors located in the cell membrane of the lymphocytes. These receptors can be detected by the use of labeled SCM molecules, such as radiolabeled SCM factor, fluorescence-labeled SCM factor, enzyme-labeled SCM factor, or SCM factor labeled with a chemiluminescent label. Alternatively, SCM factor can be conjugated to biotin. Avidin or streptavidin can then be labeled with enzymes, fluorescent labels, or radioactive labels. The labeled avidin or streptavidin can be used to bind the biotin-conjugated SCM factor for labeling.

D. DNA Sequences and Vectors

1. Design and Synthesis of Oligonucleotide Sequences

The determination of amino acid sequences for both isolated and purified SCM factors, as well as the known amino acid sequence of the synthetic SCM factor, allows the construction of DNA oligonucleotide sequences corresponding to these amino acid sequences. The construction of these oligonucleotide sequences varies somewhat depending on whether their desired use is to be expressed in an in vitro expression system or to detect the natural gene or genes for SCM factor present in the DNA of the human genome. However, in either case, the oligonucleotides are synthesized according to well-known techniques, such as the phosphotriester method or the phosphite triester method, as described in K. Itakura, J. J. Rossi, & R. B. Wallace, "Synthesis and Use of Synthetic Oligonucleotides," *Annu. Rev. Biochem.* 53, 323 (1984).

a. Sequences for Expression

If the ultimate use of the sequence is to be for the production of genetically-engineered SCM factor by expression in an in vitro system, then it is only necessary to synthesize one DNA sequence corresponding to any particular amino acid sequence. However, the genetic code is degenerate, and the use of different codons for the same amino acid affects the rate of translation of the sequence in the host cell. It is desirable to select codons for those amino acids for which there is a choice according to the preferred codons for translation in the particular host organism from which the expression system used is derived. Because codon usage varies as between bacteria and eukaryotes, it is desirable to vary the exact sequence of the DNA according to the host in which the DNA sequence is to be expressed. The differences in codon usage between bacteria and mammals, including humans, are well-known in the art.

b. Sequences for Detection

If the synthesized DNA sequence is to be used to detect the natural genes for SCM factor in DNA, different considerations enter into the selection of the nucleotide sequence. To obtain accurate hybridization, it is frequently desirable to use a multiplicity of sequences so that all possible sequences corresponding to the desired amino acid sequence are present. As one possible example, the region between amino acids 14 and 22 is nearly invariant in the synthesized as well as in the purified SCM factors, being either F-L-M-I-D-Q-N-T-K or F-L-M-I-E-Q-N-T-K. If all possible codon combinations were used, however, there would be 2,304 27-nucleotide-long sequences that could correspond to these amino acid sequences. This number of different sequences is too great to handle efficiently in a hybridization reaction, so a possible compromise is to eliminate codons that are the least likely to be used in human DNA, according to R. Lathe, "Synthetic Oligonucleotide Probes Deduced from Amino Acid Sequence Data: Theoretical and Practical Considerations," *J. Mol. Biol.* 183, 1 (1985). For example, if the three codons least likely to be used are eliminated for leucine, the single least used codon eliminated for isoleucine, and the two least used codons eliminated for threonine, there would be a possible total of 384 separate 27-nucleotide-long sequences. This number of separate sequences has been used, for example, in R. B. Wallace, M. J. Johnson, T. Hirose, T. Miyake, E. H. Kawashima, and K. Itakura, "The Use of Synthetic Oligonucleotides as Hybridization Probes. II. Hybridization of Oligonucleotides of Mixed Sequence to Rabbit β-Globin DNA," *Nucl. Acids Res.* 9, 879–894 (1981).

2. Incorporation of DNA Sequences Into Vectors

Vectors for transfection or transformation contain the DNA sequence coding for the SCM factor and control sequences such as promoters and enhancers operatively linked to the coding sequences. The vectors also contain suitable replication sites. Both the control sequences and the replication sites are active in the intended host strain. When the host strain is the bacteria *Escherichia coli*, plasmids such as pBR322 are suitable vectors. When the host strain is a cultured mammalian cell such as a human cell, the vector is typically a virus such as SV40. Suitable host-vector systems are well-known in the art and are described, for example, in B. Perbal, "A Practical Guide to Molecular Cloning" (2d ed., John Wiley & Sons, 1988) and "Guide to Molecular Cloning Techniques" (S. L. Berger and A. R. Kimmel, eds., Academic Press, 1987; Volume 152 of *Methods in Enzymology*).

Techniques for incorporation of the desired sequences into the vectors by ligation, for transfection or transformation of the host cells with the ligated vectors, for propagation and selection of the host cells containing the vectors, and for the expression of the SCM factor coded for by the DNA sequences are all well-known in the art and are described in the Perbal or Berger & Kimmel references, supra.

IV. RELATIONSHIP BETWEEN THE SCM FACTOR AND CANCER

A. Protection of Cancer Cells in Vivo by SCM Factor

SCM factor molecules are now known to be synthesized by cancer cells. The SCM factor gene could be the result of genetic damage caused by chemical or viral agents, or it could be an oncogene whose normal counterpart is present in the cell. Like other known α-1-PI variants, the SCM factor gene or genes are likely derepressed by tumor-inducing agents and expressed when the mechanisms regulating cell division are activated by tumor promoters. Proteases and their inhibitors are closely implicated in the regulation of cell replication, division, maturation, and fertilization processes. A genetic defect causing production of a functionally abortive part of the α-1-PI molecule could contribute to the erratic and uncontrolled proliferation of initiated and promoted cancer cells. Our results suggest that SCM factor molecules can protect cancer cells and enhance their metastatic spread in several ways: stimulating DNA synthesis of cancer cells (Example 27), protecting the activity of cancer-cell-associated proteases (Example 28), and circumventing the immune surveillance and other anti-tumor responses of the host. One particular protective effect is the suppression of natural killer (NK) activity of lymphocytes by the SCM factor (Examples 13 and 31). Another possible protective effect is scavenging the reactive oxygen-containing species released by macrophages against cancer cells via the methionine residues incorporated in the SCM factor sequence.

Another indication of the common origin of α-1PI and the SCM factor, as well as the homology between them, is our discovery that a protein present in the 50 to 100 kilodalton molecular weight fraction of blood plasma in donors both having cancer and free of cancer can modify or abolish the SCM response to the SCM factor in the SCM-responding subpopulation of lymphocytes from cancer patients. This protein can also restore the SCM response to PHA in these cells. This SCM response modifying factor was originally designated as "plasma factor 2" (PF2). Incubation of SCM-responding lymphocytes from cancer patients for 2.5 hours in the presence of the 50 to 100 kilodalton molecular weight fraction of plasma from allogeneic or autologous donors removes, on subsequent washing of the lymphocytes, the receptors for cancer-associated factors, including SCM factor, and restores the ability of these lymphocytes to respond again to PHA. That is, the protein reverts the $RR_{SCM}$ from values typical of lymphocytes from donors with cancer (less than 1) to values typical of lymphocytes from donors free of cancer (greater than 1). PF2 protein, unexpectedly, is identical with α-1-PI (Example 29). The α-1-PI protein can reverse the SCM response of normal lymphocytes that have been treated with SCM factor, and can also reverse the SCM response of lymphocytes from donors afflicted with cancer.

B. Use of the SCM Factor in the Detection and Management of Cancer

As previously detailed in our patent application Ser. No. 07/167,007, the SCM factor of the present invention can be used for a number of purposes both in the detection and in the management of cancer.

1. Detection of Cancer a. Use of SCM Factor as Challenging Agent

SCM factor, or any of its active fragments, can be used as a challenging agent in the SCM test for the detection of cancer. Lymphocytes from donors with cancer, but not from donors free of cancer, are primed to respond to cancer-associated factors in the SCM test. Accordingly, only lymphocytes from donors with cancer respond to SCM factor with a decrease in intracellular fluorescein fluorescence polarization value in the SCM test. This response constitutes an early warning that cancer cells producing SCM factor are present in the body of the lymphocyte donor, even when the number of tumor cells or the size of the tumor might not be otherwise detectable.

b. Detection of Receptors Specific for SCM Factor

SCM factor molecules or fragments that are labeled can be used to detect the presence of receptors for SCM molecules on the SCM-responding fraction of lymphocytes. The label can be, but is not limited to, a radioactive label, a fluorescent label, a chemiluminescent label, or an enzyme label. The presence of these receptors is itself an indication of cancer. They can be detected using flow cytometry, fluorescence microscopy, enzyme-linked assays, or other assays for lymphocyte receptors. If the SCM molecules are labeled with radioactive isotopes, autoradiography, scintigraphy, and other detection methods for radionuclides can be used to detect the presence of receptors for SCM factors.

If SCM-responding lymphocytes are isolated, washed, and incubated with a saturating quantity of labeled SCM factor, the extent of the binding of the SCM factor to the lymphocytes indicates the number of SCM factor receptors present per lymphocyte. This test can be used to indicate the sensitization of SCM-responding lymphocytes to the SCM factor and can be used as an alternative to the SCM test to detect the presence of cancer; it can also be used to confirm the findings of the SCM test.

c. Detection of SCM Factor Molecules in Cancer Biopsies

By flow cytometry, fluorescence microscopy, or enzyme-linked assays, SCM factor molecules can be detected in cancer biopsies using appropriately labeled anti-SCM factor antibodies. Because SCM factor molecules are produced in quantity by cancer cells, their presence in biopsy specimens is a strong confirmation of the cancerous nature of the tissues from which the biopsy specimen is taken.

d. Detection of SCM Factor Molecules in Body Fluids

As shown above, SCM factor molecules are excreted by cancer cells into body fluids such as blood plasma or urine. The presence of SCM factor in body fluids can therefore be used as a general cancer-specific marker. The presence of SCM factor molecules can be detected in ultrafiltrates of cancer patients' blood plasma using antibodies against SCM factor in the immunoassays described above under "Immunoassays for SCM Factor"; either polyclonal or monoclonal antibodies of sufficient specificity can be used in the immunoassays. Antibodies to fragments of the SCM factor can substitute for antibodies to the entire SCM molecule in many applications.

As the production of SCM factor molecules by cancer cells is decreased by inhibitors of protein synthesis, the concentration levels of SCM factor in body fluids can be used to indicate the metabolic activity of any remaining cancer cells following treatments, and to detect the recurrent growth of cancer or the presence of otherwise occult metastases. The presence of SCM molecules could in addition serve as a warning that cancer cells present in the body of the patient are likely to metastasize.

2. Treatment of Cancer

As detailed above, the SCM factor protects cancer cells against normal defense mechanisms and promotes their growth and spread. The mechanism by which the SCM factor accomplishes this includes, but is not limited to, protection of cancer cells from the action of natural killer (NK) cells (Examples 13 and 31). This effect of SCM factor leads to the idea that measures that selectively decrease the in vivo activity of the SCM factor can be useful in the management of cancer.

As a first step of such methods, once lymphocytes from a known or suspected cancer patient have been shown to give a positive response in the SCM test with the SCM factor of the present invention as a challenging agent, a sample of a body fluid can be taken from the patient, passed through an ultrafilter with a nominal molecular weight cutoff of 1,000 daltons, and the fraction passing through the ultrafilter collected and used as an autologous cancer factor to challenge lymphocytes from the same patient in the SCM test to confirm the presence of the SCM factor in the fraction. It need not always be necessary to perform this confirmatory test, particularly if other clinical indicators indicate the presence of cancer.

a. Inactivation of SCM Factor in Body Fluids

Once the presence of SCM factor in a body fluid of a cancer patient is shown or inferred, the body fluid can be treated by one of several methods to reduce the in vivo effect of the factor by inhibiting its production, selectively removing it, or selectively inactivating it, and the body fluid can then be returned to the patient, thereby enhancing the resistance of the patient to the malignancy. Since the SCM factor of the present invention causes a response in the SCM test regardless of the type of cancer afflicting the patient, it is believed that reducing the in vivo effect of the SCM factor can enhance the resistance of the patient not only to the particular type of cancer originally diagnosed, but also to any other type of malignancy that might subsequently develop in the patient. This can prove significant when treating patients with drugs that have an immunosuppressant effect, or patients with an already compromised immune system due to conditions such as AIDS.

(1) Inactivation by Dialysis

When the body fluid is peripheral blood, one method of reducing the in vivo activity of the SCM factor is to physically remove it by dialysis of the peripheral blood to remove peptides with an apparent molecular weight of 1,000 daltons or less, since the factor will pass through ultrafilters with a nominal molecular weight cutoff of 1,000 daltons or less, even though its actual molecular weight is somewhat greater.

(2) Inactivation by Reaction with Antibodies or Antisense Peptides

Another method of reducing the in vivo activity of the SCM factor in a body fluid is to neutralize it or inactivate it with antibodies specific for the factor. The antibody is prepared as described above and can be polyclonal or monoclonal. Alternatively, monovalent antibody fragments, such as Fab fragments or Fab' fragments, can be used. Use of monovalent fragments can be preferable to use of intact antibody in some applications if the formation of large SCM factor-antibody complexes is considered undesirable. The presence of such large antigen-antibody complexes in the peripheral blood can possibly cause serum sickness and other allergic reactions.

As an alternative to the use of antibodies, antisense peptides encoded by the antisense strand of the DNA whose sense strand encoding for SCM factor can also be used to inhibit the activity of SCM factor. As reported in Y. Shai, T. K. Brunck, & I. M. Chaiken, "Antisense Peptide Recognition of Sense Peptides: Sequence Simplification and Evaluation of Forces Underlying the Interaction," *Biochemistry* 28, 8804–8811 (1989), and G. Fassina, M. Zamai, M. Brigham-Burke, & I. M. Chaiken, "Recognition Properties of Antisense Peptides to Arga-vasopressin/Bovine Neurophysin II Biosynthetic Precursor Sequences," *Biochemistry* 28, 8811–8818 (1989), peptides that are encoded by the antisense strand of a DNA molecule whose sense strand encodes a physiologically active peptide often interact specifically with that peptide. The "sense strand" is the strand of the DNA identical in sequence with the messenger RNA corresponding to it (except for the substitution of U in mRNA for T in DNA), while the "antisense strand" is complementary to the sequence of the mRNA. For example, if the sense strand has the sequence ATG, the antisense strand would have the sequence CAT.

As applied to inhibition of SCM factor, the antisense peptide has an amino acid sequence encoded by the antisense strand of a DNA sequence whose sense strand encodes a cancer recognition factor of at least 9 amino acid residues including a core sequence of 9 amino acid residues having an amphipathicity profile substantially equivalent to the sequence F-L-M-I-D-Q-N-T-K. Typically, the cancer recognition factor has the amino acid sequence F-L-M-I-D-Q-N-T-K, corresponding to residues 14–22 of the synthetic SCM factor molecule, or the sequence M-I-P-P-E-V-K-F-N-K-P-F-V-F-L-M-I-D-Q-N-T-K-V-P-L-F-M-G-K, corresponding to the entire synthetic SCM molecule.

b. Tagging Anti-SCM Factor Antibody with Anti-cancer Substances

Because SCM factor is produced by actively metabolizing cancer cells (Examples 25 and 26), an antibody specific for the SCM factor can be used to target an anti-cancer substance to such cells by labeling anti-SCM factor antibody with the anti-cancer substance. This directs the anti-cancer substance to the site of the cancer and thereby raises the effective concentration of the anti-cancer substance at the site of the cancer. This procedure can be especially advantageous when the anti-cancer substance is one that produces side effects when given in larger doses. Such labeling can be performed by standard conjugation procedures used for conjugating enzymes, fluorescent labels, or radioactive labels to antibodies as described in P. Tijssen, "Practice and Theory of Enzyme Immunoassays," (Elsevier, Amsterdam, 1985), pages 221–278.

c. Use of Non-homologous Protease Inhibitors

Effective control of the proliferation and invasive spread of cancer cells enhanced by SCM factor might be achieved by inhibition of the proteases that are protected against natural inhibitors by the SCM factor by using natural inhibitors that are non-homologous with the SCM factor but of the same small size and ease of diffusion. Preferably, the inhibitor is non-homologous with any other protease inhibitor that is substantially inhibited by SCM factor. Examples include the synthetic variant of *Cucurbita maxima* trypsin inhibitor, a 29-residue peptide. Such natural or synthetic protease inhibitors should be selected for their ability to overcome the protective effect of the SCM factor. Screening of such potential protease inhibitors should therefore be carried out on proteases protected by the SCM factor, either by the entire SCM factor or by the portion of the molecule active in inhibition of α-1-PI, the aminoterminal seven residues. We suggest that the use of such protease inhibitors non-homologous with α-1-PI and capable of inhibiting proteases in the presence of SCM factor could be used for cancer treatment. The simultaneous removal of SCM factor from blood plasma by dialysis might help to diminish its effect on the patients' defense mechanisms.

d. Use of Inhibitors of Protein Synthesis to Inhibit SCM Factor Formation

Because SCM factor is the result of active protein synthesis by cancer cells, new synthesis of SCM factor can be decreased by treatment with suitable clinically acceptable non-toxic inhibitors of protein synthesis that causes a decrease in production of SCM factor by tumor cells, such as cycloheximide or ascorbic acid. We have previously demonstrated that ascorbic acid can selectively induce the transition of mitochondria into the idling, orthodox conformation in cancer cells, thereby decreasing their metabolic activity. Example 30 shows the effect of ascorbic acid on the synthesis of SCM factor in MCF7 human breast cancer cells in culture. Addition of $10^{-3}$M ascorbate decreased the synthesis of SCM factor in these cells considerably as measured by the ELISA procedure using anti-SCM antibodies. The use of ascorbic acid or other protein synthesis inhibitors is therefore proposed as a cancer-specific, non-toxic inhibitor of SCM factor synthesis. It could be used on its own or in conjunction with other methods of removing or inactivating SCM factor.

e. Reversing NK-Suppressive Action of SCM Factor

Because the NK-suppressive activity of SCM factor is believed to protect cancer cells from natural defenses, one way of restoring the effectiveness of those defenses is by reversing the NK-suppressive effect of SCM factor. Such a method can comprise administering to a patient at least one of whose body fluids contains SCM factor a SCM-factor-inhibiting substance in a quantity sufficient to substantially reverse the NK-suppressive action of the SCM factor and substantially restore normal NK activity of lymphocytes of the patient as measured by in vitro lysis of K562 cells by the lymphocytes. The SCM-factor-inhibiting substance can be antibodies to SCM factor, univalent antigen-binding fragments of antibodies to SCM factor, or antisense peptides whose amino acid sequences are those encoded by the antisense strand of DNA sequences whose sense strand encodes a NK-suppressive peptide sequence.

3. Use of Anti-SCM-factor Antibodies to Image Cancer Cells

Because the SCM factor is produced by cancer cells and is found in association with them, anti-SCM-factor antibodies can also be used to image cancer cells by labeling the antibodies with imaging substances such as fluorescent dyes or radioactive isotopes. Such labeled antibodies can be used to detect cancer cells in biopsies by fluorescence microscopy or autoradiography. Fluorescent-labeled antibody can also be used for automated detection of cancer cells by flow cytometry.

4. Use of SCM Factor to Modulate Immune System Activity

Because the SCM factor is capable of inhibiting the NK activity of lymphocytes (see Examples 13 and 31), it can be used to modulate immune system activity and assess the effectiveness of anti-cancer drugs. Example 31 shows that the NK-suppressive activity of SCM factor is present only in the entire synthetic SCM factor molecule (29 amino acids) and fragment F2 (amino acids 8–29 of synthetic SCM factor). Peptides derived from fragment F2 but incorporating one or more conservative amino acid substitutions are also expected to have NK-suppressive activity.

Such peptides having NK-suppressive activity can be used in a method for assessing the effectiveness of an anti-cancer agent capable of inhibiting the growth of malignant cells in a cell culture. The cell culture includes both lymphocytes exhibiting NK activity and malignant cells. The method comprises the steps of: (1) incubating the cell culture with a substantially purified NK-suppressive peptide in a quantity sufficient to substantially suppress the NK activity of the lymphocytes of the cell culture; (2) adding the anti-cancer agent to the cell culture in a quantity sufficient to inhibit the growth of the malignant cells; and (3) determining the effect of the anti-cancer agent on the malignant cells by measuring the inhibition of growth of the malignant cells in the essential absence of NK activity of the lymphocytes.

Such NK-suppressive peptides can also be used in a method of suppressing the NK activity of lymphocytes. The method comprises administering to the lymphocytes a substantially purified NK-suppressive peptide in a quantity sufficient to substantially suppress the NK activity of the lymphocytes as measured by a standard test for NK activity. Such a standard test is the in vitro lysis of K562 cells. This method of suppressing NK activity can be useful when it is desired to modulate immune system activity. A clinical example in which such modulation is desirable is the transfusion of blood into patients who have just undergone a tissue transplant and are at risk of rejection of the transplant; the lymphocytes of such blood can be treated with the NK-suppressive peptide to diminish the risk of such transplant rejection.

Similarly, a substantially purified SCM factor or NK-suppressive peptide can be used as an immunosuppressive drug. The method of use comprises administering an immunosuppressive fraction alone or in combination with a pharmaceutically acceptable carrier in a quantity sufficient to create a degree of immunosuppression capable of enhancing allograft survival. The immunosuppressive fraction can be a substantially purified naturally occurring SCM factor, the 29-amino-acid synthetic SCM factor, or a NK-suppressive peptide that includes at least residues 8-29 of the synthetic SCM factor or is derived from that sequence by the occurrence of conservative amino acid substitutions.

EXAMPLES

The following Examples illustrate: (1) the isolation, purification, characterization, and activities of substantially purified SCM factor from body fluids of patients with cancer and (2) the characterization and activities of synthetic SCM factor and peptides comprising partial sequences of synthetic SCM factor. These Examples are for illustrative purposes only and are not to be construed as limiting the invention.

Example 1

Initial Purification of the General Cancer-Associated SCM Factor from Blood Plasma Blood samples from patients positively diagnosed as having active cancer, such as cancer of the breast, lung, colon, ovary, cervix, uterus, larynx, or skin (basal cell carcinoma and malignant melanoma) were collected into heparinized vials such as Vacutainer TM tubes. Twenty-milliliter portions of the blood samples were centrifuged at about 1200×g for approximately 40 min. The plasma above the sedimented blood cells was collected and filtered by pressure through a porous membrane filter such as an Amicon UM2 or YM2 filter, with a 1000-dalton molecular weight cutoff. These ultrafiltrates were lyophilized or stored at 4° C. until further purification.

Example 2

SCM Activity of Initially Purified SCM Factor from Example 1

Aliquots of the ultrafiltrate from each sample of Example 1 were incubated with potentially SCM-responding lymphocytes obtained from the same donors and the lymphocytes checked for their SCM response in accordance with the SCM test procedure described above. In every case the ultrafiltrate caused the SCM-responding lymphocytes to respond characteristically with a decrease in P value, as they would have if they had been contacted with the cancerous tissue itself or with extracts of cancerous tissue (Table 1). As used throughout, "Ca" designates "cancer."

TABLE 1

| SCM ACTIVITY OF ULTRAFILTRATES OF EXAMPLE 1 | | |
| --- | --- | --- |
| Diagnosis of Lymphocyte Donor | Diagnosis of SCM Factor Donor | SCM Response: P Value as % of Control |
| Malignant Melanoma | Malignant Melanoma | 75.7 |
| Malignant Melanoma | Basal Cell Carcinoma-Skin | 82.0 |
| Ca-Larynx | Ca-Larynx | 62.9 |
| Ca-Breast | Ca-Breast | 76.0 |

The data of Table 1 show that even when present in the crude ultrafiltrate, the SCM factor caused a decrease in the P value of the SCM-responding lymphocytes from donors afflicted with cancer at least equivalent to the decrease of the P values observed when lymphocytes are stimulated by crude extracts of cancerous tissues or cancerous tissues themselves. The decrease in P value on stimulation by the ultrafiltrates was at least 10%, which is characteristic of such a positive SCM response. However, the SCM factor did not pass through the Amicon TM UM05 filter with a nominal 500-dalton molecular weight cutoff. These data confirm the small size of the factor while indicating that the activity is larger than a small molecule such as a single amino acid.

Example 3

Further Purification of the SCM Factor of Example 1

The lyophilized powder from the samples of Example 1 was dissolved in 2 ml of sterile preservative-free water for injections. At this stage, the SCM activity of the preparations was ascertained, and active samples from donors with the same type and site of cancer were pooled. The pooled samples were desalted on an 0.9×18 cm column of Sephadex TM G-10, which has a fractionation range of from 0 to 700 daltons. The sample volume per column chromatographic run did not exceed 25% of the column volume. Elution was carried out with double distilled water at the linear elution speed of 8 to 9 cm/hr. The desalting was carried out at room temperature (21°-23° C.). One-ml fractions eluting at between 0.3 and 0.5 times the total chromatographic bed volume were collected and the optical densities of the fractions determined. The SCM activity was contained within the first elution peak. The presence of SCM activity in that peak was confirmed by an SCM test. An aliquot of the first elution peak, prepared from an ultrafiltrate originally derived from plasma of a patient with breast cancer, reduced the P value of lymphocytes from a patient with breast cancer to 86.3% of the control value in the SCM test, indicating the presence of SCM activity. These fractions were collected and lyophilized.

The eluate was further purified by fractionation on a Sephadex ™ G-50 gel filtration column, which has a fractionation range of from 1500 to 30,000 daltons. The lyophilized desalted samples were dissolved in 50 mM $NH_4HCO_3$, loaded at no more than 5% of the column volume on a 0.9×18 cm Sephadex G-50 column at the linear elution speed of 3 cm/hr. The elution was carried out at room temperature, and one-milliliter fractions eluting from the column at between 0.4 and 0.6 times the total chromatographic bed volume were collected. These fractions were tested for SCM activity. Results of these tests are given below in Example 4. The SCM-active fractions were contained within the first elution peak as determined by optical densities of the one-milliliter fractions after testing of the fractions in the SCM test.

Once the fractions were tested for SCM activity, the active fractions from the same cancer types were pooled and lyophilized.

For further purification the lyophilized samples were dissolved in 10 mM $NH_4HCO_3$ and loaded at no more than 4% of the column volume on an 0.8×26 cm column of Whatman DE-52 microgranular DEAE-cellulose. The column was washed with 10 ml of 10 mM aqueous $NH_4HCO_3$ increasing by 0.108% per minute from 10 mM to 1M $NH_4HCO_3$. One-milliliter fractions were collected and the optical absorption at 220 nm was determined for each fraction. Based on the optical absorbance, active fractions eluting from the column at between 4.5 and 4.7 times the total chromatographic bed volume were pooled and lyophilized for testing and further purification. Results from SCM testing of the active fractions are given in Example 4.

Example 4

SCM Activity of Further Purified Preparations of Example 3

Table 2 shows the results when aliquots of the Sephadex G-50 fractions from Example 3 originally from donors with various types of cancer were used to challenge lymphocytes from donors, also with various types of cancer, in the SCM test. It can be seen that potentially SCM-responding lymphocytes have the same characteristic response to the G-50 fractions as they did to the previously characterized cancer-associated antigens. This desalted partially purified proteinaceous material exhibits a generally increased SCM response as compared to the crude ultrafiltrate for which the results were shown in Table 1. This increased SCM response is shown by decreased P values.

TABLE 2

| SCM ACTIVITY OF SEPHADEX G-50 FRACTIONS OF EXAMPLE 3 | | |
|---|---|---|
| Diagnosis of Lymphocyte Donor | Diagnosis of SCM Factor Donor | SCM Response: P Value as % of Control |
| Ca-Lung | Ca-Breast | 73.0 |
| Ca-Lung | Ca-Cervix | 69.6 |
| Ca-Lung | Ca-Bronchus | 73.6 |
| Ca-Larynx | Ca-Bronchus | 77.6 |
| Ca-Breast | Ca-Bronchus | 80.2 |

TABLE 2-continued

| SCM ACTIVITY OF SEPHADEX G-50 FRACTIONS OF EXAMPLE 3 | | |
|---|---|---|
| Diagnosis of Lymphocyte Donor | Diagnosis of SCM Factor Donor | SCM Response: P Value as % of Control |
| Ca-Colon | Ca-Breast | 63.5 |
| Ca-Larynx | Ca-Breast | 63.0 |
| Malignant Melanoma | Malignant Melanoma | 74.9 |
| Healthy Donor | Malignant Melanoma | 99.3 |
| Healthy Donor | Ca-Colon | 98.0 |
| Colitis | Ca-Colon | 98.9 |

Table 3 shows the results when SCM factor obtained from donors with various types of malignancies after purification through the DEAE-cellulose stage was used to challenge lymphocytes isolated either from donors with various types of malignancies or from donors free of malignancy in the SCM test. As expected, the lymphocytes from cancer patients responded to the SCM factors purified from the DEAE-cellulose columns with a considerable decrease in P value, while lymphocytes from donors free of malignant disease showed no such decrease in P value.

TABLE 3

| SCM ACTIVITY OF DEAE-CELLULOSE FRACTIONS OF EXAMPLE 3 | | |
|---|---|---|
| Diagnosis of Lymphocyte Donor | Diagnosis of SCM Factor Donor | SCM Response: P Value as % of Control |
| Ca-Breast | Ca-Breast | 69.2 |
| Ca-Breast | Ca-Bronchus | 69.5 |
| Ca-Breast | Ca-Cervix | 69.0 |
| Basal Cell Carcinoma-Skin | Basal Cell Carcinoma-Skin | 82.0 |
| Healthy Donor | Ca-Colon | 98.6 |
| Cholecystitis | Malignant Melanoma | 100.0 |
| Urethritis | Ca-Cervix | 99.8 |
| Appendicitis | Ca-Colon | 98.0 |
| Benign Breast Growth | Ca-Breast | 97.8 |
| Benign Pituitary Adenoma | Ca-Brain | 100.0 |

Example 5

Final Purification of SCM Factor of Example 3 by RP-HPLC

The DE-52 general cancer-associated SCM-active fractions of Example 4 were then reconstituted and purified to homogeneity by reverse phase high pressure liquid chromatography (RP-HPLC) using a 2.1 mm×22 cm HPLC column. The column was packed with Aquapore RP-300 ™ (7 microns). The mobile phases used in the RP-HPLC purification step were as follows:

Phase A: 0.1 volume percent aqueous trifluoroacetic acid (TFA).

Phase B: 0.09 volume percent aqueous TFA in aqueous 70% acetonitrile.

Lyophilized DE-52 SCM-active fractions were reconstituted with sterile water for injections (without preservatives) and 250 microliter aliquots were injected into the RP-HPLC column. The mobile phase flow rate was 50 microliters per minute and its composition profile was 10 minutes of 90 volume percent of Phase A, 10 volume percent of Phase B, followed by 30 minutes of linear increase of Phase B at the rate of 3 volume percent per minute. The optical density peaks detected by optical absorbance at 220 nm were hand-collected via a "nanobore" teflon tubing into 1.5 ml plastic conical Eppendorf centrifuge tubes and the solvent was evaporated in a vacuum centrifuge. In all cases, the general cancer-associated SCM-recognition factor eluted from the column at 74 volume percent of Phase B.

Example 6

Alternative RP-HPLC Purification of SCM Factor

Alternatively, the SCM factor can be purified by performing HPLC using a 4.6 mm×25 cm HPLC column packed with ULTRASPHERE® ODS=(5 microns) distributed by Beckman Instruments, Inc. with the DEAE-52 SCM-active fractions of Example 4. The mobile phases used with this column were as follows:

Phase A: 0.1 volume percent aqueous trifluoroacetic acid (TFA).

Phase B: 0.1 volume percent TFA in aqueous 70% acetonitrile.

The same general procedure was followed with this column as for the Aquapore column, except that the mobile phase flow rate was 1.00 ml per minute and its composition profile was 5 minutes of 70 volume percent of Phase A, 30 volume percent of Phase B, followed by 20 minutes of linear increase of Phase B at the rate of 3.5 volume percent per minute. The optical density peaks were detected at 220 nm and were hand-collected into siliconized glass test tubes and the solvent was evaporated in a vacuum centrifuge. When this HPLC system was used, in all cases the purification of general cancer-associated SCM-recognition factor from nineteen different cancer types, including squamous cell carcinoma of the cervix, adenocarcinoma of the breast, adenocarcinoma of the bronchus, and malignant melanoma, always yielded a single optical density peak of activity, eluting at 56.3 volume percent of Phase B.

Example 7

SCM Activity of RP-HPLC Purified Preparations of Example 6

For SCM activity testing, of the peptides isolated by RP-HPLC on the ULTRASPHERE® column in Example 6, the peptides were reconstituted with sterile water for injections without preservatives. The SCM activity of SCM-responding lymphocytes after incubation with these samples is shown in Table 4. This fraction gives the greatest decrease in polarization value when used to challenge lymphocytes from donors afflicted with cancer. Two of the three preparations of SCM factor gave a decrease in polarization value greater than 40%, a larger decrease than seen with any other fraction tested. The purified factor, as expected, was non-specific with respect to the type of cancer afflicting the donor of the lymphocytes used. Also as expected, the purified factor gave no response when used to challenge lymphocytes from healthy donors.

TABLE 4

SCM ACTIVITY OF RP-HPLC FRACTIONS OF EXAMPLE 6

| Diagnosis of Lymphocyte Donor | Diagnosis of SCM Factor Donor | SCM Response: P Value as % of Control |
|---|---|---|
| Ca-Breast | Ca-Breast | 58.9 |
| Ca-Breast | Ca-Lung | 57.3 |
| Ca-Colon | Ca-Breast | 55.4 |
| Ca-Breast | Ca-Bronchus | 68.0 |
| Healthy Donor | Ca-Breast | 99.8 |

TABLE 4-continued

SCM ACTIVITY OF RP-HPLC FRACTIONS OF EXAMPLE 6

| Diagnosis of Lymphocyte Donor | Diagnosis of SCM Factor Donor | SCM Response: P Value as % of Control |
|---|---|---|
| Healthy Donor | Ca-Lung | 101.0 |

Example 8

Identification and Isolation of SCM-Active Tryptic Peptides from SCM Factor Purified from Blood Plasma of Patients with Breast Cancer and Lung Cancer Tryptic peptides with SCM activity were isolated from the purified SCM factors isolated from blood plasma of patients with breast cancer or lung cancer. The cleavage of the purified factors with trypsin and purification of the active fragments were carried out by the following procedure:

To prevent adsorption loss of the peptide during lyophilization, the SCM factor was digested with trypsin in the presence of HPLC eluants. Trypsin digestion was carried out in 0.1M Tris-HCl buffer, pH 8.3, at 37° C. for 24 hours using 10 percent by weight of trypsin. The digest was diluted fourfold with 0.1 volume percent aqueous trifluoroacetic acid, and was injected into an Applied Biosystems 130A microflow HPLC-separation system. The tryptic fragments were separated using an Aquapore RP-300 column (200 mm×2.1 mm). For the elution of the fragments, the mobile phase solvents were:

Phase A: 0.1 volume percent aqueous trifluoroacetic acid (TFA).

Phase B: 0.09 volume percent TFA in aqueous 70% acetonitrile.

The mobile phase flow rate was 50 μl per minute and the composition profile was 10 minutes of 96 volume percent Phase A, 4 volume percent Phase B, followed by a linear elution gradient comprising a 30 min linear increase in Phase B at a 3 volume percent per minute rate. The SCM-active tryptic peptide fragment eluted at 69.6 volume percent of Phase B and 30.4 volume percent of Phase A in a total volume of about 30 microliters.

The tryptic peptide cleaved from the SCM factor purified from patients with lung cancer was tested for SCM activity in Example 10, below, and found to be fully active. By comparison with the sequences of the entire isolated SCM factors determined in Example 14, these tryptic peptides were found to represent amino acids 8–22 of the SCM factor molecule.

Example 9

Use of the Isolated SCM Factor as the Challenging Agent in the SCM Test

Table 5 summarizes the results obtained by using preparations of the general cancer-associated SCM recognition factor at various stages of purification from Examples 1, 3, and 6 as the challenging agent in the SCM test. When lymphocytes from donors afflicted with a number of different malignancies were used with the factor of the present invention in the SCM test, a significant response was seen in all cases. This response is given in Table 5 as a percent of the control polarization value obtained by performing the SCM measurement on the same lymphocytes unincubated with the factor. The smaller the value the greater the response to the factor in the SCM test. Even the crudest preparation of the factor tested, the ultrafiltrate, give a decrease in polarization value of from 18.0% to 37.1%, and the most highly purified fraction, purified by RP-HPLC, gave a decrease in polarization value of as great as 44.6%. The factor of the present invention is specific and only causes a decrease in polarization value when used to challenge lymphocytes from donors afflicted with cancer. Even the RP-HPLC purified fraction caused no decrease in polarization value when used to challenge lymphocytes from healthy donors.

TABLE 5
EXAMPLES OF SCM ACTIVITY AT DIFFERENT PURIFICATION STAGES (EXAMPLE 9)

| Stage of Purification | Range of Percentage Decrease In P Value When Lymphocytes From Cancer Patients Used |
|---|---|
| Ultrafiltrate of Plasma (1000-dalton Cutoff) | 18.0–37.1 |
| Sephadex G-50 Fraction | 19.8–37.0 |
| DE-52 Cellulose Fraction | 18.0–31.0 |
| RP-HPLC Fraction | 32.0–44.6 |

No fraction showed any activity when tested against lymphocytes from healthy donors, or from donors with non-malignant diseases.

Example 10

Activity of the Tryptic Peptide of Example 8 in the SCM Test

The tryptic peptide obtained from SCM factor from plasma of patients with lung cancer, whose purification was described above in Example 8, was fully active in the standard SCM test.

Approximately $5 \times 10^{-2}$ femtograms of this fragment (i.e., $5 \times 10^{-17}$ grams, or approximately 16,000 molecules of the fragment) gave full activity in the test. When the fragment was isolated from patients with lung cancer, it proved active in the SCM test when tested against lymphocytes from a patient with small cell lung carcinoma, and crossreacted fully with lymphocytes from a patient with adenocarcinoma of the breast, as shown in Table 6. However, no response was seen when lymphocytes from healthy donors were used.

TABLE 6
SCM ACTIVITY OF TRYPTIC FRAGMENT OF EXAMPLE 8 FROM LUNG CANCER

| Diagnosis of Lymphocyte Donor | SCM Response: P Value as Percent of Control | |
|---|---|---|
| Small Cell Lung Carcinoma | 70.0 | 68.0 |
| Adenocarcinoma of Breast | 67.5 | 68.0 |
| Healthy Donors | 102.0 | 104.0 |

Example 11

Cross-Reactivity of Isolated SCM Factors

The following example demonstrates the ability of the isolated SCM factor to cause a response in the SCM test when used to challenge lymphocytes derived from donors afflicted with dissimilar types of cancer. In order to demonstrate this cross-reactivity, two milliliters of cell-free blood plasma was obtained from each of a number of blood samples from cancer patients. The blood samples had originally been collected into heparinized Vacutainer ™ tubes. The samples were ultrafiltered through an Amicon ™ UM2 or YM2 filter with a nominal molecular weight cutoff of 1000 daltons for at least 12 hr and stored under sterile conditions at 4° C.. Potentially SCM-responding lymphocytes were isolated from heparinized blood samples from patients with cancer, healthy donors, and donors with non-malignant diseases. To test the activity and cancer specificity of the general cancer-associated SCM-recognition factor containing ultrafiltrates, 0.75 ml aliquots of potentially SCM-responding lymphocytes ($5 \times 10^6$ cells/ml in PBS) were incubated for 40 min at 37° C. with the ultrafiltrates. 0.075 ml of the ultrafiltrates was used for each assay. SCM measurements were carried out as previously described in the article by L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977) and in the prior patent application by B. Cercek and L. Cercek, Ser. No. 867,079, filed May 27, 1986, and entitled "Method for Measuring Polarized Fluorescence Emissions." In the SCM assay, a decrease in the intracellular fluorescence polarization value (P value) of at least 10% was taken as a positive response to the challenging ultrafiltrate.

TABLE 7
CROSSREACTIVITY OF SCM ACTIVITY OF ULTRAFILTRATES OF EXAMPLE 11

| Diagnosis of Donor of Ultrafiltrate | Cases Responding/Cases Tested for Lymphocyte Donor with Diagnosis of: | | | | | | | | | |
|---|---|---|---|---|---|---|---|---|---|---|
| | Ca-Mouth | Ca-Larynx | Ca-Cervix | Ca-Ovary | Ca-Lung | Ca-Brain | Ca-Breast | Ca-Colon | Non-Cancer Diseases | Healthy Donors |
| Ca-Lung | — | 2/2 | 3/3 | — | 5/5 | 3/3 | 3/3 | 2/2 | 0/3 | 0/3 |
| Ca-Bronchus | 1/1 | 1/1 | 2/2 | 2/2 | 2/2 | — | 2/2 | 1/1 | — | 0/2 |
| Ca-Breast | 1/1 | 1/1 | 3/3 | 2/2 | 2/2 | — | 3/3 | 1/1 | 0/3 | 0/2 |
| Ca-Ovary | 1/1 | 2/2 | 2/2 | 3/3 | 2/2 | — | 2/2 | — | 0/4 | 0/2 |
| Ca-Cervix | 1/1 | 1/1 | 5/5 | 1/1 | 2/2 | — | 2/2 | 2/2 | 0/3 | 0/3 |
| Ca-Colon | 2/2 | — | 3/3 | — | 2/2 | — | 2/2 | 1/1 | 0/2 | 0/2 |
| Ca-Mouth | 2/2 | — | 1/1 | — | 1/1 | — | 1/1 | 1/1 | — | 0/2 |
| Ca-Larynx | 1/1 | 6/6 | 3/3 | — | 2/2 | — | 2/2 | 1/1 | 0/2 | — |
| Malignant Melanoma | — | — | — | — | — | — | 1/1 | 1/1 | — | 0/2 |
| Glioblastoma | — | — | 2/2 | — | — | 2/2 | 2/2 | 1/1 | 0/2 | 0/2 |
| Appendicitis | — | — | — | — | 0/1 | — | 0/1 | 0/3 | 0/3 | 0/2 |
| Urethritis | — | — | 0/2 | — | 0/2 | — | 0/1 | 0/2 | 0/3 | 0/3 |
| Infectious Abscess | — | 0/1 | 0/1 | — | — | — | 0/1 | 0/1 | 0/2 | 0/2 |
| Colitis | — | — | 0/1 | — | — | — | 0/1 | 0/3 | 0/2 | 0/2 |
| Benign Pituitary Adenoma | — | — | — | — | 0/2 | 0/2 | 0/2 | — | 0/1 | 0/1 |

TABLE 7-continued

CROSSREACTIVITY OF SCM ACTIVITY OF ULTRAFILTRATES OF EXAMPLE 11

| Diagnosis of Donor of Ultrafiltrate | Cases Responding/Cases Tested for Lymphocyte Donor with Diagnosis of: | | | | | | | | | |
|---|---|---|---|---|---|---|---|---|---|---|
| | Ca-Mouth | Ca-Larynx | Ca-Cervix | Ca-Ovary | Ca-Lung | Ca-Brain | Ca-Breast | Ca-Colon | Non-Cancer Diseases | Healthy Donors |
| Healthy Donors | — | — | 0/2 | 0/1 | 0/3 | — | 0/3 | 0/1 | 0/4 | 0/6 |

As the data of Table 7 show, potentially SCM-responding lymphocytes from patients with eight different cancer types responded to ultrafiltrates containing general cancer-associated SCM-recognition factors from nine different cancer types. In contrast, ultrafiltrates from plasmas of healthy donors and donors with non-cancer diseases did not trigger any positive SCM responses. Also, neither did the potentially SCM-responding lymphocytes from healthy donors or those with non-malignant conditions respond to any of the ultrafiltrates in the SCM test.

Example 12

Modification of the SCM Response by the Isolated SCM Factor

To demonstrate the modification of the SCM response of lymphocytes free of malignancy by incubation with the isolated SCM factor, potentially SCM-responding lymphocytes were isolated from the blood samples of healthy donors and suspended in complete Dulbecco's phosphate buffered saline (PBS) at $5 \times 10^5$ cells/ml as described in the *European Journal of Cancer* article, supra, and also in the prior patent application by B. Cercek, Ser. No. 838,264, filed Mar. 10, 1986, and entitled "Automated Collection of Buoyant Density Specific Cells from Density Gradients." Aliquots of these cells were incubated in 3 ml of the following: (a) cell-free blood plasma from cancer patients; (b) plasma from cancer patients ultrafiltered for 12 hours through an Amicon™ UM2 filter with a molecular weight cutoff of 1000 daltons; (c) plasma from cancer patients ultrafiltered for 12 hours through an Amicon™ UM5 filter with a nominal molecular weight cutoff of 500 daltons; (d) general cancer-associated SCM factor as purified through the desalting or Sephadex G-10 column stage; (e) the factor as purified through the Sephadex G-50 column stage; (f) the factor as purified through the DEAE-cellulose column step; (g) the factor as finally purified through the RP-HPLC step; and (h) plasma from healthy donors ultrafiltered through an Amicon™ UM2 filter with a nominal molecular weight cutoff of 1000 daltons. These incubations were performed for 2.5 hr.

The ability of the SCM factor to modify the SCM response of the lymphocytes from healthy donors was demonstrated by determining the SCM response ratio ($RR_{SCM}$) of the lymphocytes before and after the incubation with each of the fractions described above. Before being contacted with either a mitogen or with the SCM factor for determination of the $RR_{SCM}$ the incubated cells were thoroughly washed. The presence or absence of modification was determined by the ratio of the polarization value of the lymphocyte suspension after a short contact period with substrates containing the SCM factor over the polarization value of the lymphocyte suspension after a short contact period with phytohaemagglutinin (PHA). In accordance with the SCM test procedure, a $RR_{SCM}$ of less than 1.0 is a positive indication of the presence of malignancy in the donor while an $RR_{SCM}$ of 1.1 or greater indicates the absence of malignancy.

TABLE 8

MODULATION OF SCM RESPONSES OF LYMPHOCYTES FROM HEALTHY DONORS BY SCM FACTOR (EXAMPLE 12)

| SCM Preparation Used For Modulation | $RR_{SCM}$: Before Modulation | After Modulation |
|---|---|---|
| Cell-free Cancer Blood Plasma | 1.38 | 0.80 |
| Ultrafiltrate of Cancer Blood Plasma (1000 Daltons Cutoff) | 1.35 | 0.78 |
| Sephadex G-10 (SCM-Active) | 1.40 | 0.80 |
| Sephadex G-50 (SCM-Active) | 1.38 | 0.73 |
| DEAE-Cellulose (SCM-Active) | 1.39 | 0.70 |
| RP-HPLC (SCM-Active) | 1.40 | 0.65 |
| Ultrafiltrate of Cancer Blood Plasma (500 Daltons Cutoff) | 1.38 | 1.38 |
| Ultrafiltrate from Autologous and Allogenic Blood Plasma from Healthy Donors | 1.38 | 1.38 |

Table 8 indicates the effect of the incubation with SCM-factor-containing fractions on the response of the lymphocytes to either SCM factor or phytohaemagglutinin, as reflected in the $RR_{SCM}$. Lymphocytes which were either not preincubated, or which were preincubated with ultrafiltrate from healthy donors filtered through a filter with a nominal 1000-dalton molecular weight cutoff, or which were preincubated with ultrafiltrate from donors with cancer filtered through a filter with a nominal 500-dalton molecular weight cutoff, showed an $RR_{SCM}$ of 1.35 or higher, as expected. By contrast, lymphocytes which were preincubated With fractions containing SCM factor all showed decreases in the $RR_{SCM}$ to a value of 0.65–0.80 characteristic of lymphocytes originally isolated from patients with malignant disease.

Example 13

Effect of the Isolated SCM Factor on Lymphocyte Cytotoxicity

To demonstrate the effect of the isolated SCM factor on the natural cytotoxicity of potentially SCM-responding lymphocytes toward malignant cells, such lymphocytes obtained from healthy donors were incubated for 2½ hr at 37° C. with plasma containing SCM factor isolated as previously described from blood samples of donors afflicted with cancer. Aliquots of these lymphocytes were also retained as controls and not incubated. In addition, potentially SCM-responding lymphocytes were obtained from donors having cancer, and treated in the same manner—some aliquots incubated with plasma containing SCM factor and others retained as controls and not incubated.

After incubation the cytotoxicity of the lymphocytes was tested in accordance with the method described in M. R. Potter and M. Moore, "Natural Cytotoxic Reactivity of Human Lymphocyte Subpopulations," *Immunology* 37, 187–194 (1979). In accordance with this published method cells of the K 562 human myeloid cell line labeled with $^{51}$Cr were used as target cells for the assay. The potentially SCM-responding lymphocytes were used as the effector cells. The ratio of target cells to effector cells was 1 to 20. Release of the $^{51}$Cr indicates that the effector cells are toxic to the target cell. The percent of cytotoxicity is determined as follows:

$$\text{Percent cytotoxicity} = \frac{R_S - R_C}{R_T - R_C} \times 100$$

where $R_S$ is the percent of $^{51}$Cr release in the sample, $R_C$ the percent of $^{51}$Cr release in the control and $R_T$ is the percent of $^{51}$Cr release in the presence of a detergent, Triton X-100. The results are shown in Table 9. These results show that incubation of potentially SCM-responding lymphocytes from healthy donors for 2.5 hr with ultrafiltrates filtered through filter with a nominal 1000-dalton molecular weight cutoff decreased their cytotoxicity by over 90%. When the incubation was performed with potentially SCM-responding lymphocytes from cancer patients, the decrease in cytotoxicity was smaller, between 40 and 90%. However, such lymphocytes from cancer patients had lower levels of cytotoxicity before incubation, and the residual level of cytotoxicity remaining after incubation with ultrafiltrate was comparable to that remaining after incubation of lymphocytes from healthy donors. The lower level of cytotoxicity present in cells from cancer patients was consistent with a decrease of such cytotoxicity caused by in vivo exposure to factors such as the cancer-associated SCM recognition factor.

mas of 12 different cancers, are presented in Table 10. The sequences were determined by an automated Edman degradation procedure, using the Applied Biosystems 477A protein sequencer coupled with an on-line 120A PTH-amino acid analyzer. Sequence-calling software was used to establish the amino acid residue at each cycle. The sequences of the SCM-factor peptides were obtained in repetitive analyses of two to three different preparations, isolated and purified to homogeneity, from pooled blood plasmas of about 5 to 50 different patients with a diagnosis of the same type of cancer. Amino acid residues designated in parentheses below the primary, most significant residue detected at the particular degradation cycle represent secondary amino acid residues present in some of the degradation cycles in significant amounts. These secondary residues may indicate the presence of genetic polymorphisms of the SCM factors from individual blood donors contained in the sample pool that was used for sequencing; many, but not all, of the substitutions in these polymorphisms are conservative substitutions. In two cases, where a total of 35 amino acids were seen, the last six were weak. This indicates that two separate factors were present in the preparations, one of 29 amino acids, and a second of up to 35 amino acids. These two preparations were from donors with cancer of the prostate and seminoma of the testes. In some cases, no amino acid was seen in a particular cycle, designated by "X." These amino acids are most likely cysteine, and are otherwise referred to as cysteine (C). This is because of the 20 common amino acids, cysteine is the only one not detectable by the Edman degradation procedure.

TABLE 9

EFFECT OF SCM FACTOR ON NATURAL LYMPHOCYTE TOXICITY AGAINST K 562 HUMAN MYELOID CELL LINE (EXAMPLE 13)

| Diagnosis of Donor of Potentially SCM-Responding Lymphocytes | Diagnosis of Donor of SCM Factor as Ultrafiltrate | % Cytotoxicity of Lymphocytes: | | % Decrease in Cytotoxicity |
|---|---|---|---|---|
| | | Before Incubation | After Incubation | |
| Healthy Donor #1 | Ca-Cervix | 40.0 | 2.2 | 94.5 |
| Healthy Donor #2 | Ca-Brochus | 30.0 | 1.7 | 94.3 |
| Healthy Donor #3 | Ca-Larynx | 11.0 | 0.76 | 93.1 |
| Healthy Donor #4 | Ca-Layrnx | 22.0 | 2.2 | 90.0 |
| Healthy Donor #5 | Ca-Pharynx | 41.0 | 0.33 | 99.2 |
| Ca-Tongue | Ca-Larynx | 23.0 | 2.1 | 90.9 |
| Ca-Lip | Ca-Bronchus | 7.4 | 2.7 | 63.5 |
| Ca-Ovary | Ca-Bronchus | 10.0 | 6.1 | 39.0 |
| Ca-Cervix | Ca-Cervix | 25.2 | 1.5 | 94.0 |
| Ca-Bronchus | Ca-Cervix | 29.6 | 3.1 | 89.5 |
| Ca-Bronchus | Ca-Cervix | 29.6 | 3.1 | 89.5 |

Example 14

Amino Acid Sequences of Isolated SCM Factors

The amino acid sequences of isolated SCM factors, determined from purified preparations from blood plas-

TABLE 10

AMINO ACID SEQUENCES OF PURIFIED ISOLATED SCM FACTORS

```
                         10                    20                    30
Ca-BREAST:    V I P P E V K F N K P F V F L M I D Q N T K T P L F M G K
              (M)                                      (V)
Ca-LUNG:      M I P P E V K F N K P F V F L M I D Q N T K V P L F M G K
                                                       (T)
Ca-COLON:     M I P P E V K F N K P F V F L M I D Q N T K V P L F M G K
                  (D)
MELANOMA:     M I P P E V K F N K P F V F L M I D Q N T K X P X F M G X

SCC-CERVIX:   M I P P E V K F N K P F V F L M I D Q N T K V P L F M G K
                (S)
```

TABLE 10-continued
AMINO ACID SEQUENCES OF PURIFIED ISOLATED SCM FACTORS

| | |
|---|---|
| Ca-OVARY: | M I P P E V K F N K P F V F L M I D Q N T K X X L F M G K |
| | (V) |
| Ca-UTERUS: | R I P P E V K F N K P F V F L M I D Q N T K R P L F M G K |
| | (S) |
| Ca-PANCREAS: | V I P P E V K F N K P F V F L M I D Q N T K X P L F M G K |
| Ca-RENAL: | V I P P E V K F N X P F V F L M I D Q N T K V P L F M G K |
| Ca-GASTRIC: | R I P P E V K F N K P F V F L M I D Q N T K X P X F M G X (V V N X T E) |
| (SARCOMA) | (S)   W |
| Ca-PROSTATE: | V I P P E V K F N K P F V F L M I E Q N T K S P L F M G K (V V N P T Q) |
| | (S)   W |
| Ca-TESTIS: | S I P P E V K F N K P F V F L M I E Q N T K S P L F M G K  V V N P T Q |
| (SEMINOMA) | (V) |

Example 15
SCM Activity of Synthetic SCM Factor

A synthetic SCM factor, representing the "consensus sequence" of M-I-P-P-E-V-K-F-N-K-P-F-V-F-L-L-I-D-Q-N-T-K-V-P-L-F-M-G-K, was synthesized using conventional solid-phase peptide synthesis techniques. Such techniques are described, for example, in M. Bodanszky, "Peptide Chemistry" (Springer-Verlag, Berlin, 1988), Ch. 10, "Solid Phase Peptide Synthesis."

The SCM activity of this synthetic SCM factor was tested by the standard SCM test. The fraction of SCM-responding lymphocytes from patients with a number of types of cancer and from normal healthy donors was challenged with the synthetic SCM factor. The factor was dissolved in sterile water for injections and was administered to the SCM-responding lymphocytes at 190 picomoles per $3 \times 10^6$ lymphocytes. As can be seen in Table 11, lymphocytes from patients with several types of cancer responded with significant decreases in intracellular fluorescein fluorescence polarization to the synthetic SCM factor. Most of these decreases in fluorescence polarization exceeded 40% and were comparable to the decreases seen with the most highly purified preparations of SCM factor isolated from blood plasma. This response was also specific for lymphocytes from patients with cancer. When lymphocytes from healthy donors were challenged with synthetic SCM factor, no decrease in fluorescence polarization was seen, even when the cells were challenged with increased quantities of SCM factor as high as 960 picomoles per $3 \times 10^6$ lymphocytes.

Example 16
Fragments of Synthetic SCM Factor

Peptides representing distinct fragments of the synthetic SCM factor of Example 15 were synthesized by conventional solid-phase peptide synthesis techniques. These peptides were designated F1–F5 and have the following sequences:

F1:  M-I-P-P-E-V-K-F-N-K-P-F-V-F-L-M-D-Q-N-T-K;

F2:  F-N-K-P-F-V-F-L-M-I-D-Q-N-T-K-V-P-L-F-M-G-K;

F3: F-N-K-P-F-V-F-L-M-I-D-Q-N-T-K;

F4: F-L-M-I-D-Q-N-T-K; and

F5: M-I-P-P-E-V-K-F-N-K-P-F-V-F.

These fragments represented the following portions of the complete synthetic SCM molecule: F1, amino acids 1–22; F2, amino acids 8–29; F3, amino acids 8–22; F4, amino acids 14–22; and F5, amino acids 1–13.

Example 17
Activity of Fragments of Synthetic SCM Factor of Example 16 in the SCM Test Fragments F1 through F5, representing different portions of the synthetic SCM molecule, were used as the challenging agents for both lymphocytes from patients with cancer and lymphocytes from normal donors in SCM tests. The SCM tests were performed as described in Example 15. The results are shown in Table 11. Fragments F1, F2, F3, and F4 were all fully active in the SCM test, while fragment F5 was inactive. For fragments F1 through F4, the expected specificity of the SCM response was maintained, as these fragments gave no decrease in fluorescence polarization when used to challenge lymphocytes isolated from donors free of malignancy.

Of these peptides representing active fragments of the synthetic SCM molecule, the smallest is F4, residues 14–22. All of the other active peptides include this segment, while F5, which does, not have this segment, is inactive. Accordingly, and based upon these results, residues 14–22 can be considered to be the active site of the synthetic SCM-factor molecule. Significantly, this region of the peptide is virtually invariant in the isolated SCM factors, except for the extremely conservative substitution of glutamic acid (E) for aspartic acid (D) at position 8 in two of the factors.

TABLE 11
SCM ACTIVITY OF SYNTHETIC SCM FACTOR AND FRAGMENTS F1 TO F5

| | SCM Response as % of Control P Value to: | | | | | |
|---|---|---|---|---|---|---|
| Diagnosis of Lymphocyte Donor | Synthetic SCM Factor | F1 | F2 | F3 | F4 | F5 |
| Melanoma | 58.0 | 62.8 | 63.6 | 61.5 | — | — |
| Ca-Ovary | 58.4 | — | 65.0 | — | 60.2 | — |
| Ca-Breast | — | 59.0 | — | 61.2 | — | — |
| Melanoma | — | 66.4 | 65.0 | 59.4 | — | — |
| Ca-Breast | 56.7 | 65.7 | — | 63.2 | — | — |
| Ca-Breast | — | 68.4 | 61.5 | 56.7 | — | — |
| Ca-Liver | — | 58.0 | 58.8 | 55.0 | — | — |
| Ca-Stomach | 60.0 | 66.7 | 67.0 | — | — | — |
| Ca-Testis | 57.3 | — | — | 67.0 | 56.2 | — |
| Ca-Lung | 59.7 | — | — | — | 57.0 | 99.5 |
| Ca-Lung | 69.0 | 73.0 | — | 68.5 | — | — |
| Ca-Breast | 57.0 | — | — | — | 58.0 | 99.0 |
| Healthy (M,30) | 102.0 | 104.0 | — | — | 100.0 | — |
| Healthy (F,29) | 100.0 | 101.0 | — | 104.0 | 103.0 | — |
| Healthy (M,36) | 100.5 | — | — | 100.0 | 102.0 | — |
| Healthy (F,59) | 99.1 | 100.0 | — | — | 99.2 | — |

TABLE 11-continued

SCM ACTIVITY OF SYNTHETIC SCM FACTOR AND FRAGMENTS F1 TO F5

| Diagnosis of Lymphocyte Donor | SCM Response as % of Control P Value to: | | | | | |
|---|---|---|---|---|---|---|
| | Synthetic SCM Factor | F1 | F2 | F3 | F4 | F5 |
| Healthy (M,28) | 98.8 | 100.3 | 100.5 | — | 99.3 | — |

Concentrations of synthetic SCM factor and fragments F1 to F5 used in these examples were 190 picomoles per $2 \times 10^6$ lymphocytes.
Fragments represent the following amino acid residues of synthtic SCM factor: F1 (1-22); F2 (8-29); F3 (8-22); F4 (14-22); and F5 (1-13).
P value denotes intracellular fluorescein fluorescence polarization value as measured with the SCH test.

Example 18

Amphipathicity Profiles of SCM-active Peptides and Peptide Fragments

FIG. 1 shows the amphipathicity profile of the F4 peptide fragment. For comparison, FIG. 2 also shows the amphipathicity profile of the synthetic SCM-active octapeptide whose sequence and SCM activity are disclosed in our co-pending patent application Ser. No. 07/163,250, filed Mar. 2, 1988, entitled "Synthetic SCM-Active Cancer Recognition Peptides," and incorporated herein by this reference. The amphipathicity profiles of the SCM-active octapeptide and of F4 were nearly identical, even though only 4 of 8 of the amino acids of the octapeptide are homologous with those of F4.

Table 12 shows hydrophilicity values of the individual amino acids in the sequence of F4, the synthetic SCM-active octapeptide of our co-pending patent application Ser. No. 07/163,250, and of the purified experimental allergic encephalitogenic (EAE) nanopeptide, which is inactive in the SCM test. The only difference between the synthetic SCM-active octapeptide and the inactive EAE nanopeptide is an additional serine residue in position 2. Serine has a positive hydrophilicity value (+0.3), while in the active F4 fragment the first four residues all have negative hydrophilicity values and in the synthetic SCM-active octapeptide, residues 1, 2, and 4 have negative hydrophilicity values and residue 3, glycine, has a hydrophilicity value of 0.0. The hydrophilic serine in position 3 of EAE disrupts the sequence of negative hydrophilicities. This disruption appears sufficient to prevent the recognition of EAE peptide by the receptors in the lymphocytes of cancer patients that recognize the SCM-active peptide. Accordingly, pure EAE peptide purified away from the SCM-active octapeptide is completely devoid of SCM activity. This example suggests the importance of amphipathicity profiles in controlling the recognition of the SCM factor by its corresponding receptor.

TABLE 12

HYDROPHILICITY VALUES (HV) OF AMINO ACID (AA) SEQUENCES OF SCM-ACTIVE AND SCM-INACTIVE PEPTIDES

| SCM-Active Peptides: | | | | SCM-Inactive EAE-Nano-peptide | |
|---|---|---|---|---|---|
| F4 Nanopeptide | | Octapeptide | | | |
| AA | HV | AA | HV | AA | HV |
| F | −2.5 | F | −2.5 | F | −2.5 |
| L | −1.8 | W | −3.4 | S | +0.3 |
| M | −1.3 | G | 0.0 | W | −3.4 |
| I | −1.8 | A | −0.5 | G | 0.0 |
| D | +3.0 | E | +3.0 | A | +3.0 |
| Q | +0.2 | G | 0.0 | E | +3.3 |
| N | +0.2 | Q | +0.2 | G | 0.0 |
| T | −0.4 | R | +3.0 | Q | +0.2 |
| K | +3.0 | | | R | +3.0 |

Example 19

Induction of SCM Response Characteristic of Malignancy in Lymphocytes from Healthy Donors by Synthetic SCM Factor The synthetic SCM factor can induce an SCM response characteristic of malignancy in lymphocytes from healthy donors. The induction of this response requires active protein synthesis.

To demonstrate this induction, SCM-responding lymphocytes from normal, healthy donors were isolated and divided into four aliquots containing $5 \times 10^6$ cells/ml. Lymphocytes in the first aliquot were suspended in PBS and were used as untreated controls. Lymphocytes in the second aliquot were incubated with 400 picomoles of synthetic SCM factor, or, alternatively, with purified SCM factor from plasma from patients with cancer. Lymphocytes in the third aliquot were incubated with 400 picomoles of synthetic SCM factor plus 10 μg/ml of cycloheximide. Lymphocytes in the fourth aliquot were incubated with 400 picomoles of synthetic SCM factor plus 10 μg/ml of actinomycin D. All four aliquots were incubated at 37° C. for 2.5 hours. The aliquots were then washed three times with PBS, collected by centrifugation, and resuspended in PBS. The aliquots were then challenged with 190 picomoles of synthetic SCM factor per $2 \times 10^6$ cells for 40 min at 37° C. and the intracellular fluorescein fluorescence polarization was determined for each sample as previously described. As can be seen in Table 13, untreated control lymphocytes from a healthy donor did not respond to synthetic SCM factor in the SCM test; i.e., there was no decrease in fluorescence polarization in comparison to unchallenged control lymphocytes. In contrast, lymphocytes primed or induced by pretreatment with synthetic SCM factor responded with a significant decrease in fluorescence polarization when challenged either with synthetic SCM factor or with purified SCM factor isolated from blood plasma of patients with colon cancer. This response was prevented when the pre-incubation occurred in the presence of the protein synthesis inhibitors cycloheximide or actinomycin D, thus indicating that active protein synthesis was need to induce the response to SCM-active peptides.

TABLE 13

IN VITRO INDUCTION OF SCM RESPONSES IN NORMAL, HEALTHY LYMPHOCYTES (NHL) BY PRETREATMENT WITH SYNTHETIC SCM FACTOR

| Treatment of NHL Before Challenge with SCM Factor | Source of Challenging SCM Factor | SCM Response: P Value as % of Control |
|---|---|---|
| Untreated NHL Control | — | 100.0 |
| NHL + Synthetic SCM Factor (2.5 hr incubation); Washed | Synthetic | 63.5 |
| NHL + Synthetic SCM Factor | Plasma | 62.2 |

TABLE 13-continued
IN VITRO INDUCTION OF SCM RESPONSES IN
NORMAL, HEALTHY LYMPHOCYTES (NHL) BY
PRETREATMENT WITH SYNTHETIC SCM FACTOR

| Treatment of NHL Before Challenge with SCM Factor | Source of Challenging SCM Factor | SCM Response: P Value as % of Control |
|---|---|---|
| (2.5 hr incubation); Washed NHL + Synthetic SCM Factor + 10 g/ml Cycloheximide (2.5 hr incubation); Washed | (Ca-Colon) Synthetic | 104.0 |
| NHL + Synthetic SCM Factor + 10 g/ml Actinomycin D (2.5 hr incubation); Washed | Synthetic | 99.7 |

Example 20

Preparation of Antibodies to Synthetic SCM Factor

The synthetic SCM factor molecule was used to immunize experimental animals. Both pure synthetic SCM-factor molecules and SCM conjugated to the carrier keyhole limpet hemocyanin (KLH) via an added carboxy-terminal cysteine using N-succinyl bromoacetate as the cross-linking agent. These immunogens were used to immunize female New Zealand rabbits. Both immunogens were diluted for primary immunization to 1.0 mg/ml with sterile PBS, combined with an equal volume of Freund's complete adjuvant, and emulsified. For primary immunization, a total of 25 µg or 50 µg of either synthetic SCM factor or synthetic SCM factor conjugated with KLH (SCM-KLH) was injected into each rabbit; two rabbits were used for each dose range. The inoculate was administered at 0.2 ml into two legs intramuscularly and over a minimum of 12 dorsal sites subcutaneously at 0.2 ml per site. One month later, the first booster injection was administered. Synthetic SCM factor and SCM-KLH were each administered with an equal-volume mixture of Freund's complete and incomplete adjuvants and emulsified. The booster inoculates were injected via intramuscular and subcutaneous sites similar to those used for primary inoculations. Total doses of 25 µg or 50 µg of immunogen per rabbit were administered in the booster injections.

Blood samples taken 10 weeks after primary immunization yielded antisera containing higher amounts of immunoglobulins (IgG) from those animals injected with 50 µg of immunogen than from those animals injected with 25 µg of immunogen. Radial immunodiffusion tests, conducted as described in W. Becker, "Determination of Antisera Titres Using the Single Radial Immunodiffusion Method," *Immunochemistry* 6, 539 (1969), gave precipitation reactions against the unconjugated SCM factor and SCM factor conjugated to bovine serum albumin (BSA).

To separate the immunoglobulins containing the desired antibodies from the antisera, the immunoglobulins were first precipitated with an equal volume of saturated ammonium sulphate. The precipitates were then dissolved in 0.9% NaCl. To remove ammonium sulphate, the antibody-containing solutions were either dialyzed or ultrafiltered 10 times through an Amicon TM membrane filter with a 5000-dalton molecular weight cutoff. Antibodies were kept frozen at −40° C. until use.

Example 21

ELISA Assay for SCM Factor

A double-antibody enzyme-linked competitive immunosorbent assay (ELISA) was developed for detection of SCM factor by the use of antibodies raised against SCM factor (Example 20). The ELISA assay is depicted schematically in FIG. 3. In the first step, SCM factor is attached to a solid phase such as plastic, typically by passive adsorption. In the second step, the sample to be assayed, along with a limited quantity of the anti-SCM antibody, is added. After a thorough washing, an excess of the labeled second antibody, goat anti-rabbit IgG labeled with the enzyme alkaline phosphatase, is then added in the third step. The substrate for alkaline phosphatase, p-nitrophenylphosphate, is then added, and the absorbance at 405 nm ($A_{405}$) is measured. In this assay, any free SCM factor added at the second step competes with the SCM factor adsorbed to the solid phase. Only the solid-phase SCM to which the first and second antibodies are bound yields color. Therefore, the higher is the concentration of SCM factor in the test sample, the lower is the measured $A_{405}$. This is typical of a competitive assay.

Variations on this procedure have been employed to detect SCM molecules in cancer cells, supernatants of growth culture media, blood plasma preparations from cancer patients, and purified extracts of SCM from various sources.

Example 22

Activity of Anti-SCM Antibodies

The activity of the antibodies of Example 20 raised against both unconjugated SCM factor and the KLH-SCM factor conjugate was determined by a variation of the ELISA assay of Example 21. Different dilutions of the antibodies were used, and no sample representing free SCM was added to the assay. The results are shown in FIG. 4 for the antiserum raised against unconjugated SCM factor, and in FIG. 5 for the KLH-SCM factor conjugate. As can be seen, both antibody preparations were active against purified SCM factor.

Example 23

Determination of SCM-Factor Levels in Ultrafiltrates of Blood Plasmas by ELISA Assay The level of SCM factor was determined in a number of ultrafiltrates of blood plasmas from both healthy donors and cancer patients. Ultrafiltrates of blood plasmas from 12 cancer patients and 12 normal, healthy donors were prepared by filtration through an Amicon TM YM2 membrane filter with a 1000-dalton molecular weight cutoff. The level of SCM factor was assayed immunochemically by the ELISA assay of Example 21. The results are shown in Table 14. The levels of SCM factor detected by the ELISA assay were in the nanogram range per milliliter of ultrafiltrate. In the ultrafiltrates from donors with cancer, they were from 4.8 to 25.5 ng/ml. In normal, healthy donors, the levels of SCM factor were either below the minimum detectable level or up to a maximum of 1.85 ng/ml.

TABLE 14
LEVELS OF SCM FACTOR IN AMICON ™ YM2 ULTRA-FILTRATES OF BLOOD PLASMAS FROM CANCER PATIENTS AND NORMAL, HEALTHY DONORS AS DETECTED BY ANTI-SCM FACTOR ANTIBODIES IN COMPETITIVE ELISA ASSAYS

| Diagnosis of Blood Donor | Donor's Sex and Age | | SCM Factor ng/ml |
|---|---|---|---|
| Ca-Breast | F | 39 | 12.0 |
| Ca-Breast | F | 50 | 10.1 |
| Ca-Breast | F | 49 | 7.0 |
| Ca-Lung | F | 76 | 13.4 |
| Ca-Lung | F | 67 | 8.7 |
| Ca-Lung | M | 47 | 5.5 |
| Ca-Pancreas | F | 50 | 8.5 |
| Ca-Colon | M | 42 | 4.8 |
| Ca-Colon | M | 44 | 14.0 |
| Ca-Colon | F | 60 | 10.5 |
| Malignant Melanoma | F | 38 | 15.7 |
| Malignant Melanoma | F | 50 | 25.5 |
| Normal Healthy | M | 31 | ND[a] |
| Normal Healthy | M | 49 | ND |
| Normal Healthy | M | 26 | 0.60 |
| Normal Healthy | M | 38 | 1.85 |
| Normal Healthy | M | 29 | 1.03 |
| Normal Healthy | M | 36 | 1.65 |
| Normal Healthy | F | 27 | 0.22 |
| Normal Healthy | F | 32 | 0.82 |
| Normal Healthy | M | 34 | ND |
| Normal Healthy | M | 46 | 0.22 |

[a]ND = none detected

Example 24

NH$_2$-terminal Amino Acid Sequences of SCM Factor Secreted from Human Cancer Cells in Culture The partial NH$_2$-terminal amino acid sequences of SCM-factor molecules present in the supernatant of serum-free culture media in which human cancer cells were grown were determined. The cells used were MCF7 breast cancer cells and HCT80 colon cancer cells. The presumed SCM-factor molecules from the supernatants were isolated and purified to homogeneity using the combined procedures of Examples 1, 3, and 5 as described above for the purification of SCM factor from blood plasma of cancer patients.

The sequence analyses on 8-picomolar amounts of the factor isolated from the supernatant culture medium from human MCF7 breast cancer cells identified the first 16 NH$_2$-terminal residues as: M-I-P-P-E-V-X-F-N-K-P-F-(V-I-F-M). The last four residues gave a weak signal. With two relatively conservative substitutions, methionine for valine in position 1 and isoleucine for leucine in position 15, 15 out of 16 of the amino acids of this segment are identical with the majority sequence of the SCM factor isolated from plasma of patients with breast cancer in Example 14. At position 1, methionine was also found in the purified preparation from blood plasma as a less-frequent alternative to valine.

Similarly, 5-picomole amounts of purified SCM factor from the supernatant culture medium of the culture of HCT-80 colon cancer cells were sequenced. Six amino-terminal amino acids were determined: M-I-P-P-X-V. Five out of six of these amino acids are identical to those determined on the SCM preparation purified from blood plasma of patients with colon cancer. The amino acid in position 4, denoted as X, could not be determined due to the weak signal.

Example 25

Reactivity of SCM Factor Secreted from Human Cancer Cells In Culture with Anti-SCM-factor Antibodies The SCM factors secreted from human cancer cells in culture whose amino acid sequences were presented in Example 24 also reacted with the anti-SCM antibody of Example 20. A variation on the ELISA assay of Example 21 was used. In this version of the ELISA assay, the assay was performed directly on the eluate from the RP-HPLC purification step that remained adsorbed to the Eppendorf ™ collection tubes after loading of the bulk of the eluates onto the sequenator disk. No other SCM factor was added, and there was no additional sample added to the assay. This version of the SCM ELISA assay is noncompetitive; the larger is the quantity of SCM factor adsorbed to the Eppendorf ™ tubes, the higher is the measured A$_{405}$. The results, shown in Table 15, clearly indicate the presence of material able to react with anti-SCM antibody in these fractions.

TABLE 15
ELISA ASSAYS ON SCM FACTOR IN RP-HPLC ELUATES PURIFIED FROM CULTURE MEDIA OF CANCER CELLS

| Origin of Eluate | Sample Number | ELISA A$_{405}$ Signal/Background Ratio[a] |
|---|---|---|
| MCF7 Breast Cancer Cells | 1 | 43 |
| MCF7 Breast Cancer Cells | 2 | 17 |
| MCF7 Breast Cancer Cells | 3 | 71 |
| HCT80 Colon Cancer Cells | 1 | 34 |
| HCT80 Colon Cancer Cells | 2 | 12 |

[a]Background is ELISA A$_{405}$ in tubes without adsorbed SCM factor.

Example 26

Detection of SCM Factor in Human Cancer Cells In Culture by ELISA Assay

Human cancer cells in culture were directly shown to contain SCM-factor molecules by antibody reactivity. Washed cells from monolayered cultures of several human cancer cells: MCF7 breast cancer cells; T1080 fibrosarcoma cells; A2780 ovarian cancer cells; and HCT80 colon cancer cells, were assayed directly by the noncompetitive ELISA assay procedure of Example 25. The data is presented in Table 16. The calculated ELISA absorbance ratios (i.e., the absorbance in the presence of anti-SCM antibody divided by the absorbance in the absence of anti-SCM antibody, which are a relative measure of the amounts of SCM factor per 4×10$^6$ cells) showed that different cancer cell lines produced, under identical conditions, different amounts of SCM factor.

Treatment of cultured cancer cells with the protein synthesis inhibitor cycloheximide indicated that inhibition of protein synthesis decreased the concentration of SCM factor associated with the cultured cancer cells. The decrease was 25.3% for MCF7 breast cancer cells and 34% for T1080 fibrosarcoma cells. This data is presented in Table 17.

TABLE 16

SCM FACTOR IN HUMAN CANCER CELLS IN CULTURE AS DETECTED BY ELISA ASSAYS USING ANTI-SCM FACTOR ANTIBODY

| Human Cancer Cell Line (4 × 10⁶ cells) | ELISA $A_{405}$ Ratio[a] |
|---|---|
| MCF7 Breast Cancer Cells | 6.0 |
| MCF7 Breast Cancer Cells | 10.0 |
| MCF7 Breast Cancer Cells | 7.0 |
| T1080 Fibrosarcoma Cells | 6.5 |
| A2780 Ovary Cancer Cells | 4.6 |
| HCT80 Colon Cancer Cells | 3.0 |

[a]ELISA $A_{405}$ Ratio = $\frac{\text{ELISA } A_{405} \text{ (cells + antibody)}}{\text{ELISA } A_{405} \text{ (cells - antibody)}}$

TABLE 17

EFFECT OF CYCLOHEXIMIDE ON SCM FACTOR SYNTHESIS IN HUMAN CANCER CELLS IN CULTURE AS DETECTED BY ELISA ASSAYS USING ANTI-SCM FACTOR ANTIBODY

| Cancer Cell Line (4 × 10⁶ cells) | Cycloheximide (μg/10⁶ cells) | Incubation (hrs) | Corrected $A_{405}$[a] | Corrected $A_{405}$ As % of Control |
|---|---|---|---|---|
| MCF7 Breast Cancer | 0 | 0 | 2.0716 | 100.0 |
| MCF7 Breast Cancer | 20 | 3 | 1.8893 | 91.2 |
| MCF7 Breast Cancer | 0 | 0 | 0.9654 | 100.0 |
| MCF7 Breast Cancer | 50 | 16 | 0.7217 | 74.7 |
| T1080 Fibrosarcoma | 0 | 0 | 1.5060 | 100.0 |
| T1080 Fibrosarcoma | 50 | 16 | 0.9940 | 66.0 |

[a]Corrected $A_{405}$ = (ELISA $A_{405}$ in presence of cells) - (ELISA $A_{405}$ in absence of cells)

Example 27

Effect of SCM Factor on DNA Synthesis

The effect of SCM factor on DNA synthesis was studied on normal rat hepatocytes grown in culture. Details of the procedure were as described in I. Hayashi & B. I. Carr, "DNA Synthesis in Rat Hepatocytes: Inhibition by a Platelet Factor and Stimulation by an Endogenous Factor," *J. Cell. Physiol.* 125, 82 (1985). Briefly, hepatocytes were obtained by the high-pressure collagenase perfusion technique from male rat livers. The cells were plated at $3 \times 10^5$ cells per 35-mm tissue cultured dish in Dulbecco's modified Eagle's growth medium (DME) supplemented with 10% calf serum. Three hours after plating the cells, the medium was changed to serum-free DME to which 10 ng/ml of epidermal growth factor (EGF) was added to trigger DNA synthesis. To aliquots of the cell suspension, SCM factor was added in concentrations of 1000 ng/ml, 100 ng/ml, 10 ng/ml, 1.0 ng/ml, and 0.1 ng/ml. The culture medium was changed daily and the culture plates were kept at 37° C. in 5% $CO_2$-air atmosphere.

About 72 hours after plating, 5 μCi/ml of tritiated thymidine was added to each dish for about 6 to 8 hours. DNA synthesis was measured on cells scraped off the tissue plates with rubber policemen into glass tubes and collected by centrifugation. After washing once with PBS, 2 ml of cold 10% trichloroacetic acid (TCA) was added to each tube and the cells were kept at 4° C. for one hour. After an additional wash with 10% TCA, the cells were collected by centrifugation and hydrolyzed in 1 ml of 0.5 N NaOH at 37° C. overnight. Aliquots of these samples were used for protein assay using colorimetric measurement at 595 nm after staining with the protein-specific dye Coomassie brilliant blue. The remainder of the samples were used for measurement of tritiated thymidine incorporation. For this, samples were precipitated by addition of 0.25 ml of 50% TCA; after 10 minutes on ice, they were passed through Whatman GF/C filters and dried. The uptake of tritiated thymidine into acid-precipitable material was counted in a Beckman scintillation counter. The results are presented as counts per minute incorporated per milligram of cellular protein in Table 18. The dose effect was highest at the lowest dose of the SCM factor, i.e., at 0.1 ng/ml, and decreased at higher doses to a slight inhibition of DNA synthesis (13 percent) at 1000 ng/ml. Since the enhancement effect of SCM factor on DNA synthesis was assayed in this system in addition to the effect of EGF as a promoter of cell growth and DNA synthesis, the inhibitory effect at the highest dose of the SCM factor could be the reaction to excessive stimulation in the presence of both the SCM factor and EGF.

TABLE 18

EFFECT OF SCM FACTOR ON DNA SYNTHESIS OF RAT HEPATOCYTES

| SCM Factor Dose (ng/ml) | Relative DNA Synthesis Per μg DNA (%)[a] |
|---|---|
| 1000 | 86.5 |
| 100 | 134.5 |
| 10 | 171.5 |
| 1 | 184.0 |
| 0.1 | 192.4 |

[a]Relative DNA synthesis per μg DNA = $\frac{\frac{\text{cpm/μg DNA}}{\text{(EGF + SCM Factor)}} - \frac{\text{cpm/μg DNA}}{\text{(EGF only)}}}{\text{cpm/μg DNA (EGF)} - \text{cpm (Background)}}$ Data was corrected for quenching caused by varying protein content.

Example 28

Effect of SCM Factor on Inhibition of Serine Proteases by α-1-PI Protease Inhibitor A protease activity using casein-resorufin as a protease substrate was performed to determine the effect of SCM factor on inhibition of the serine proteases trypsin, elastase, and cathepsin G by the serine protease inhibitor α-1-PI. The protocol provided by the manufacturer, Boehringer-Mannheim Biochemica, was followed to assay protease activity. Table 19 shows the results when trypsin was used, Table 20 shows the results when elastase was used, and Table 21 shows the results when cathepsin G was used. In each case, SCM factor by itself did not affect the proteolytic activity. However, when SCM factor was added before α-1-PI or simultaneously in a mixture with α-1-PI, it prevented the inhibition of trypsin by α-1-PI. The degree of this effect depended on the quantity of SCM factor added. In contrast, as can be seen in Table 19, when α-1-PI was allowed to react first with trypsin, subsequent addition of SCM factor did not reverse the inhibition of trypsin by α-1-PI. The active portion of the molecule that prevents inhibition of the proteolytic enzymes by α-1-PI resides within the first seven amino-terminal amino acid residues of the SCM factor. This portion of the molecule is designated "fraction 6" or F6. The effectiveness of equimolar amounts of the peptide F6, as compared to the entire SCM factor molecule (Table 20) in preventing the inhibition of elastase by α-1-PI is shown in Table 22.

TABLE 19
EFFECT OF SCM FACTOR ON INHIBITION OF TRYPSIN ACTIVITY BY α-1-PI PROTEASE INHIBITOR

| Sequence of Addition of Reaction Components[a] | Trypsin Activity in Casein-Resorufin Assay as % of Untreated Control Enzyme |
|---|---|
| 3 μg Trypsin (control) | 100.0 |
| 3 μg Trypsin + 230 μg SCM Factor | 99.9 |
| 3 μg Trypsin + 6.6 μg α-1-PI | 13.6 |
| 3 μg Trypsin + 6.6 μg -1-PI (60 min inc.) + 230 μg SCM Factor | 14.0 |
| 3 μg Trypsin + 21 μg SCM Factor (10 min inc.) + 6.6 μg α-1-PI | 15.6 |
| 3 μg Trypsin + 60 μg SCM Factor (10 min inc.) + 6.6 μg α-1-PI | 40.0 |
| 3 μg Trypsin + 100 μg SCM Factor (10 min inc.) + 6.6 μg α-1-PI | 62.5 |
| 3 μg Trypsin + 150 μg SCM Factor (10 min inc.) + 6.6 μg α-1-PI | 97.7 |
| 3 μg Trypsin + 230 μg SCM Factor (10 min inc.) + 6.6 μg α-1-PI | 101.7 |
| 6.6 μg α-1-PI + 230 μg SCM Factor (10 min inc.) + 3 μg Trypsin | 100.6 |

[a]Total reaction volume is 300 μL.

TABLE 20
EFFECT OF SCM FACTOR ON INHIBITION OF ELASTASE ACTIVITY BY α-1-PI PROTEASE INHIBITOR

| Sequence of Addition of Reaction Components[a] | Trypsin Activity in Casein-Resorufin Assay as % of Untreated Control Enzyme |
|---|---|
| 3.2 μg Elastase (control) | 100.0 |
| 3.2 μg Elastase + 230 μg SCM Factor | 100.0 |
| 3.2 μg Elastase + 6.6 μg α-1-PI | 3.5 |
| 3.2 μg Elastase + 10 μg SCM Factor (10 min inc.) + 6.6 μg α-1-PI | 6.4 |
| 3.2 μμg Elastase + 30 g SCM Factor (10 min inc.) + 6.6 μg α-1-PI | 7.0 |
| 3.2 μg Elastase + 60 μg SCM Factor (10 min inc.) + 6.6 μg α-1-PI | 55.8 |
| 3.2 μg Elastase + 100 μg SCM Factor (10 min inc.) + 6.6 μg α-1-PI | 71.1 |
| 3.2 μg Elastase + 150 μg SCM Factor (10 min inc.) + 6.6 μg α-1-PI | 77.5 |
| 3.2 μg Elastase + 230 μg SCM Factor (10 min inc.) + 6.6 μg α-1-PI | 90.1 |

[a]Total reaction volume is 300 μL.

TABLE 21
EFFECT OF SCM FACTOR ON INHIBITION OF CATHEPSIN G ACTIVITY BY α-1-PI PROTEASE INHIBITOR

| Sequence of Addition of Reaction Components[a] | Cathepsin G Activity in Casein-Resorufin Assay as % of Untreated Control Enzyme |
|---|---|
| 1 μg Cathepsin G (control) | 100.0 |
| 1 μg Cathepsin G + 240 μg SCM Factor | 97.0 |
| 1 μg Cathepsin G + 6.6 μg α-1-PI | 20.0 |
| 1 μg Cathepsin G + 240 μg SCM Factor (10 min inc.) + 6.6 μg α-1-PI | 103.0 |

[a]Total reaction volume is 300 μL.

TABLE 22
EFFECT OF AMINO-TERMINAL PEPTIDE FRAGMENT F6 (AMINO ACIDS 1-7) OF SCM FACTOR ON INHIBITION OF ELASTASE ACTIVITY BY α-1-PI PROTEASE INHIBITOR

| Sequence of Addition of Reaction Components[a] | Elastase Activity in Casein-Resorufin Assay as % of Untreated Control Enzyme |
|---|---|
| 3.2 μg Elastase (control) | 100.0 |
| 3.2 μg Elastase + 120 μg F6 | 98.0 |
| 3.2 μg Elastase + 6.6 μg α-1-PI | 3.4 |
| 3.2 μg Elastase + 7.2 μg F6 (10 min inc.) + 6.6 μg α-1-PI | 3.8 |
| 3.2 μg Elastase + 21.6 μg F6 (10 min. inc.) + 6.6 μg α-1-PI | 9.8 |
| 3.2 μg Elastase + 30.0 μg F6 (10 min inc.) + 6.6 μg α-1-PI | 34.2 |
| 3.2 μg Elastase + 60.0 μg F6 (10 min inc.) + 6.6 μg α-1-PI | 38.0 |
| 3.2 μg Elastase + 120.0 μg F6 (10 min inc.) + 6.6 μg α-1-PI | 96.3 |

[a]Total reaction volume is 300 μL.

Example 29

Interaction of Protease Inhibitor α-1-PI With SCM-Factor Receptors

The protease inhibitor α-1-PI was shown to interact strongly with SCM-factor receptors on SCM-responding lymphocytes from cancer patients. This interaction was shown by the removal of the SCM-factor receptors from such lymphocytes by washing after incubation with α-1-PI. This caused reversion of the SCM response to that typical of lymphocytes from donors free of cancer.

SCM-responding lymphocytes were isolated from blood samples of a patient with malignant melanoma and from a normal, healthy donor. Half of the lymphocyte suspension from each sample was incubated with 30 nanomoles of α-1-PI per $6 \times 10^6$ cells for 2.5 hours at 37° C.; the other half was retained as an untreated control. The cells were then washed three times with PBS. Aliquots from both the untreated controls and the α-1-PI-treated samples were challenged for 40 min with phytohemagglutinin (PHA) or SCM factor. The SCM responses were measured by changes in intracellular fluorescein fluorescence polarization as described above under "Performance of the SCM Test." As can be seen in Table 23, the control lymphocytes from the melanoma patients had a $RR_{SCM}$ of 0.63, a typical value for lymphocytes from donors with cancer. The same lymphocytes pre-incubated with α-1-PI had an $RR_{SCM}$ of 1.8, a value typical of lymphocytes from healthy donors. By contrast, incubation of lymphocytes from normal, healthy donors with α-1-PI did not materially effect the responses of these cells in the SCM test to PHA. The $RR_{SCM}$ was 1.74 in the absence of incubation and 1.68 after incubation.

TABLE 23

SCM-RESPONSE MODIFYING EFFECT OF α-1-PI

| Diagnosis of Lymphocyte Donors | in Vitro Treatment of Lymphocytes | SCM Responses: P Value as % of Control to: | | |
|---|---|---|---|---|
| | | PHA | SCM Factor | $RR_{SCM}$ |
| Malignant Melanoma | None | 103.7 | 62.5 | 0.63 |
| | 2.5 hr α-1-PI + 3X Wash | 53.5 | 100.2 | 1.80 |
| Healthy | None | 57.5 | 101.7 | 1.74 |
| | 2.5 hr α-1-PI + 3X Wash | 61.2 | 103.6 | 1.68 |

Example 30

Inhibition of SCM Factor Synthesis

As shown in Table 17 of Example 26, treatment of human cultured cancer cells with cycloheximide, an inhibitor of protein synthesis, decreases the amount of SCM factor produced by these cells. Similarly, ascorbic acid was shown to inhibit the synthesis of SCM factor by MCF7 human breast cancer cells in culture. The amounts of SCM factor per $7 \times 10^6$ cells in the presence or absence of $10^{-3}$ molar ascorbic acid after a 16-hour incubation were measured by the noncompetitive ELISA procedure of Example 25. The results are shown in Table 24. The aliquot of cancer cells incubated in the presence of ascorbate ions produced 43.9% less SCM factor than untreated control cells. The observed inhibition of SCM factor synthesis by ascorbic acid could be the result of decreased metabolic activity of treated cancer cells since ascorbic acid was shown to selectively induce in cancer cells the transition of mitochondria into the idling, orthodox conformation, as described in L. Cercek & B. Cercek, "Effects of Ascorbate Ions on Intracellular Fluorescein Emission Polarization Spectra in Cancer and Normal Proliferating Cells," *Cancer Detection & Prevention* 10, 1-20 (1987).

TABLE 24

EFFECT OF ASCORBATE IONS ON SCM FACTOR SYNTHESIS IN CULTURED MCF7 HUMAN BREAST CANCER CELLS

| Treatment During 16 hrs of Incubation at 37° C. | Corrected ELISA $A_{405}{}^a$ | Corrected ELISA $A_{405}{}^a$ as % of Control |
|---|---|---|
| None (Control) | 1.7448 | 100.0 |
| $1 \times 10^{-3}$ M L-ascorbic acid, pH 7.1 | 0.9788 | 56.1 |

$^a$Corrected ELISA $A_{405}$ = (ELISA $A_{405}$) - (Background $A_{405}$)

Example 31

Effect of Synthetic SCM Factor and Fragments Thereof on Natural Cytotoxicity of Lymphocytes The purified synthetic SCM factor molecule and peptides F1-F5, F7, and F8, as described above in Example 16, were investigated to determine their suppressive effect on the natural cytotoxicity of lymphocytes against cancer cells, using the human myeloid cell line K 562 as target as measured by the conventional $^{51}$Cr release method (Example 13).

In brief, the K 562 target cells grown in suspension in RPMI-FBS culture medium were washed and labeled for 3 hours at 37° C. with 100 μCi sodium [$^{51}$Cr]chromate and then washed 4 times in RPMI growth medium. The effector lymphocytes used were isolated from heparinized peripheral blood of normal healthy donors using either appropriate density solutions to isolate the SCM-responding subpopulation of lymphocytes, as described above under "Isolation of SCM-responding Lymphocytes," or the conventional separation medium Histopaque 1077 for isolation of the total population of peripheral blood lymphocytes (PBL). The effector cell to target cell ratio used in these experiments was 40:1. Control samples contained target cells only and were used to determine background isotope release from the target cells. The test samples contained 0.2 mL aliquots of labeled target cells to which 0.2 mL of effector lymphocytes was added; the effector lymphocytes were either untreated or had been pretreated with either the entire synthetic SCM factor or any of the fragments designated F1 to F5, F7, or F8 for 2.5 hours at 37° C. The tests were carries out in triplicate. Cell suspensions were incubated for 18 hours at 37° C. in an atmosphere of 95% air and 5% $CO_2$. Samples were then centrifuged for 10 minutes at 200×g. From each test sample tube, a 0.2 mL aliquot of the supernatant was removed. Both the supernatant and the remaining cell pellet were counted in a Beckman gamma counter. The maximum possible isotope release was taken as the count obtained by adding the counts for the supernatant and cell pellets. The percentage of $^{51}$Cr release was determined for each of the triplicate samples; using the mean value of $^{51}$Cr release, the percentage of cytotoxicity was calculated according to the equation presented in Table 25.

As shown in the experiments whose results are given in Table 25, incubation of SCM-responding lymphocytes and of PBL with 35 femtomoles of synthetic SCM factor per lymphocyte decreased their natural killing efficiency or cytotoxicity against K 562 cells by 97% to 99.9% as compared to cytotoxicity of the untreated effector lymphocytes. This confirms the results previously obtained with the natural SCM factor present in ultrafiltrates of blood plasma from patients with cancer. The synthetic SCM factor suppresses the cytotoxicity of both the SCM-responding subpopulation of lymphocytes and the entire PBL population. As shown in Table 25, the NK-suppressive effect of synthetic SCM factor is irreversible and cannot be reversed by multiple washing of treated lymphocytes.

TABLE 25

EFFECT OF SYNTHETIC SCM FACTOR ON NATURAL LYMPHOCYTE CYTOTOXICITY AGAINST K 562 MYELOID CELLS

| Lymphocyte Fraction$^a$ | Percent Cytotoxicity$^b$: | | |
|---|---|---|---|
| | Untreated Lymphocytes | Treated Lymphocytes$^c$ | Treated & Washed Lymphocytes |
| SCM-R | 84.0 ± 3.0 | 0.1 ± 0.9 | 0.1 ± 0.9 |
| SCM-R | 72.0 ± 2.8 | 0.8 ± 0.7 | — |
| SCM-R | 45.6 ± 2.7 | 0.1 ± 0.8 | — |
| PBL | 77.8 ± 2.5 | 1.2 ± 1.0 | — |
| PBL | 72.7 ± 1.2 | 3.2 ± 0.7 | 3.0 ± 0.8 |
| PBL | 80.4 ± 1.8 | 2.6 ± 0.9 | 3.0 ± 0.8 |

$^a$All lymphocytes were isolated from normal healthy donors. SCM-R is the subpopulation of peripheral blood lymphocytes isolated from density gradient solutions, that yield the subpopulation which responds to phytohaemagglutinin (PHA) in the SCM test. PBL is the total population of peripheral blood lymphocytes isolated on Histopaque 1077 density solution.
$^b$Cytotoxicity was determined as in Example 13.
$^c$Treated lymphocytes were treated with 35 femtomoles of synthetic SCM factor per lymphocyte.
Values given are the mean of triplicate tests in each experiment. The effector/target ratio was 40:1.

To establish which part of the SCM-factor molecule is responsible for this NK-suppressive effect, we have treated the effector lymphocytes with peptides representing different regions of the amino acid sequence of synthetic SCM factor. As shown in Table 26, peptides that did not contain the seven carboxyl-terminal amino acids had no effect on the natural cytotoxicity of lymphocytes. However, peptides containing residues 14-29 (fragment F2) or 23-29 (fragment F8) are also inactive in suppressing cytotoxicity. Therefore the NK-suppressive activity appears to require the presence of amino acid residues 8-29 of the synthetic SCM molecule. This region is different from the region of synthetic SCM factor responsible for protection of protease from inhibition by α-I-PI, which resides in the amino terminus of the molecule (Example 28). It is also more extensive than the region of the SCM molecule responsible for SCM activity (residues 14-22), although it overlaps that region (Example 17). For example, peptide fragment F4, which extends from residue 14 to residue 22 and is fully active in the SCM test, does not cause any suppression of NK activity.

effect of SCM factors in vivo and enhance the resistance of cancer patients to the disease.

In addition to assays of clinical importance, the availability of such factors opens up new avenues for studying cancer. The ability to vary the amino acid sequences of the SCM factors in known ways allows the performance of structure-activity studies otherwise impossible. Also, the ability to label such factors allows the isolation of receptors or other molecules that interact with SCM factors in vivo. The pure, appropriately labeled SCM factor can be used for detection of receptors for the SCM factor on patients' lymphocytes. This can provide an alternative to the SCM test.

Although the present invention has been described in considerable detail with regard to certain preferred versions thereof, other versions are possible. Therefore, the spirit and scope of the appended claims should not be limited to the descriptions of the preferred versions contained herein.

What is claimed is:

TABLE 26

DETERMINATION OF THE CYTOTOXICITY SUPPRESSIVE PORTION OF THE SYNTHETIC SCM MOLECULE

| Control Untreated | Synthetic SCM Factor (1-29)[b] | F1 (1-22) | F2 (8-29) | F3 (8-22) | F4 (14-22) | F5 (1-13) | F7 (14-29) | F8 (23-29) |
|---|---|---|---|---|---|---|---|---|
| 72.7 ± 1.2 | 3.2 ± 0.1 | 78.5 ± 1.0 | 14.9 ± 1.5 | 74.5 ± 1.5 | 76.2 ± 1.3 | 72.7 ± 1.3 | — | — |
| 80.4 ± 1.0 | 3.1 ± 0.8 | 81.0 ± 1.0 | 2.6 ± 1.7 | 80.5 ± 1.0 | 81.0 ± 1.5 | 79.8 ± 0.9 | — | — |
| 46.5 ± 1.5 | 0.1 ± 0.8 | — | 2.4 ± 0.2 | — | 48.6 ± 1.3 | — | — | — |
| 71.2 ± 1.5 | — | — | — | — | — | — | 72.7 ± 1.0 | 71.7 ± 1.2 |
| 31.0 ± 2.0 | — | — | — | — | — | — | — | 33.0 ± 1.8 |

Percent Cytotoxicity[a]:

[a]Percent cytotoxicity was determined as in Example 13 using PBL. Lymphocytes were incubated with 35 femtomoles of either the entire synthetic SCM factor or peptides representing portions of it, for 2.5 hours at 37° C.
[b]The numerals in parentheses indicate the numbers of the amino acid residues included in the particular fragment of synthetic SCM factor.
Values given are the mean of triplicate tests in each experiment. The effector/target ratio was 40:1.

ADVANTAGES OF THE PRESENT INVENTION

Both the isolated and purified SCM factors of the present invention and the synthetic SCM factors and fragments of the present invention meet the needs previously enumerated. In particular, they allow the assay of the SCM response by the use of homogeneous challenging agents of defined structure. The availability of such challenging agents eliminates the need to use challenging agents partially purified from tissue extracts in the SCM assay. Such partially purified challenging agents are non-homogeneous, can vary from batch to batch in purity and potency, and can contain contaminants that interfere with the SCM test. The challenging agents of the present invention therefore give greater reliability and uniformity in both clinical and research studies.

The knowledge of the complete amino acid sequences of such SCM factor molecules allows their synthesis in quantity by either solid-phase peptide synthesis techniques or, alternatively, by genetic engineering techniques that can express the peptides in cells containing recombinant DNA.

Additionally, the availability of homogeneous and purified preparations of SCM factors makes possible the preparation of antibodies specific to them. The preparation of such antibodies allows the performance of immunoassays for the detection and monitoring of small quantities of SCM factor in vivo. This gives a new, noninvasive tool for the early detection of cancer and the monitoring of the efficacy of cancer treatment. Such assays can, for example, identify metastases before they would be otherwise detectable. Such antibodies can also be used directly in treatment methods to reduce the 1. A substantially purified cancer recognition factor, the factor being a peptide of nine amino acid residues to 35 amino acid residues including a core sequence of nine amino acid residues having an amphipathicity profile substantially equivalent to that of the sequence F-L-M-I-D-O-N-T-K, wherein the sixth amino acid of the core sequence is selected from the group consisting of Q and N, the seventh amino acid of the core sequence is selected from the group consisting of N and Q, and the ninth amino acid of the core sequence is selected from the group consisting of K and R, the factor producing at least a ten percent (10%) decrease in the intracellular fluorescence polarization value of lymphocytes capable of responding in the structuredness of the cytoplasmic matrix (SCM) test as isolated from donors afflicted with cancer.

2. The cancer recognition factor of claim 1 producing at least a 25 percent decrease in the intracellular fluorescence polarization of SCM-responding lymphocytes from donors afflicted with cancer.

3. The cancer recognition factor of claim 1 wherein the peptide comprises from 9 to 35 amino acid residues, and wherein the core sequence of 9 amino acid residues is $F-X_{15}-M-X_{17}-X_{18}-X_{19}-X_{20}-X_{21}-K$, wherein $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T.

4. The cancer recognition factor of claim 1 wherein the core sequence of 9 amino acid residues is F-L-M-I-D-Q-N-T-K.

5. The cancer recognition factor of claim 1 wherein the peptide has the sequence F-X-M-$X_{17}$-$X_{18}$-$X_{19}$-$X_{20}$-$X_{21}$-K, wherein $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T.

6. The cancer recognition factor of claim 5 wherein the peptide has the sequence F-L-M-I-D-Q-N-T-K.

7. The cancer recognition factor of claim 1 wherein the peptide has the sequence F-$X_9$-K-P-F-$X_{13}$-F-$X_{15}$-M-$X_{17}$-$X_{18}$-$X_{19}$-$X_{20}$-$X_{21}$-K, wherein $X_{13}$, $X_{15}$, and $X_{17}$ are each independently selected from the group consisting of I, L, and V; $X_{18}$ is selected from the group consisting of D and E; $X_9$, $X_{19}$, and $X_{20}$ are each independently selected from the group consisting of Q and N; and $X_{21}$ is selected from the group consisting of S and T.

8. The cancer recognition factor of claim 7 wherein the peptide has the sequence F-N-K-P-F-V-F-L-M-I-D-Q-N-T-K.

9. The cancer recognition factor of claim 1 wherein the peptide has the sequence F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K, wherein $X_{13}$, $X_{15}$, $X_{17}$, $X_{23}$, and $X_{25}$ are each independently selected from the group consisting of I, L and V; $X_{18}$ is selected from the group consisting of D and E; $X_9$, $X_{19}$, and $X_{20}$ are each independently selected from the group consisting of Q and N; and $X_{21}$ is selected from the group consisting of S and T.

10. The cancer recognition factor of claim 9 wherein the peptide has the sequence F-N-K-P-F-V-F-L-M-I-D-Q-N-T-K-V-P-L-F-M-G-K.

11. The cancer recognition factor of claim 1 wherein the peptide has the sequence M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K, wherein $X_2$, $X_6$, $X_{13}$, $X_{15}$, and $X_{17}$ are each independently selected from the group consisting of I, L, and V; $X_5$ and $X_{18}$ are each independently selected from the group consisting of D and E; $X_9$, $X_{19}$, and $X_{20}$ are each independently selected from the group consisting of Q and N; and $X_{21}$ is selected from the group consisting of S and T.

12. The cancer recognition factor of claim 11 wherein the peptide has the sequence M-I-P-P-E-V-K-F-N-K-P-F-V-F-L-M-I-D-Q-N-T-K.

13. A substantially purified cancer recognition factor useful in the structuredness of the cytoplasmic matrix (SCM) test consisting essentially of a peptide have an amino acid sequence of M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K, wherein $X_2$, $X_6$, $X_{13}$, $X_{15}$, $X_{17}$, $X_{23}$ and $X_{25}$ are each independently selected from the group consisting of I, L, and V; $X_5$ and $X_{18}$ are each independently selected from the group consisting of D and E; $X_9$, $X_{19}$, and $X_{20}$ are each independently selected from the group consisting of Q and N; and $X_{21}$ is selected from the group consisting of S and T, the factor producing at least a 10 percent decrease in the intracellular fluorescence polarization value of SCM-responding lymphocytes from donors afflicted with cancer.

14. A substantially purified cancer recognition factor useful in the structuredness of the cytoplasmic matrix (SCM) test consisting essentially of a peptide of from 29 to 35 amino acid residues including a core sequence at amino acids 14–22 of F-L-M-I-$X_{18}$-Q-N-T-K, wherein $X_{18}$ is selected from the group consisting of D and E, the factor producing at least a 10 percent decrease in the intracellular fluorescence polarization value of SCM-responding lymphocytes from donors afflicted with cancer.

15. The cancer recognition factor of claim 14 wherein the peptide has the sequence $X_1$-I-P-P-$X_5$-V-K-F-N-K-P-F-V-F-L-M-I-D-Q-N-T-K-$X_{23}$-P-L-F-M-G-K, wherein $X_1$ is selected from the group consisting of V, M, and S; $X_5$ is selected from the group consisting of E and D; and $X_{23}$ is selected from the group consisting of T and V.

16. The cancer recognition factor of claim 15 wherein the factor has the sequence V-I-P-P-E-VK-F-N-K-P-F-V-F-L-M-I-D-Q-N-T-K-V-P-L-F-M-G-K.

17. The cancer recognition factor of claim 15 wherein the factor has the sequence M-I-P-P-E-V-K-F-N-K-P-F-V-F-L-M-I-D-Q-N-T-K-V-P-L-F-M-G-K.

18. The cancer recognition factor of claim 14 wherein the factor has the sequence M-I-P-P-E-V-K-F-N-K-P-F-V-F-L-M-I-D-Q-N-T-K-C-P-C-F-M-G-C.

19. The cancer recognition factor of claim 14 wherein the factor has the sequence $X_1$-I-P-P-E-V-K-F-N-K-P-F-V-F-L-M-I-D-Q-N-T-K-C-C-L-F-M-G-K, wherein $X_1$ is selected from the group consisting of M and V.

20. The cancer recognition factor of claim 19 wherein the factor has the sequence M-I-P-P-E-V-K-F-N-K-P-F-V-F-L-M-I-D-Q-N-T-K-C-C-L-F-M-G-K.

21. The cancer recognition factor of claim 14 wherein the factor has the sequence $X_1$-I-P-P-E-V-K-F-N-K-P-F-V-F-L-M-I-D-Q-N-T-K-R-P-L-F-M-G-K, wherein $X_1$ is selected from the group consisting of R and S.

22. The cancer recognition factor of claim 21 wherein the factor has the sequence R-I-P-P-E-V-K-F-N-K-P-F-V-F-L-M-I-D-Q-N-T-K-R-P-L-F-M-G-K.

23. The cancer recognition factor of claim 14 wherein the factor has the sequence V-I-P-P-E-V-K-F-N-K-P-F-V-F-L-M-I-D-Q-N-T-K-C-P-L-F-M-G-K.

24. The cancer recognition factor of claim 14 wherein the factor has the sequence V-I-P-P-E-V-K-F-N-C-P-F-V-F-L-M-I-D-Q-N-T-K-V-P-L-F-M-G-K.

25. The cancer recognition factor of claim 14 wherein the peptide is selected from the group consisting of peptides having amino acid sequences $X_1$-I-P-P-E-V-K-F-N-K-P-F-V-F-L-M-I-D-Q-N-T-K-C-P-C-F-M-G-C and $X_1$-I-P-P-E-V-K-F-N-K-P-F-V-F-L-M-I-D-Q-N-T-K-C-P-C-F-M-G-C-V-V-N-C-T-E, wherein $X_1$ is selected from the group consisting of R and S.

26. The cancer recognition factor of claim 25 wherein the peptide has the amino acid sequence R-I-P-P-E-V-K-F-N-K-P-F-V-F-L-M-I-D-Q-N-T-K-C-P-C-F-M-G-C.

27. The cancer recognition factor of claim 14 wherein the peptide is selected from the group consisting of peptides having amino acid sequences $X_1$-I-P-P-E-V-K-F-N-K-P-F-V-F-L-M-I-E-Q-N-T-K-S-P-L-F-M-G-K and $X_1$-I-P-P-E-V-K-F-N-K-P-F-V-F-L-M-I-E-Q-N-T-K-S-P-L-F-M-G-K-V-V-N-P-T-Q, wherein $X_1$ is selected from the group consisting of V and S.

28. The cancer recognition factor of claim 27 wherein the peptide has the amino acid sequence V-I-P-P-E-V-K-F-N-K-P-F-V-F-L-M-I-E-Q-N-T-K-S-P-L-F-M-G-K.

29. The cancer recognition factor of claim 14 wherein the factor has the amino acid sequence $X_1$-I-P-P-E-V-K-F-N-K-P-F-V-F-L-M-I-E-Q-N-T-K-

S-P-L-F-M-G-K-V-V-N-P-T-Q, wherein X₁ is selected from the group consisting of S and V.

30. The cancer recognition factor of claim 29 wherein the peptide has the amino acid sequence S-I-P-P-E-V-K-F-N-K-P-F-V-F-L-M-I-E-Q-N-T-K-S-P-L-F-M-G-K-V-V-N-P-T-Q.

31. A substantially purified cancer recognition factor active in the structuredness of the cytoplasmic matrix (SCM) test consisting essentially of low molecular weight peptide passing through filters with a nominal 1000-dalton molecular weight cutoff and retained by filters with a nominal 500-dalton molecular weight cutoff, the factor being substantially free of intact $\alpha_1$-antitrypsin or other molecules larger than about 10,000 daltons, the factor producing at least a 10 percent decrease in the intracellular fluorescence polarization value of SCM-responding lymphocytes from donors afflicted with cancer as measured by the standard SCM test.

32. The cancer recognition factor of claim 31 producing at least a 25 percent decrease in the intracellular fluorescence polarization value of SCM-responding lymphocytes from donors afflicted with cancer as measured by the standard SCM test.

33. A method for testing lymphocytes obtained from a mammalian donor for the presence or absence of malignancy in the donor comprising the steps of:
   (a) contacting a suspension of the lymphocytes with the substantially purified cancer recognition factor of claim 1, and
   (b) determining the decrease in the structuredness of the cytoplasmic matrix of the lymphocytes resulting from the step of contacting the suspension of the lymphocytes.

34. The method of claim 33 wherein the step of determining the decrease in the structuredness of the cytoplasmic matrix comprises the steps of:
   (a) measuring the fluorescence polarization, $P_S$, for a first aliquot of the lymphocytes that has been contacted with the cancer recognition factor;
   (b) measuring the fluorescence polarization, $P_C$, for a second aliquot of the lymphocytes that has not been contacted with the cancer recognition factor; and
   (c) determining the ratio of $P_S$ to $P_C$, whereby a ratio of $P_S$ to $P_C$ of less than about 0.9 indicates the presence of a malignancy in the body of the donor of the lymphocytes.

35. The method of claim 33 wherein the step of determining the decrease in the structuredness of the cytoplasmic matrix comprises the steps of:
   (a) measuring the fluorescence polarization, $P_S$, for a first aliquot of the lymphocytes that has been contacted with the cancer recognition factor;
   (b) measuring the fluorescence polarization, $P_M$, for a second aliquot of the lymphocytes that has been contacted with a mitogen selected from the group consisting of phytohaemagglutinin, concanavalin A, and pokeweed mitogen; and
   (c) determining an SCM response ratio, $R_{SCM}$, as the ratio of $P_S$ to $P_M$, whereby an $RR_{SCM}$ of less than about 0.9 indicates the presence of a malignancy in the body of the donor of the lymphocytes.

36. A method for screening a blood sample for the presence of a malignancy in the body of the donor of the blood sample comprising the steps of:
   (a) separating potentially SCM-responding lymphocytes from the blood sample;
   (b) contacting the separated lymphocytes with the substantially purified cancer recognition factor of claim 1 to stimulate the lymphocytes;
   (c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;
   (d) exciting the stimulated fluorogenic agent-containing lymphocytes with polarized light thereby causing the lymphocytes to fluoresce;
   (e) measuring the vertically polarized and horizontally polarized fluorescence emissions from the fluorescing lymphocytes for determining a polarization value for the fluorescing lymphocytes; and
   (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

37. The method of claim 36 wherein steps (b) and (c) occur simultaneously.

38. A method for testing lymphocytes obtained from a mammalian donor for the presence or absence of malignancy in the donor comprising the steps of:
   (a) contacting a suspension of the lymphocytes with the substantially purified cancer recognition factor of claim 13, and
   (b) determining the decrease of the cytoplasmic matrix of the lymphocytes resulting from the step of contacting the suspension of the lymphocytes.

39. The method of claim 38 wherein the step of determining the decrease in the structuredness of the cytoplasmic matrix comprises the steps of:
   (a) measuring the fluorescence polarization, $P_S$, for a first aliquot of the lymphocytes that has been contacted with the cancer recognition factor;
   (b) measuring the fluorescence polarization, $P_C$, for a second aliquot of the lymphocytes that has not been contacted with the cancer recognition factor; and
   (c) determining the ratio of $P_S$ to $P_C$, whereby a ratio of $P_S$ to $P_C$ of less than about 0.9 indicates the presence of a malignancy in the body of the donor of the lymphocytes.

40. The method of claim 38 wherein the step of determining the decrease in the structuredness of the cytoplasmic matrix comprises the steps of:
   (a) measuring the fluorescence polarization, $P_S$, for a first aliquot of the lymphocytes that has been contacted with the cancer recognition factor;
   (b) measuring the fluorescence polarization, $P_M$, for a second aliquot of the lymphocytes that has been contacted with a mitogen selected from the group consisting of phytohaemagglutinin, concanavalin A, and pokeweed mitogen; and
   (c) determining an SCM response ratio, $R_{SCM}$, as the ratio of $P_S$ to $P_M$, whereby an $RR_{SCM}$ of less than about 0.9 indicates the presence of a malignancy in the body of the donor of the lymphocytes.

41. A method for screening a blood sample for the presence of a malignancy in the body of the donor of the blood sample comprising the steps of:
   (a) separating potentially SCM-responding lymphocytes from the blood sample;

(b) contacting the separated lymphocytes with the substantially purified cancer recognition factor of claim 13 to stimulate the lymphocytes;

(c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;

(d) exciting the stimulated fluorogenic agent-containing lymphocytes with polarized light thereby causing the lymphocytes to fluoresce;

(e) measuring the vertically polarized and horizontally polarized fluorescence emissions from the fluorescing lymphocytes for determining a polarization value for the fluorescing lymphocytes; and (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

42. The method of claim 41 wherein steps (b) and (c) occur simultaneously.

43. A method for testing lymphocytes obtained from a mammalian donor for the presence or absence of malignancy in the donor comprising the steps of:

(a) contacting a suspension of the lymphocytes with the substantially purified cancer recognition factor of claim 14; and (b) determining the decrease in the structuredness of the cytoplasmic matrix of the lymphocytes resulting from the step of contacting the suspension of the lymphocytes.

44. The method of claim 43 wherein the step of determining the decrease in the structuredness of the cytoplasmic matrix comprises the steps of:

(a) measuring the fluorescence polarization, $P_S$, for a first aliquot of the lymphocytes that has been contacted with the cancer recognition factor;

(b) measuring the fluorescence polarization, $P_C$, for a second aliquot of the lymphocytes that has not been contacted with the cancer recognition factor; and (c) determining the ratio of $P_S$ to $P_C$, whereby a ratio of $P_S$ to $P_C$ of less than about 0.9 indicates the presence of a malignancy in the body of the donor of the lymphocytes.

45. The method of claim 43 wherein the step of determining the decrease in the structuredness of the cytoplasmic matrix comprises the steps of:

(a) measuring the fluorescence polarization, $P_S$, for a first aliquot of the lymphocytes that has been contacted with the cancer recognition factor;

(b) measuring the fluorescence polarization, $P_M$, for a second aliquot of the lymphocytes that has been contacted with a mitogen selected from the group consisting of phytohaemagglutinin, concanavalin A, and pokeweed mitogen; and (c) determining an SCM response ratio, $R_{SCM}$, as the ratio of $P_S$ to $P_M$, whereby an $RR_{SCM}$ of less than about 0.9 indicates the presence of a malignancy in the body of the donor of the lymphocytes.

46. A method for screening a blood sample from the presence of a malignancy in the body of the donor of the blood sample comprising the steps of:

(a) separating potentially SCM-responding lymphocytes from the blood sample;

(b) contacting the separated lymphocytes with the substantially purified cancer recognition factor of claim 14 to stimulate the lymphocytes;

(c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;

(d) exciting the stimulated fluorogenic agent-containing lymphocytes with polarized light thereby causing the lymphocytes to fluoresce;

(e) measuring the vertically polarized and horizontally polarized fluorescence emissions from the fluorescing lymphocytes for determining a polarization value for the fluorescing lymphocytes; and (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

47. The method of claim 46 wherein steps (b) and (c) occur simultaneously.

48. A method for testing lymphocytes obtained from a mammalian donor for the presence or absence of malignancy in the donor comprising the steps of:

(a) contacting a suspension of the lymphocytes with the substantially purified cancer recognition factor of claim 31; and (b) determining the decrease in the structuredness of the cytoplasmic matrix of the lymphocytes resulting from the step of contacting the suspension of the lymphocytes.

49. The method of claim 48 wherein the steps of determining the decrease in the structuredness of the cytoplasmic matrix comprises the steps of:

(a) measuring the fluorescence polarization, $P_S$, for a first aliquot of the lymphocytes that has been contacted with the cancer recognition factor;

(b) measuring the fluorescence polarization, $P_C$, for a second aliquot of the lymphocytes that has not been contacted with the cancer recognition factor; and (c) determining the ratio of $P_S$ to $P_C$, whereby a ratio of $P_S$ to $P_C$ of less than about 0.9 indicates the presence of a malignancy in the body of the donor of the lymphocytes.

50. The method of claim 48 wherein the step of determining the decrease in the structuredness of the cytoplasmic matrix comprises the steps of:

(a) measuring the fluorescence polarization, $P_S$, for a first aliquot of the lymphocytes that has been contacted with the cancer recognition factor;

(b) measuring the fluorescence polarization, $P_M$, for a second aliquot of the lymphocytes that has been contacted with a mitogen selected from the group consisting of phytohaemagglutinin, concanavalin A, and pokeweed mitogen; and (c) determining an SCM response ratio, $R_{SCM}$, as the ratio of $P_S$ to $P_M$, whereby an $RR_{SCM}$ of less than about 0.9 indicates the presence of a malignancy in the body of the donor of the lymphocytes.

51. A method for screening a blood sample from the presence of a malignancy in the body of the donor of the blood sample comprising the steps of:
  (a) separating potentially SCM-responding lymphocytes from the blood sample;
  (b) contacting the separated lymphocytes with the substantially purified cancer recognition factor of claim 14 to stimulate the lymphocytes;
  (c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;
  (d) exciting the stimulated fluorogenic agent-containing lymphocytes with polarized light thereby causing the lymphocytes to fluoresce;
  (e) measuring the vertically polarized and horizontally polarized fluorescence emissions from the fluorescing lymphocytes for determining a polarization value for the fluorescing lymphocytes; and
  (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

52. The method of claim 51 wherein steps (b) and (c) occur simultaneously.

53. A substantially purified cancer factor produced by a process comprising the steps of:
  (a) obtaining a body fluid from a donor afflicted with cancer;
  (b) separating a first fraction of the body fluid comprising molecules having an apparent molecular weight of greater than 1000 daltons as determined by ultrafiltration through an ultrafilter with a nominal molecular weight cutoff of 1000 daltons, from a second fraction comprising molecules having an apparent molecular weight of less than 1000 daltons; and
  (c) purifying the second fraction to obtain a substantially pure cancer recognition factor, wherein the step of purifying the second fraction comprises the step of desalting the second fraction by loading the second fraction on gel filtration column with a fractionation range of about 0 to about 700 daltons and capable of separating the salts therefrom, eluting the loaded material from the column with water, and collecting that portion eluting at an elution volume between about 0.3 and about 0.5 times the total chromatographic bed volume to increase the specific activity of the cancer recognition factor in the collected desalted portion relative to the specific activity in the second fraction.

54. The substantially purified cancer recognition factor of claim 53 wherein the process further comprises:
  (d) loading the collected desalted portion on a gel filtration column having a fractionation range up to about 1500 daltons to about 30,000 daltons;
  (e) eluting the material loaded onto the column in step (d) from the column with a weak aqueous solution of an ammonium salt; and
  (f) collecting that portion eluting at an elution volume between about 0.4 times and about 0.6 times the total chronographic bed volume thereby increasing the specific activity of the cancer recognition factor in the collected eluate relative to the specific activity in the collected desalted portion.

55. The substantially purified cancer recognition factor of claim 54, wherein the process further comprises the steps of:
  (g) loading the collected eluate from the gel filtration column on a diethylaminoethyl cellulose anion-exchange column;
  (h) eluting the material loaded onto the column in step (g) from the column with an increasing concentration of an ammonium salt; and
  (i) collecting that portion of the eluate eluting from the column at about 0.28 to about 0.31M of the ammonium salt, thereby increasing the specific activity of the cancer recognition factor in the collected eluate from the diethylaminoethyl cellulose anion-exchange column relative to the specific activity in the eluate from the gel filtration column.

56. The substantially purified cancer recognition factor of claim 55, wherein the process further comprises the step of purifying the cancer recognition factor from the collected eluate from the diethylaminoethyl cellulose anion-exchange column to substantial homogeneity by reverse phase high pressure chromatography.

57. A method for testing lymphocytes obtained from a mammalian donor for the presence or absence of malignancy in the donor comprising the steps of:
  (a) contacting a suspension of the lymphocytes with the substantially purified cancer recognition factor of claim 6; and
  (b) determining, by the structuredness of the cytoplasmic matrix (SCM) test, the decrease in the structuredness of the cytoplasmic matrix of the lymphocytes resulting from the step of contacting the suspension of the lymphocytes, wherein a decrease of the structuredness of the cytoplasmic matrix is indicative of the presence of malignancy.

58. The method of claim 57 wherein the step of determining the decrease in the structuredness of the cytoplasmic matrix comprises the steps of:
  (a) measuring the fluorescence polarization, $P_S$, for a first aliquot of the lymphocytes that has been contacted with the cancer recognition factor;
  (b) measuring the fluorescence polarization, $P_C$, for a second aliquot of the lymphocytes that has not been contacted with the cancer recognition factor; and
  (c) determining the ratio of $P_S$ to $P_C$, whereby a ratio of $P_S$ to $P_C$ of less than about 0.9 indicates the presence of a malignancy in the body of the donor of the lymphocytes.

59. The method of claim 57 wherein the step of determining the decrease in the structuredness of the cytoplasmic matrix comprises the steps of:
  (a) measuring the fluorescence polarization, $P_S$, for a first aliquot of the lymphocytes that has been contacted with the cancer recognition factor;
  (b) measuring the fluorescence polarization, $P_M$, for a second aliquot of the lymphocytes that has been contacted with a mitogen selected from the group consisting of phytohaemagglutinin, concanavalin A, and pokeweed mitogen; and
  (c) determining an SCM response ratio, $RR_{SCM}$, as the ratio of $P_S$ to $P_M$, whereby an $RR_{SCM}$ of less than about 0.9 indicates the presence of a malignancy in the body of the donor of the lymphocytes.

60. A method for screening a blood sample from the presence of a malignancy in the body of the donor of the blood sample comprising the steps of:
 (a) separating potentially SCM-responding lymphocytes from the blood sample;
 (b) contacting the separated lymphocytes with the substantially purified cancer recognition factor of claim 6 to stimulate the lymphocytes;
 (c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;
 (d) exciting the stimulated fluorogenic agent-containing lymphocytes with polarized light thereby causing the lymphocytes to fluoresce;
 (e) measuring the vertically polarized and horizontally polarized fluorescence emissions from the fluorescing lymphocytes for determining a polarization value for the fluorescing lymphocytes; and
 (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

61. The method of claim 60 wherein steps (b) and (c) occur simultaneously.

62. The cancer recognition factor of claim 1 wherein the peptide comprises from 13 to 35 amino acid residues and wherein the core sequence comprises 13 amino acid residues, the core sequence being $F-X_{13}-F-X_{15}-M-X_{17}-X_{18}-X_{19}-X_{20}-X_{21}-K-X_{23}-P$, wherein $X_{13}$, $X_{15}$, $X_{17}$, and $X_{23}$ are each independently selected from the group consisting of I, L and V; $X_{18}$ is selected from the group consisting of D and E; $X_{19}$ and $X_{20}$ are each independently selected from the group consisting of Q and N; and $X_{21}$ is selected from the group consisting of S and T.

63. The cancer recognition factor of claim 1 wherein the peptide comprises from 18 to 35 amino acids, and wherein the core sequence comprises 18 amino acid residues, the core sequence being $X_9-K-P-F-X_{13}-F-X_{15}-M-X_{17}-X_{18}-X_{19}-X_{20}-X_{21}-K-X_{23}-P-X_{25}-F$, wherein $X_{13}$, $X_{15}$, $X_{17}$, $X_{23}$, and $X_{25}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T.

64. A method for testing lymphocytes obtained from a mammalian donor for the presence or absence of malignancy in the donor comprising the steps of:
 (a) contacting a suspension of the lymphocytes with the substantially purified cancer recognition factor of claim 3; and
 (b) determining, by the structuredness of the cytoplasmic matrix (SCM) test, the decrease in the structuredness of the cytoplasmic matrix of the lymphocytes resulting from the step of contacting the suspension of the lymphocytes, or wherein a decrease of the structuredness of the cytoplasmic matrix is indicative of the presence of malignancy.

65. The method of claim 64 wherein the step of determining the decrease of the structuredness of the cytoplasmic matrix comprises the steps of:
 (a) measuring the fluorescence polarization, $P_S$, for a first aliquot of the lymphocytes that has been contacted with the cancer recognition factor;
 (b) measuring the fluorescence polarization, $P_C$, for a second aliquot of the lymphocytes that has not been contacted with the cancer recognition factor; and
 (c) determining the ratio of $P_S$ to $P_C$, whereby a ratio of $P_S$ to $P_C$ of less than about 0.9 indicates the presence of a malignancy in the body of the donor of the lymphocytes.

66. The method of claim 64 wherein the step of determining the decrease in the structuredness of the cytoplasmic matrix comprises the steps of:
 (a) measuring the fluorescence polarization, $P_S$, for a first aliquot of the lymphocytes that has been contacted with the cancer recognition factor;
 (b) measuring the fluorescence polarization, $P_M$, for a second aliquot of the lymphocytes that has been contacted with a mitogen selected from the group consisting of phytohaemagglutinin, concanavalin A, and pokeweed mitogen; and
 (c) determining an SCM response ratio, $RR_{SCM}$, as the ratio of $P_S$ to $P_M$, whereby an $RR_{SCM}$ of less than about 0.9 indicates the presence of a malignancy in the body of the donor of the lymphocytes.

67. A method for screening a blood sample from the presence of a malignancy in the body of the donor of the blood sample comprising the steps of:
 (a) separating potentially SCM-responding lymphocytes from the blood sample;
 (b) contacting the separated lymphocytes with the substantially purified cancer recognition factor of claim 6 to stimulate the lymphocytes;
 (c) contacting the stimulated lymphocytes with a fluorogenic agent precursor for a sufficient time for the precursor to penetrate the lymphocytes for intracellular enzymatic hydrolysis to a fluorogenic agent, thereby generating stimulated fluorogenic agent-containing lymphocytes;
 (d) exciting the stimulated fluorogenic agent-containing lymphocytes with polarized light thereby causing the lymphocytes to fluoresce;
 (e) measuring the vertically polarized and horizontally polarized fluorescence emissions from the fluorescing lymphocytes for determining a polarization value for the fluorescing lymphocytes; and
 (f) comparing the determined polarization value for the stimulated lymphocytes with a polarization value for a control aliquot of lymphocytes from the same donor which has been subjected to the operation of steps (a), (c), (d), and (e) but not (b), thereby to indicate the presence or absence of cancer in the body of the donor of the lymphocytes.

68. The method of claim 67 wherein steps (b) and (c) occur simultaneously.

* * * * *